(12) United States Patent
Elliott et al.

(10) Patent No.: US 7,265,104 B2
(45) Date of Patent: Sep. 4, 2007

(54) TETRAAZABENZO[E]AZULENE DERIVATIVES AND ANALOGS THEREOF

(75) Inventors: Richard L. Elliott, East Lyme, CT (US); Kimberly O. Cameron, East Lyme, CT (US); Marlys Hammond, Blue Bell, PA (US)

(73) Assignee: Pfizer Inc., New York, NY (US)

( * ) Notice: Subject to any disclaimer, the term of this patent is extended or adjusted under 35 U.S.C. 154(b) by 143 days.

(21) Appl. No.: 11/134,790

(22) Filed: May 19, 2005

(65) Prior Publication Data

US 2005/0267100 A1    Dec. 1, 2005

Related U.S. Application Data

(60) Provisional application No. 60/574,033, filed on May 25, 2004.

(51) Int. Cl.
C07D 519/00    (2006.01)
A61K 31/551    (2006.01)
A61P 43/00    (2006.01)

(52) U.S. Cl. ..................... 514/220; 540/499
(58) Field of Classification Search ............... 540/499; 514/220
See application file for complete search history.

(56) References Cited

U.S. PATENT DOCUMENTS

| 4,080,323 A | 3/1978 | Walser et al. | 260/239.3 |
|---|---|---|---|
| 5,646,140 A | 7/1997 | Sugg et al. | 517/221 |
| 5,798,353 A | 8/1998 | Badorc et al. | 514/221 |

FOREIGN PATENT DOCUMENTS

| DE | 2318673 | 11/1974 |
|---|---|---|
| DE | 2426305 | 1/1975 |
| DE | 2813549 | 10/1978 |
| GB | 1470803 | 5/1974 |
| NL | 7803585 | 10/1978 |
| WO | WO9528391 | 10/1995 |
| WO | WO9528419 | 10/1995 |
| WO | WO 0068209 | 11/2000 |

OTHER PUBLICATIONS

Smith, G. P. et al., Science, vol. 213, Aug. 28, 1981, pp. 1036-1037, "Abdominal Vagotomy Blocks the Satiety Effect of Cholecystokinin in the Rat".
Crawley J. N. et al., J. Pharmacol. Exp. Ther., vol. 257, Issue 3, pp. 1076-1080, Jun. 1, 1991, "Centrally administered cholecystokinin suppresses feeding through a peripheral-type receptor mechanism".
Gibbs J. et al., Journal of Comparative Physiological Psychology, vol. 84, No. 3, pp. 488-495, 1973, "Cholecystokinin Decreases Food Intake in Rates".
Himick B. A. et al., American Physiological Society, vol. 267, pp. R841-R851, 1994, "CCK/gastrin-like immunoreactivity in brain and gut, and CCK suppression of feeding in goldfish".
Hirosue Y. et al., American Physiological Society, vol. 265, pp. R481-R486, 1993, "Cholecystokinin octapeptide analogues suppress food intake via central CCK-A receptors in mice".
Asin K. E. et al., Pharmacology Biochemistry and Behavior, vol. 42, pp. 699-704, 1992, "A-71623, a Selective CCK-A Receptor Agonist, Suppresses Food Intake in the Mouse, Dog, and Monkey".
Sugg E. E. et al., Pharmaceutical Biotechnology, vol. 11, pp. 507-524, 1998, "Integration of Pharmaceutical Discovery and Development".
Sherrill R. G. et al., Bioorganic & Medicinal Chemistry Letters, vol. 11(9), pp. 1145-1148, 2001, "1,4-Benzodiazepine Peripheral Cholecystokinin (CCK-A) Receptor Agonists".
Henke B. R. et al., J. Med. Chem., vol. 40(17), pp. 2706-2725, 1997, "Optimization of 3-(1H-lndazol-3-ylmethyl)-1,5-benzodiazepines as Potent, Orally Active CCK-A Agonists".
Henke B. R. et al., J. Med. Chem., vol. 39(14), pp. 2655-2658, 1996, "3-(1H-lndazol-3-ylmethyl)-1,5-benzo-diazepines: CCK-A Agonists That Demonstrate Oral Activity as Satiety Agents".
Langlois M. et al., J. Heterocyclic Chem. vol. 19(1), pp. 193-200, 1982, "Synthese de nouvelles amidines bicycliques. 1. Derives de l'imidazole, du triazole-1,3,4 et du tetrazole".
English Language Equivalent for DE2318673 is GB1462095.
English Language Equivalent for DE2426305 is US4164498.
Bignon, et al., "SR146131: A New Potent, Orally Active, and Selective Nonpeptide Cholecystokinin Subtype 1 Receptor Agonist. ll: In Vivo Pharmacological Characterization," JPET 289: 752-761, 1999.
Chow, et al., "Fused Heterocycles from Substituted 1, 3, 4, 5-Tetrahydro-1-phenyl-4thioxo-8-(trifluoromethyl)-2H-1, 5-benzodiazepin-2-ones," Applebrook Research Center, Animal Health Products Divisions, SmithKline Corporation, West Chester, PA 19380, USA; vol. 13, pp. 163-167, Feb. 1976.
Darrow, et al., "Structurally similar small molecule photoaffinity CCK-A agonists and antagonists as novel tools for directly probing 7TM receptor-ligand interactions,"Science Direct—Bioorganic & Medicinal chemistry Letters, Abstract available online Feb. 16, 1999.
Cabeza, et al., "Formation of a Highly Functionalized Azulene Ligand by Metal Cluster-Mediated Coupling of Three Conjugated Diynes," Organometallics, 2003, 22, pp. 1164-1166.

*Primary Examiner*—Bruck Kifle
(74) *Attorney, Agent, or Firm*—Gregg C. Benson; Robert M. Kennedy

(57) ABSTRACT

This invention relates to CCK-A agonists of Formula (I)

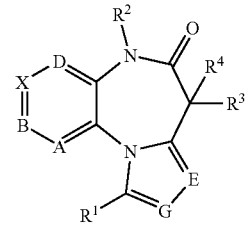

wherein $R^1$-$R^4$, A, B, X, D, E and G are as defined in the specificiation, as well as, among other things, pharmaceutical compositions containing the compounds and methods of use of the compounds and compositions. The compounds are useful in treating obesity.

37 Claims, No Drawings

TETRAAZABENZO[E]AZULENE DERIVATIVES AND ANALOGS THEREOF

CROSS REFERENCE TO RELATED APPLICATION

This application claims priority from U.S. Provisional Patent Application Ser. No. 60/574,033, filed May 25, 2004, incorporated herein by reference.

FIELD OF THE INVENTION

This invention relates to compounds of Formula (I), pharmaceutical compositions comprising the compounds, either alone or in combination with other pharmaceutical agents, methods of use of the compounds and combinations, and intermediates and methods useful in the preparation of the compounds. The compounds of Formula (I) are agonists of the cholesystokinin-A (CCK-A) receptor and are therefore useful, for example, for weight management and the treatment of obesity and associated diseases.

BACKGROUND OF THE INVENTION

Obesity is a major public health concern because of its increasing prevalence and associated health risks. Moreover, obesity may affect a person's quality of life through limited mobility and decreased physical endurance as well as through social, academic and job discrimination.

Obesity and overweight are generally defined by body mass index (BMI), which is correlated with total body fat and serves as a measure of the risk of certain diseases. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$ or higher. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

Recent studies have found that obesity and its associated health risks are not limited to adults, but also affect children and adolescents to a startling degree. According to the Center for Disease Control, the percentage of children and adolescents who are defined as overweight has more than doubled since the early 1970s, and about 15 percent of children and adolescents are now overweight. Risk factors for heart disease, such as high cholesterol and high blood pressure, occur with increased frequency in overweight children and adolescents compared with normal-weight subjects of similar age. Also, type 2 diabetes, previously considered an adult disease, has increased dramatically in children and adolescents. Overweight conditions and obesity are closely linked to type 2 diabetes. It has recently been estimated that overweight adolescents have a 70% chance of becoming overweight or obese adults. The probability increases to about 80% if at least one parent is overweight or obese. The most immediate consequence of being overweight as perceived by children themselves is social discrimination.

There are possible adverse health consequences of being overweight or obese as such individuals are at increased risk for ailments (co-morbidities) such as hypertension, dyslipidemia, type 2 (non-insulin dependent) diabetes, insulin resistance, glucose intolerance, hyperinsulinemia, coronary heart disease, angina pectoris, congestive heart failure, stroke, gallstones, cholescystitis, cholelithiasis, gout, osteoarthritis, obstructive sleep apnea and respiratory problems, gall bladder disease, certain forms of cancer (e.g., endometrial, breast, prostate, and colon) and psychological disorders (such as depression, eating disorders, distorted body image and low self esteem). The negative health consequences of obesity make it the second leading cause of preventable death in the United States and impart a significant economic and psychosocial effect on society. See, McGinnis M, Foege W H., "Actual Causes of Death in the United States," JAMA, 270, 2207-12 (1993).

Obesity is now recognized as a chronic disease that requires treatment to reduce its associated health risks. Although weight loss is an important treatment outcome, one of the main goals of obesity management is to improve cardiovascular and metabolic values to reduce obesity-related morbidity and mortality. It has been shown that 5-10% loss of body weight can substantially improve metabolic values, such as blood glucose, blood pressure, and lipid concentrations. Hence, it is believed that a 5-10% intentional reduction in body weight may reduce morbidity and mortality.

Currently available prescription drugs for managing obesity generally reduce weight by primarily inducing satiety or decreasing dietary fat absorption. Satiety is achieved by increasing synaptic levels of norepinephrine, serotonin, or both. For example, stimulation of serotonin receptor subtypes 1B, 1D, and 2C and 1- and 2-adrenergic receptors decreases food intake by regulating satiety. See, Bray G A, "The New Era of Drug Treatment. Pharmacologic Treatment of Obesity: Symposium Overview," Obes Res., 3 (suppl 4), 415s-7s (1995). Adrenergic agents (e.g., diethylpropion, benzphetamine, phendimetrazine, mazindol, and phentermine) act by modulating central norepinephrine and dopamine receptors through the promotion of catecholamine release. Older adrenergic weight-loss drugs (e.g., amphetamine, methamphetamine, and phenmetrazine), which strongly engage in dopamine pathways, are no longer recommended because of the risk of their abuse. Fenfluramine and dexfenfluramine, both serotonergic agents used to regulate appetite, are no longer available for use.

Cholecystokinin (CCK) is a brain-gut peptide that acts as a gastrointestinal hormone, neurotransmitter and neuromodulator in the central and the peripheral nervous systems. Cholecystokinin is a peptide that exists in multiple active forms of varying lengths (e.g. CCK-58; CCK-39; CCK-33; CCK-8; and CCK-4), with different forms predominating in different species. Cholecystokinin-58 is the major molecular form in man, dog and cat but not in pig, cattle or rat intestine. See, e.g., G. A. Eberlien, V. E. Eysselein and H. Goebell, 1988, *Peptides* 9, pp. 993-998. CCK's peripheral effects, where the O-sulfated octapeptide CCK-8S is believed to be the predominate form, are centered on its role as a gastrointestinal satiety factor.

It has been shown that CCK is released from mucosal 1-cells of the duodenum and jejunum in response to a meal, particularly in response to fat or protein in the meal. Once released, CCK initiates a number of responses coordinated to promote digestion and regulate food intake, including mediating bile emptying from the gall bladder, regulating the release of digestive enzymes from the pancreas, controlling gastric emptying by regulation of the pyloric sphincter, as well as neuronal signaling to the CNS (central nervous system) via vagal afferent neurons.

Within the CNS, CCK has been found in numerous anatomical locations, including the cerebral cortex, hippocampus, septum, amygdala, olfactory bulb, hypothalamus, thalamus, parabrachial nucleus, raphe nucleus, substantia nigra, ventral mesencephalon, nucleus tractus solatarius, ventral medulla, and spinal cord. See, e.g., T. Hokfelt et al., 1988, *J. Chem. Neuroanat.* 1, pp. 11-52; J. J. Vanderhaeghen, J. C. Signeu and W. Gepts, 1975, *Nature* 257, pp. 604-605; and J. J. Vanderhaegen and S. N. Schiffmann (1992) pp. 38-56, Eds. C. T. Dourish, S. J. Cooper, S. D. Iversen and L. L. Iversen, Oxford University Press, Oxford.

Neuronal CCK is believed to mediate a number of events within the CNS, including modulating dopaminergic neurotransmission and anxiogenic effects, as well as affecting cognition and nociception. See, e.g., J. N. Crawley and R. L. Corwin, 1994, Peptides, 15:731-755; N. S. Baber, C. T. Dourish, and D. R. Hill, Pain (1989), 39 (3), 307-28; and P. De Tullio, J. Delarge and B. Pirotte, Expert Opinion on Investigational Drugs (2000), 9 (1), 129-146.

Cholecystokinin has been shown to mediate its diverse hormonal and neuromodulatory functions through two receptor subtypes: the CCK-A ($CCK_1$) and CCK-B ($CCK_2$) subtypes (see, e.g., G. N. Woodruff and J. Hughes, Annu. Rev. Pharmacol. Toxicol. (1991), 31: 469-501), both of which have been sequenced and cloned from rats (see, e.g., S. A. Wank et al. (1992) *Proc. Natl. Acad. Sci. USA*, 89, 8691-8695) and humans (see, e.g., J. R. Pisegna et al., 1992, *Biochem. Biophys. Res. Commun.* 189, pp. 296-303).

Both CCK-A and CCK-B receptor subtypes belong to the seven transmembrane G-protein-coupled superfamily of receptors. The nucleotide sequences of the peripheral CCK-A receptor and central CCK-A receptor are identical in humans; likewise, the human CCK-B receptor and gastrin receptor have been found to be identical. See, e.g., S. A. Wank et al., (1994), *NY Acad. Sci.* 713, pp. 49-66.

The CCK-A receptor is located predominately in the periphery, including pancreatic acinar cells, pyloric sphincter, gall bladder, and vagal afferents, where it mediates pancreatic exocrine secretion, gastric emptying and gall bladder contraction, and transmits post-prandial satiety signals to the CNS. In addition, the CCK-A receptor is found in discrete regions within the CNS, including the nucleus tractus solatarius, area postrema, and the dorsal medial hypothalamus. The CCK-B receptor is located predominately in the CNS, and is less predominant in the periphery.

A number of studies suggest that CCK mediates its satiety effect through the CCK-A receptor, which relays the post-prandial satiety signal via the vagal afferents to the CNS. See, e.g., G. P. Smith et al., *Science* 213 (1981) pp. 1036-1037; and J. N. Crawley et al., *J. Pharmacol. Exp. Ther.*, 257 (1991) pp. 1076-1080. For example, it has been reported that CCK and CCK agonists can decrease food intake in animals, including rats (see, e.g., J. Gibbs, R. C. Young and G. P. Smith, 1973, J. Comp. Physiol. Psychol. 84:488-95), dogs and primates (including man) (see, e.g., B. A. Himick and R. E. Peter, 1994, Am. J. Physiol. 267:R841-R851; Y. Hirosue et al., 1993, Am. J. Physiol. 265:R481-R486; and K. E. Asin et al., 1992, Pharmacol. Biochem. Behav. 42:699-704), and that this anorectic effect is mediated via the CCK-A receptor located on vagal afferent fibers (see, e.g., C. T. Dourish, 1992, In *Multiple cholecystokinin receptors in the CNS*, C. T. Dourish, S. J. Cooper, S. D. Iversen and L. L. Iversen, editors, Oxford University Press, New York, N.Y., pp. 234-253; G. P. Smith and J. Gibbs, 1992, In *Multiple cholecystokinin receptors in the CNS*, C. T. Dourish, S. J. Cooper, S. D. Iversen and L. L. Iversen, editors, Oxford University Press, New York, N.Y., pp. 166-182; J. N. Crawley and R. L. Corwin, 1994, Peptides, 15:731-755; and G. P. Smith et al., 1981, *Science* 213, pp. 1036-1037).

Other lines of evidence supporting the involvement of the CCK-A receptor in regulating food intake include the finding that OLETF rats (which lack the CCK-A receptor) are insensitive to the anorexigenic action of CCK. Also, it has been reported that CCK-A selective antagonists, but not CCK-B antagonists, block the anorectic actions of CCK and CCK analogs and increase feeding in animals (see, e.g., G. Hewson et al., 1988, Br. J. Pharmacol. 93:79-84; R. D. Reidelberger and M. F. O'Rourke, 1989, Am. J. Physiol. 257: R1512-R1518; T. H. Moran et al., 1993, Am. J. Physiol. 265:R620-R624; and M. Covasa and R. C. Ritter, Peptides (New York, N.Y., US) (2001), 22 (8), 1339-1348), including humans (see, e.g., O. M. Wolkowitz et al., 1990, Biol. Psychiatry, 28:169-173.

Finally, it has been reported that infusion of CCK or selective CCK-A agonists reduces meal size and caloric intake in animals, including humans (see, e.g., L. Degen et al., Peptides (New York, N.Y.) (2001), 22 (8), 1265-1269; H. R. Kissileff et al., *Am J Clin Nutr* 34 (1981), pp. 154-160; A. Ballinger et al., *Clin Sci* 89 (1995), 375-381; and R. J. Lieverse et al., *Gastroenterology* 106 (1994), 1451-1454.

The development of non-peptidic CCK-A agonists has been reported in the literature. For example, Sanofi has reported in U.S. Pat. No. 5,798,353 that certain 3-acylamino-5-(polysubstituted phenyl)-1,4 benzodiazepin-2-ones act as CCK-A agonists. Certain 1,5-benzodiazepinones have been reported to be CCK-A agonists having anorectic activity in rodents (see, e.g., E. E. Sugg et al., (1998) *Pharmaceutical Biotechnology* 11 (Integration of Pharmaceutical Discovery and Development): 507-524). R. G. Sherrill et al., in Bioorganic & Medicinal Chemistry Letters (2001), 11 (9), 1145-1148 disclose certain 1,4-benzodiazepines as being peripheral CCK-A receptor agonists with anorectic activity in rat feeding models. A series of 3-(1H-indazol-3-ylmethyl)-1,5-benzodiazepines is discussed by B. R. Henke et al. in J. Med. Chem. (1997), 40 (17), 2706-2725 and J. Med. Chem. (1996), 39 (14), 2655-2658 as being orally active CCK-A agonists.

Although investigations are ongoing, there still exists a need for a more effective and safe therapeutic treatment for reducing or preventing weight-gain.

SUMMARY

The present invention relates to a compound of Formula (I)

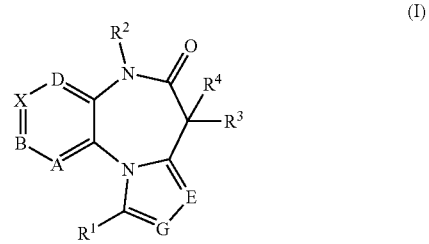

wherein A, B, X, D, E and G are independently —C($R^5$)— or —N—, with the proviso that no more than two of A, B, X and D are N at the same time and at least one of E and G is N;

$R^1$ is selected from the group consisting of ($C_2$-$C_6$)alkyl, halo-substituted($C_1$-$C_6$)alkyl-, ($C_1$-$C_6$)alkylamino-, di($C_1$-$C_6$alkyl)amino-, ($C_1$-$C_6$)alkylamino($C_1$-$C_6$)alkyl-, di($C_1$-

$C_6$)alkylamino($C_1$-$C_6$)alkyl-, aryl, aryl($C_1$-$C_6$)alkyl-, heteroaryl-A, heteroaryl-A($C_1$-$C_6$)alkyl-, a 4- to 7-membered partially or fully saturated heterocycle-A, 4- to 7-membered partially or fully saturated heterocyclyl-A($C_1$-$C_6$)alkyl- and a partially or fully saturated ($C_3$-$C_7$)cycloalkyl($C_1$-$C_6$)alkyl- and, when neither of $R^6$ and $R^7$ is phenylmethyl-, $R^1$ is selected from said group and a partially or fully saturated ($C_3$-$C_7$)cycloalkyl;

where heteroaryl-A is selected from the group consisting of thienyl, thiazolyl, isothiazolyl, indolyl, 2-pyridyl, pyridazinyl, pyrimidyl, oxazolyl, furanyl, imidazolyl, isoxazolyl, quinolinyl, isoquinolinyl, benzothiophenyl, benzofuranyl, pyrazinyl and pyrazolyl, and the partially or fully saturated heterocycle-A is selected from the group consisting of pyranyl, morpholinyl and tetrahydrofuranyl, and where the aryl, heteroaryl-A, partially or fully saturated heterocycle-A or partially or fully saturated cycloalkyl group or portion of a group is optionally substituted with 1 to 3 substituents independently selected from the group consisting of halo, ($C_1$-$C_3$)alkoxy-, halo-substituted($C_1$-$C_3$)alkoxy-, —OH, ($C_1$-$C_3$)alkyl, —CN and halo-substituted ($C_1$-$C_3$)alkyl-;

$R^2$ is —$CH_2C(O)N(R^6)(R^7)$;

one of $R^3$ and $R^4$ is H, halo, ($C_1$-$C_6$)alkyl, ($C_1$-$C_6$)alkoxy- or a partially or fully saturated ($C_3$-$C_7$)cycloalkyl and the other of $R^3$ and $R^4$ is —$C(R^8)(R^9)(R^{10})$; or $R^3$ and $R^4$ are taken together to form =$CHR^{11}$;

each $R^5$ is independently selected from the group consisting of H, ($C_1$-$C_6$)alkoxy-, —OH, halo, —CN, —$NH_2$ and —$NO_2$;

one of $R^6$ and $R^7$ is ($C_3$-$C_6$)alkyl or a partially or fully saturated ($C_3$-$C_7$)cycloalkyl and the other of $R^6$ and $R^7$ is phenyl optionally substituted with 1 to 3 substituents independently selected from the group consisting of —OH, —CN, halo, halo-substituted($C_1$-$C_6$)alkyl-, halo-substituted($C_1$-$C_3$)alkoxy-, ($C_1$-$C_6$)alkyl and ($C_1$-$C_3$)alkoxy-; phenylmethyl- in which the phenyl moiety is optionally substituted with 1 to 3 substituents independently selected from the group consisting of —OH, —CN, halo-substituted($C_1$-$C_6$)alkyl-, halo-substituted($C_1$-$C_3$)alkoxy- and ($C_1$-$C_3$)alkoxy-; or heteroaryl-B optionally substituted with 1 to 3 substituents independently selected from the group consisting of —OH, —CN, halo, halo-substituted($C_1$-$C_6$)alkyl-, halo-substituted($C_1$-$C_3$)alkoxy-, ($C_1$-$C_6$)alkyl and ($C_1$-$C_3$)alkoxy-; and wherein heteroaryl-B is selected from the group consisting of thienyl, thiazolyl, isothiazolyl, isoquinolinyl, quinolinyl, 3- or 4-pyridyl, pyrimidyl, oxazolyl, furanyl, imidazolyl, isoxazolyl, pyrazinyl, pyridazinyl and pyrazolyl;

two of $R^8$, $R^9$ and $R^{10}$ are independently H or ($C_1$-$C_6$) alkyl and the other of $R^8$, $R^9$ and $R^{10}$ is phenyl, a partially or fully saturated ($C_3$-$C_7$)cycloalkyl, heteroaryl-C or a 4- to 7-membered partially or fully saturated heterocycle-B, where heteroaryl-C is selected from the group consisting of indol-2-yl, indol-3-yl, indazol-3-yl, 7-azaindol-2-yl and 7-azaindol-3-yl; said phenyl, partially or fully saturated cycloalkyl, heteroaryl-C or partially or fully saturated heterocycle-B is optionally substituted on carbon atom(s) with 1 to 3 substituents independently selected from the group consisting of ($C_1$-$C_6$)alkoxy-, F, Cl, —CN, —OH, —$CO_2H$, tetrazole and halo-substituted($C_1$-$C_6$)alkoxy-; and $R^{11}$ is phenyl, a partially or fully saturated ($C_3$-$C_7$)cycloalkyl, heteroaryl-C or a 4- to 7-membered partially or fully saturated heterocycle-B, where heteroaryl-C is selected from the group consisting of indol-2-yl, indol-3-yl, indazol-3-yl, 7-azaindol-2-yl and 7-azaindol-3-yl; said phenyl, partially or fully saturated cycloalkyl, heteroaryl-C or partially or fully saturated heterocycle-B is optionally substituted on carbon atom(s) with 1 to 3 substituents independently selected from the group consisting of ($C_1$-$C_6$)alkoxy-, F, Cl, —CN, —OH, —$CO_2H$, tetrazole and halo-substituted($C_1$-$C_6$)alkoxy-;

a pharmaceutically acceptable salt thereof or a prodrug of said compound or said salt.

In one aspect of the invention, one of A, B, X and D in Formula (I) is —N— and the others of A, B, X and D are —$C(R^5)$—. In a further aspect, two of A, B, X and D are —N— and the others of A, B, X and D are —$C(R^5)$—. In a preferred embodiment, each of A, B, X and D in Formula (I) is —$C(R^5)$—, as depicted in Formula (II) below.

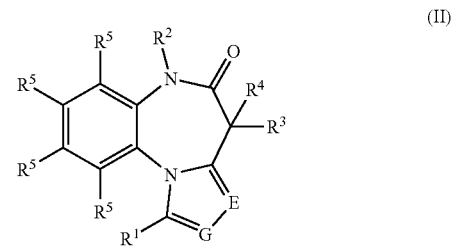

(II)

Each of the substituents $R^1$, $R^2$, $R^3$, $R^4$ and $R^5$ and each of the ring atoms E and G for the compounds of Formula (II) is as defined above and below, generally and preferably, for the compounds of Formula (I).

In one embodiment of the invention, E is —N— and G is —$C(R^5)$— in Formula (I). In another embodiment, E is —$C(R^5)$— and G is —N—. Preferably, each of E and G is —N—. The substituents and other paramenters for these embodiments are as defined above and below, generally and preferably, for the compounds of Formula (I).

A preferred embodiment of the invention pertains to the compounds of Formula (I) in which A and D are —CH—, X and B are —$C(R^5)$— and E and G are —N— as depicted in Formula (III) below. Each of the substituents in Formula (III) is as defined above and below, generally and preferably, for the compounds of Formula (I).

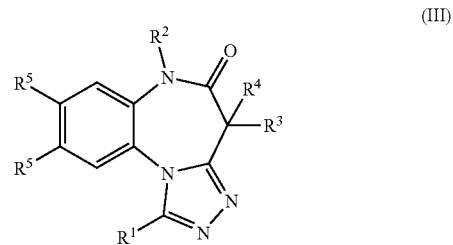

(III)

$R^1$ in Formula (I) is preferably selected from the group consisting of ($C_2$-$C_6$)alkyl, —$CF_3$, phenyl, phenyl($C_1$-$C_3$)alkyl-, heteroaryl-A, heteroaryl-A($C_1$-$C_3$)alkyl-, a 4- to 7-membered partially or fully saturated heterocycle-A, a 4- to 7-membered partially or fully saturated heterocyclyl-A ($C_1$-$C_3$)alkyl- and a partially or fully saturated ($C_3$-$C_7$) cycloalkyl($C_1$-$C_3$)alkyl- and, when neither of $R^6$ and $R^7$ is phenylmethyl-, $R^1$ is also preferably a partially or fully saturated ($C_3$-$C_7$)cycloalkyl. More prefereably, $R^1$ is phenyl or 2-pyridyl or, when neither of $R^6$ and $R^7$ is phenylmethyl-, $R^1$ is also more preferably a partially or fully saturated $(C_5-C_7)$cycloalkyl. Still more preferably, $R^1$ is phenyl, or cyclohexyl when neither of $R^6$ and $R^7$ is phenylmethyl-. Most preferably, $R^1$ is phenyl.

The $R^1$ heteroaryl-A is preferably selected from the group consisting of thienyl, 2-pyridyl, pyridazinyl, pyrimidyl, pyrazinyl and pyrazolyl. More preferably, it will be a 2-pyridyl group.

The $R^1$ aryl, heteroaryl-A, partially or fully saturated heterocycle-A or partially or fully saturated cycloalkyl group or portion of a group is optionally substituted, preferably with 1 to 3 independently selected substituents preferably selected from the group consisting of F, Cl, $(C_1-C_3)$alkoxy-, —OH, $(C_1-C_3)$alkyl, —CN and —$CF_3$; more preferably, from the group consisting of F, Cl, $(C_1-C_3)$alkoxy-, —OH, $(C_1-C_3)$alkyl, and —$CF_3$; especially from the group consisting of F, Cl, $(C_1-C_3)$alkoxy-, —OH and —$(C_1-C_3)$alkyl. When $R^1$ is phenyl it is most preferably unsubstituted, but if substituted it is most preferably substituted with 1 to 3 F atoms or a —OH group.

Each $R^5$ in Formula (I), independently, is preferably selected from the group consisting of H, $(C_1-C_4)$alkoxy-, —OH, F, Cl and —CN; more preferably, from the group consisting of H, —OH and F; still more preferably, from H and F. Most preferably, each $R^5$ is H.

When each of A, B, X, and D in Formula (I) is —$C(R^5)$—, preferably at least one of such $R^5$ is H, more preferably at least two or three of such $R^5$ are H. Most preferably, each of such $R^5$ is H.

When one of E and G in Formula (I) is —$C(R^5)$—, such $R^5$ is also most preferably H.

Preferably one of $R^6$ and $R^7$ in Formula (I) is a branched-chain $(C_3-C_6)$alkyl; more preferably, a branched-chain $(C_3-C_5)$alkyl; still more preferably, a branched-chain $(C_3$ or $C_4)$alkyl; and most preferably, isopropyl.

The other of $R^6$ and $R^7$ in Formula (I) is preferably phenyl, phenylmethyl- or heteroaryl-B in which the phenyl group, the phenyl portion of the phenylmethyl group or the heteroaryl-B group is optionally substituted.

Preferably, the $R^6$ or $R^7$ phenyl group is optionally substituted with 1 to 3 substituents independently selected from the group consisting of —OH, —CN, F, Cl, F- or Cl-substituted$(C_1-C_3)$alkyl-, F- or Cl-substituted$(C_1-C_3)$alkoxy-, $(C_1-C_4)$alkyl and $(C_1-C_3)$alkoxy-. More preferably, the phenyl group is optionally substituted with 1 to 3 substituents independently selected from the group consisting of —OH, —CN, F, Cl, F-substituted$(C_1-C_3)$alkyl-, F-substituted$(C_1-C_3)$alkoxy-, $(C_1-C_4)$alkyl and $(C_1-C_3)$alkoxy-. Still more preferably, the phenyl group is optionally substituted with 1 to 3 substituents independently selected from the group consisting of —OH, F, Cl, —$CF_3$, —$OCF_3$, $(C_1-C_4)$alkyl and $(C_1-C_3)$alkoxy-. Still more preferably, the phenyl group is optionally substituted with 1 or 2 substituents independently selected from the group consisting of F, Cl, —$CF_3$, —$OCF_3$, —$CH_3$ and $(C_1-C_3)$alkoxy-. Still more preferably, the phenyl group is optionally substituted with 1 or 2 F atoms. When one of $R^6$ and $R^7$ is an optionally substituted phenyl group, it is preferably unsubstituted phenyl or 4-F-phenyl.

Preferably, the phenyl moiety of the $R^6$ or $R^7$ phenylmethyl group is optionally substituted with 1 to 3 substituents independently selected from the group consisting of —OH, —CN, and $(C_1-C_3)$alkoxy-. More preferably, the phenyl moiety is optionally substituted with 1 or 2 substituents independently selected from the group consisting of —OH and —$OCH_3$. Most preferably, the phenyl moiety of the phenylmethyl group is unsubstituted.

Preferably, the $R^6$ or $R^7$ heteroaryl-B group is optionally substituted with 1 to 3 substituents independently selected from the group consisting of —OH, —CN, F, Cl, F- or Cl-substituted$(C_1-C_3)$alkyl-, F- or Cl-substituted$(C_1-C_3)$alkoxy-, $(C_1-C_4)$alkyl and $(C_1-C_3)$alkoxy-. More preferably, the heteroaryl-B group is optionally substituted with 1 to 3 substituents independently selected from the group consisting of —OH, —CN, F, Cl, F-substituted$(C_1-C_3)$alkyl-, F-substituted$(C_1-C_3)$alkoxy-, $(C_1-C_4)$alkyl and $(C_1-C_3)$alkoxy-. Still more preferably, the heteroaryl-B group is optionally substituted with 1 to 3 substituents independently selected from the group consisting of —OH, F, Cl, —$CF_3$, —$OCF_3$, $(C_1-C_4)$alkyl and $(C_1-C_3)$alkoxy-. Still more preferably, it is optionally substituted with 1 or 2 substituents independently selected from the group consisting of F, Cl, —$CF_3$, —$OCF_3$, —$CH_3$ and $(C_1-C_3)$alkoxy-. Still more preferably, the heteroaryl-B group is optionally substituted with 1 or 2 substituents independently selected from the group consisting of F, Cl and $(C_1-C_3)$alkoxy-. Still more preferably, the heteroaryl-B is optionally substituted with 1 or 2 substituents independently selected from the group consisting of Cl, —$OCH_3$ and —$OCH_2CH_3$. In a particularly preferred embodiment the hereroaryl-B is substituted with one substituent selected from a group described above, generally or preferably, particularly —$OCH_3$.

The $R^6$ or $R^7$ heteroaryl-B is preferably selected from the group consisting of thienyl, 3- or 4-pyridyl, pyrimidyl, and pyrazinyl. More preferably, it will be a 3- or 4-pyridyl group, particularly a 3-pyridyl group, which may be unsubstituted or, preferably, substituted as described above. When the 3-pyridyl group is monosubstituted, it is preferably substituted at C-6. In a particularly preferred embodiment the heteroaryl group is 6-methoxypyrid-3-yl.

In a preferred embodiment, one of $R^3$ and $R^4$ in Formula (I) is H, $(C_1-C_3)$alkyl or $(C_1-C_3)$alkoxy-; more preferably, H or $(C_1-C_3)$alkyl, e.g., —$CH_3$; most preferably, H. The other of $R^3$ and $R^4$ in Formula (I) is —$C(R^8)(R^9)(R^{10})$.

For —$C(R^8)(R^9)(R^{10})$ in the compounds of Formula (I), two of $R^8$, $R^9$ and $R^{10}$ are prefreably H an the other of $R^8$, $R^9$ and $R^{10}$ is a heteroaryl-C group. Preferably, heteroaryl-C is selected from the group consisting of indol-3-yl, indazol-3-yl and 7-azaindol-3-yl. More referably, heteroaryl-C is an indol-3-yl or indazol-3-yl group; most preferably, an indol-3-yl group. The heteroaryl-C group is optionally substituted on carbon atom(s), preferably located on the phenyl or pyridyl ring of the heteroaryl-C group, with 1 to 3 substituents; preferably, 1 or 2 substituents; more preferably, 1 substituent. The substituents are independently selected, preferably from the group consisting of $(C_1-C_3)$alkoxy-, F, Cl, —CN, —OH, —$CO_2H$, tetrazole and F-substituted$(C_1-C_3)$alkoxy- (e.g., —$OCF_3$); more preferably, from F and Cl. Still more preferably, the heteroaryl-C group is optionally substituted with 1 or 2 or 3 (preferably 1) F atoms. Most preferably, the heteroaryl is unsubstituted.

In an alternative embodiment $R^3$ and $R^4$ are taken together to form =$CHR^{11}$. In this embodiment, where $R^3$ and $R^4$ in Formula (I) are taken together, $R^{11}$ is the same as the "other" of $R^8$, $R^9$ and $R^{10}$ as defined above and below, generally and preferably.

A preferred embodiment of the invention is shown in Formula (IV)

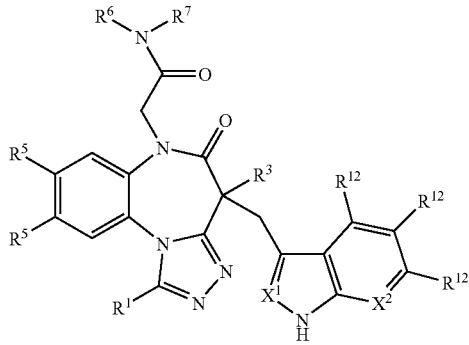

in which $X^1$ is —CH— and $X^2$ is —N— or —C($R^{12}$)—, or $X^1$ is —N— and $X^2$ is —C($R^{12}$)—. Preferably, $X^1$ is —CH— or —N— and $X^2$ is —C($R^{12}$)—. Each $R^{12}$, independently, is preferably selected from the group consisting of H, ($C_1$-$C_3$)alkoxy-, F, Cl, —CN, —OH, —$CO_2$H, tetrazole and F-substituted($C_1$-$C_3$)alkoxy- (e.g., —$OCF_3$); more preferably, from H, F and Cl; still more preferably, from H and F; provided, however, that no more than three of $R^{12}$ are other than H. Most preferably, each $R^{12}$ is H. The other substituents and parameters in Formula (IV) are as defined above and below, generally and preferably.

Formula (V), in which the substituents and other parameters are as defined above, generally and preferably, represents a preferred subgenus of Formula (IV).

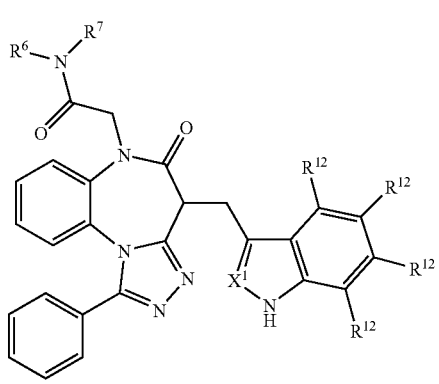

Preferred compounds of the present invention include:

2-[4-(6-fluoro-1H-indol-3-ylmethyl)-5-oxo-1-phenyl-4,5-dihydro-2,3,6,10b-tetraaza-benzo[e]azulen-6yl]-N-isopropyl-N-(6-methoxy-pyridin-3-yl)-acetamide, 2-[4-(1H-indol-3-ylmethyl)-5-oxo-1-phenyl-4,5-dihydro-2,3,6,10b-tetraaza-benzo[e]azulen-6-yl]-N-isopropyl-N-(6-methoxy-pyridin-3-yl)-acetamide, 2-[4-(5-fluoro-1H-indol-3-ylmethyl)-5-oxo-1-phenyl-4,5-dihydro-2,3,6,10b-tetraaza-benzo[e]azulen-6-yl]-N-isopropyl-N-(6-methoxy-pyridin-3-yl)-acetamide, 2-[1-cyclohexyl-4-(1H-indol-3-ylmethyl)-5-oxo-4,5-dihydro-2,3,6,10b-tetraaza-benzo[e]azulen-6-yl]-N-isopropyl-N-(6-methoxy-pyridin-3-yl)-acetamide, 2-[1-(3-hydroxy-phenyl)-4-(1H-indol-3-ylmethyl)-5-oxo-4,5-dihydro-2,3,6,10b-tetraaza-benzo[e]azulen-6-yl]-N-isopropyl-N-(6-methoxy-pyridin-3-yl)-acetamide, N-benzyl-2-[8,9-difluoro-4-(5-fluoro-1H-indol-3-ylmethyl)-5-oxo-1-phenyl-4,5-dihydro-2,3,6,10b-tetraaza-benzo[e]azulen-6-yl]-N-isopropyl-acetamide, 2-[1-(3-hydroxy-phenyl)-4-(1H-indol-3-ylmethyl)-5-oxo-4,5-dihydro-2,3,6,10b-tetraaza-benzo[e]azulen-6-yl]-N-isopropyl-N-phenyl-acetamide, N-benzyl-2-[8,9-difluoro-4-(1H-indol-3-ylmethyl)-5-oxo-1-phenyl-4,5-dihydro-2,3,6,10b-tetraaza-benzo[e]azulen-6-yl]-N-isopropyl-acetamide, N-benzyl-2-[8,9-difluoro-4-(6-fluoro-1H-indol-3-ylmethyl)-5-oxo-1-phenyl-4,5-dihydro-2,3,6,10b-tetraaza-benzo[e]azulen-6-yl]-N-isopropyl-acetamide, N-isopropyl-2-[5-oxo-1-phenyl-4-(1H-pyrrolo[2,3-b]pyridin-3-ylmethyl)-4,5-dihydro-2,3,6,10b-tetraaza-benzo[e]azulen-6-yl]-N-phenyl-acetamide, N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide, N-(6-chloro-pyridin-3-yl)-2-[4-(1H-indol-3-ylmethyl)-5-oxo-1-phenyl-4,5-dihydro-2,3,6,10b-tetraaza-benzo[e]azulen-6-yl]-N-isopropyl-acetamide, N-(6-ethoxy-pyridin-3-yl)-2-[4-(1H-indol-3-ylmethyl)-5-oxo-1-phenyl-4,5-dihydro-2,3,6,10b-tetraaza-benzo[e]azulen-6-yl]-N-isopropyl-acetamide, 2-[4-(1H-indazol-3-ylmethyl)-5-oxo-1-phenyl-4,5-dihydro-2,3,6,10b-tetraaza-benzo[e]azulen-6-yl]-N-isopropyl-N-(6-methoxy-pyridin-3-yl)-acetamide, 2-[4-(1H-indazol-3-ylmethyl)-5-oxo-1-phenyl-4,5-dihydro-2,3,6,10b-tetraaza-benzo[e]azulen-6-yl]-N-isopropyl-N-phenyl-acetamide, 2-[4-(1H-indazol-3-ylmethyl)-5-oxo-1-phenyl-4,5-dihydro-2,3,6,10b-tetraaza-benzo[e]azulen-6-yl]-N-isopropyl-N-phenyl-acetamide, N-benzyl-2-[8,9-difluoro-4-(1H-indazol-3-ylmethyl)-5-oxo-1-phenyl-4,5-dihydro-2,3,6,10b-tetraaza-benzo[e]azulen-6-yl]-N-isopropyl-acetamide, N-benzyl-2-[4-(1H-indazol-3-ylmethyl)-5-oxo-1-phenyl-4,5-dihydro-2,3,6,10b-tetraaza-benzo[e]azulen-6-yl]-N-isopropyl-acetamide, 2-[4-(1H-indol-3-ylmethyl)-4-methyl-5-oxo-1-phenyl-4,5-dihydro-2,3,6,10b-tetraaza-benzo[e]azulen-6-yl]-N-isopropyl-N-phenyl-acetamide, 2-[1-(2-fluoro-phenyl)-4-(1H-indazol-3-ylmethyl)-5-oxo-4,5-dihydro-2,3,6,10b-tetraaza-benzo[e]azulen-6-yl]-N-isopropyl-N-phenyl-acetamide, 2-[1-(3-fluoro-phenyl)-4-(1H-indazol-3-ylmethyl)-5-oxo-4,5-dihydro-2,3,6,10b-tetraaza-benzo[e]azulen-6-yl]-N-isopropyl-N-phenyl-acetamide, 2-[1-cyclohexyl-4-(1H-indazol-3-ylmethyl)-5-oxo-4,5-dihydro-2,3,6,10b-tetraaza-benzo[e]azulen-6-yl]-N-isopropyl-N-phenyl-acetamide, 2-[1-(4-fluoro-phenyl)-4-(1H-indazol-3-ylmethyl)-5-oxo-4,5-dihydro-2,3,6,10b-tetraaza-benzo[e]azulen-6-yl]-N-isopropyl-N-phenyl-acetamide, N-(4-fluoro-phenyl)-2-[4-(1H-indazol-3-ylmethyl)-5-oxo-1-phenyl-4,5-dihydro-2,3,6,10b-tetraaza-benzo[e]azulen-6-yl]-N-isopropyl-acetamide, 2-[4-(1H-indol-3-ylmethyl)-5-oxo-1-phenyl-4,5-dihydro-2, 3,6,10b-tetraaza-benzo[e]azulen-6-yl]-N-isopropyl-N-phenyl-acetamide,
2-[4-(1H-indol-3-ylmethyl)-5-oxo-1-phenyl-4,5-dihydro-2, 3,6,10b-tetraaza-benzo[e]azulen-6-yl]-N-isopropyl-N-phenyl-acetamide,
2-[1-cyclohexyl-4-(1H-indol-3-ylmethyl)-5-oxo-4,5-dihydro-2,3,6,10b-tetraaza-benzo[e]azulen-6-yl]-N-isopropyl-N-phenyl-acetamide,
2-[1-(2-fluoro-phenyl)-4-(1H-indol-3-ylmethyl)-5-oxo-4,5-dihydro-2,3,6,10b-tetraaza-benzo[e]azulen-6-yl]-N-isopropyl-N-phenyl-acetamide, and
2-[4-(1H-indol-3-ylmethylene)-5-oxo-1-phenyl-4,5-dihydro-2,3,6,10b-tetraaza-benzo[e]azulen-6-yl]-N-isopropyl-N-phenyl-acetamide; or a pharmaceutically acceptable salt thereof.

A subset of such preferred compounds includes:
2-[4-(1H-indol-3-ylmethyl)-5-oxo-1-phenyl-4,5-dihydro-2, 3,6,10b-tetraaza-benzo[e]azulen-6-yl]-N-isopropyl-N-phenyl-acetamide;
N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide;
N-benzyl-2-[4-(1H-indazol-3-ylmethyl)-5-oxo-1-phenyl-4,5-dihydro-2,3,6,10b-tetraaza-benzo[e]azulen-6-yl]-N-isopropyl-acetamide; and
2-[4-(1H-indazol-3-ylmethyl)-5-oxo-1-phenyl-4,5-dihydro-2,3,6,10b-tetraaza-benzo[e]azulen-6-yl]-N-isopropyl-N-phenyl-acetamide;
2-[4-(1H-indol-3-ylmethyl)-5-oxo-1-phenyl-4,5-dihydro-2, 3,6,10b-tetraaza-benzo[e]azulen-6-yl]-N-isopropyl-N-(6-methoxy-pyridin-3-yl)-acetamide; or a pharmaceutically acceptable salt thereof.

A further subset of such preferred compounds includes the enantiomers:
(−) 2-[4-(1H-indol-3-ylmethyl)-5-oxo-1-phenyl-4,5-dihydro-2,3,6,10b-tetraaza-benzo[e]azulen-6-yl]-N-isopropyl-N-phenyl-acetamide;
(−) N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide;
(−) N-benzyl-2-[4-(1H-indazol-3-ylmethyl)-5-oxo-1-phenyl-4,5-dihydro-2,3,6,10b-tetraaza-benzo[e]azulen-6-yl]-N-isopropyl-acetamide; and
(−) 2-[4-(1H-indazol-3-ylmethyl)-5-oxo-1-phenyl-4,5-dihydro-2,3,6,10b-tetraaza-benzo[e]azulen-6-yl]-N-isopropyl-N-phenyl-acetamide;
(−) 2-[4-(1H-indol-3-ylmethyl)-5-oxo-1-phenyl-4,5-dihydro-2,3,6,10b-tetraaza-benzo[e]azulen-6-yl]-N-isopropyl-N-6-methoxy-pyridin-3-yl)-acetamide; or a pharmaceutically acceptable salt thereof.

Another aspect of the invention pertains to intermediates of Formula (D) or Formula (F-1) or salts thereof which are intermediates useful in the preparation of the compounds of Formula (I).

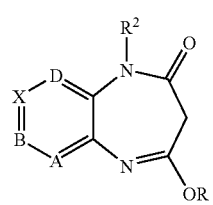

(D)

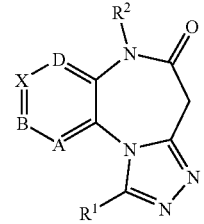

(F-1)

A, B, X, D, $R^1$ and $R^2$ are as defined above for the compounds of Formula (I), generally and preferably.

R is $(C_1-C_6)$alkyl or $(C_3-C_6)$cycloalkyl; preferably, $(C_1-C_4)$alkyl; more preferably, straight chain $(C_1-C_4)$alkyl such as —CH$_3$ or —CH$_2$CH$_3$.

Formula (D-1), wherein R is as defined above for Formula (D) and $R^7$ is as defined above for the compounds of Formula (I), generally and preferably, represents a preferred subgenus of Formula (D).

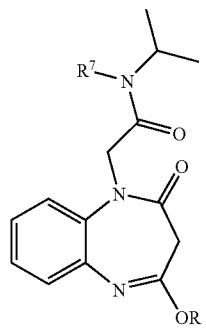

(D-1)

Formula (F-1a), wherein $R^7$ is as defined above for the compounds of Formula (I), generally and preferably, represents a preferred subgenus of Formula (F-1).

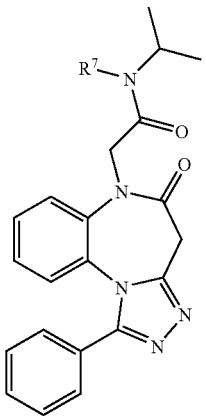

(F-1a)

A further aspect of the present invention relates to a process for the preparation of a compound of Formula (C)

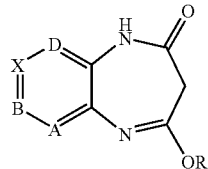
(C)

which comprises contacting a compound of Formula (A) with a compound of Formula (B) in the presence of an acid catalyst, where A, B, X and D are as defined above for Formula (I), generally and preferably. Each R is independently $(C_1-C_6)$alkyl or $(C_3-C_6)$cycloalkyl; preferably, $(C_1-C_4)$alkyl; more preferably, straight chain $(C_1-C_4)$alkyl such as —$CH_3$ or —$CH_2CH_3$.

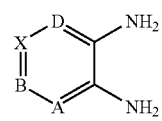
(A)

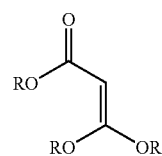
(B)

The acid catalyst may be an inorganic acid, e.g., hydrochloric acid or sulfuric acid; an organic sulfonic acid, e.g., benzene sulfonic acid or para-toluene sulfonic acid; or a carboxylic acid, e.g., acetic acid. Acetic acid is a preferred catalyst.

The process will usually be conducted in the presence of a solvent, preferably an aprotic solvent such as DMF, acetone, methyl ethyl ketone, ethyl acetate, methylene chloride, chloroform, dioxane, THF, toluene or xylenes. More preferably, the solvent is a hydrocarbon solvent such as toluene or xylene(s); especially xylene(s).

The process may be conducted at ambient temperature such as about 25° C. or at an elevated a temperature, generally in the range of about 50° C. to reflux, with the preferred range being up to about 150° C. or 200° C.

The process may be conducted at atmospheric pressure or under positive pressure, for example up to 10, 20, 30, 40 or 50 atmospheres.

In a preferred, laboratory scale embodiment a solution of the compound of Formula (B) in an aprotic solvent is added to a heated solution of the compound of Formula (A) and the acid catalyst in an aprotic solvent in a reaction vessel and the whole is heated at an elevated temperature, as more particularly described in Preparations (3A) and (3B) in the Examples section.

The product (C), under preferred conditions, may be isolated from the reaction mixture simply by filtration.

Also provided is a process for the preparation of a compound of Formula (D), a compound of Formula (E), a compound of Formula (F-1) or a compound of Formula (I-1)

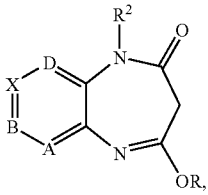
(D)

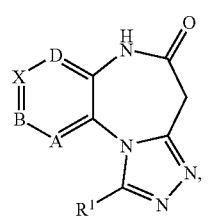
(E)

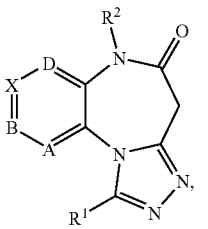
(F-1)

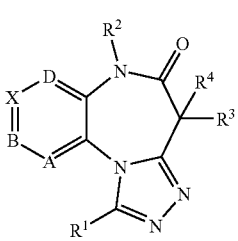
(I-1)

which comprises converting the compound of Formula (C) produced by the process described hereinabove into the compound of Formula (D), the compound of Formula (E), the compound of Formula (F-1) or the compound of Formula (I-1), where A, B, X, D, R, $R^1$, $R^2$, $R^3$ and $R^4$ are as defined above, generally and preferably.

This invention also relates to salts and solvates, including hydrates, of the compounds of the invention. The compounds of the invention and intermediates that are basic in nature are capable of forming a wide variety of salts with various inorganic and organic acids. The acids that may be used to prepare pharmaceutically acceptable acid addition salts of such compounds are those that form non-toxic acid addition salts, i.e. salts containing pharmacologically acceptable anions. Certain of the compounds of the invention and intermediates are acidic in nature and are capable of forming salts with various bases. Sodium and potassium salts are preferred.

The present invention also relates to prodrugs of the present compounds. Compounds of Formula (I) having free carboxy, amino or hydroxy groups can be converted into, for example, esters or amides that act as prodrugs.

In another embodiment of the invention, a pharmaceutical composition is provided which comprises a compound of Formula (I). In a further embodiment the composition also comprises at least one additional pharmaceutical agent, which is preferably an anti-obesity agent. The additional pharmaceutical agent may also be an agent useful in the treatment of a co-morbidity of the primary indication for the composition. The composition preferably comprises a therapeutically effective amount of a compound of Formula (I) or a therapeutically effective amount of a combination of a compound of Formula (I) and an additional pharmaceutical agent. The composition also preferably comprises a pharmaceutically acceptable excipient, diluent or carrier.

Also provided is a method of treating a disease, condition or disorder modulated by a CCK-A receptor agonist in animals, which comprises administering to an animal in need of such treatment a therapeutically effective amount of a compound of Formula (I) or a pharmaceutically acceptable salt thereof, or a solvate or hydrate of said compound or said salt. The compound of Formula (I) may be used alone or in combination with at least one additional pharmaceutical agent, preferably an anti-obesity agent or an agent useful in the treatment of a co-morbidity of the disease, condition or disorder.

Diseases, conditions or disorders modulated by a CCK-A receptor agonist in animals include obesity, overweight and gallstones. Co-morbidities of such diseases, conditions or disorders would likely be incidentally improved.

Accordingly, there is provided a method of treating obesity in an animal, which comprises administering to an animal in need of such treatment a therapeutically effective amount of a compound of Formula (I), a pharmaceutically acceptable salt thereof, or a solvate or hydrate of said compound or said salt. The compound of Formula (I) may be used alone or in combination with at least one additional pharmaceutical agent, preferably an anti-obesity agent.

Also provided is a method of weight management in an animal which comprises administering to the animal a weight-managing amount of a compound of Formula (I), a pharmaceutically acceptable salt thereof, or a solvate or hydrate of said compound or said salt. The compound of Formula (I) may be used alone or in combination with at least one additional pharmaceutical agent, preferably an anti-obesity agent.

The present invention also provides a method of reducing food intake in an animal which comprises administering to the animal a food-intake-reducing amount of a compound of Formula (I), a pharmaceutically acceptable salt thereof, or a solvate or hydrate of said compound or said salt. The compound of Formula (I) may be used alone or in combination with at least one additional pharmaceutical agent, preferably an anti-obesity agent.

Also provided is a method of preventing gallstones in an animal which comprises administering to the animal a gallstone-preventing amount of a compound of Formula (I), a pharmaceutically acceptable salt thereof, or a solvate or hydrate of said compound or said salt. The compound of Formula (I) may be used alone or in combination with at least one additional pharmaceutical agent, preferably an agent useful in the treatment or prevention of gallstones.

A further aspect of the present invention pertains to a pharmaceutical kit for use by a consumer in the treatment of obesity. The kit comprises (a) a suitable dosage form comprising a compound of Formula (I), and (b) instructions describing a method of using the dosage form to treat or prevent obesity.

The invention also relates to combining separate pharmaceutical compositions in kit form. What is provided in this aspect of the invention is a pharmaceutical kit comprising: (a) a first pharmaceutical composition comprising a compound of Formula (I), (b) a second pharmaceutical composition comprising a second compound useful for the treatment of obesity, the prevention of gallstones or the treatment of a co-morbidity of obesity; and (c) a container for containing the first and second compositions. Typically, the kit will also comprise directions for the administration of the separate components. The kit form is especially advantageous when the separate components are preferably administered in different dosage forms or at different dosing intervals.

One example of a kit of the present invention is a so-called blister pack. Blister packs are widely used in the pharmaceutical industry for the packaging of unit disage forms (tablets, capsules and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably, the strength of the sheet is such that the tablets or capsules can be removed from the blister pack by manually applying pressure on the recesses whereby an opening is formed in the sheet at the place of the recess. The tablet or capsule can then be removed via the opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the kit, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of compounds of the present invention can consist of one tablet or capsule while a daily dose of the second compound can consist of several tablets or capsules and vice versa. The memory aid should reflect this.

DEFINITIONS

As used herein, the following terms have the meanings ascribed to them unless otherwise specified.

The term "alkyl" means a straight- or branched-chain hydrocarbon radical of the general formula $C_nH_{2n+1}$. For example, the term "$(C_1-C_6)$alkyl" refers to a monovalent, straight- or branched-chain, saturated aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion of a group, e.g., an alkoxy, acyl, alkylamino, dialkylamino, or alkylthio group, has the same meaning as above. "Halo-substituted alkyl" refers to an alkyl group substituted with one or more halogen atoms (e.g., —$CH_2Cl$, —$CHF_2$, —$CF_3$, —$C_2F_5$, and the like). Likewise, terms such as "F-substituted alkyl" or "Cl-substituted alkyl" mean the alkyl group is substituted with one or more fluorine or chlorine atoms respectively.

The term "acyl" refers to alkyl-, cycloalkyl-, heterocycle-, aryl-, and heteroaryl-substituted carbonyl groups. For example, acyl includes groups such as $(C_1-C_6)$alkanoyl (e.g., formyl, acetyl, propionyl and the like), $(C_3-C_6)$cycloalkylcarbonyl (e.g., cyclopropylcarbonyl, cyclobutylcarbonyl, cyclopentylcarbonyl and the like), heterocyclylcarbonyl (e.g., pyrrolidinylcarbonyl, pyrrolid-2-one-5-carbonyl, piperidinylcarbonyl, piperazinylcarbonyl, tetrahydrofuranylcarbonyl and the like), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.

The term "halo" means F, Cl, Br or I. Preferably, halo will be F, Cl or Br; more preferably, F or Cl.

"Ar" means aryl. The term "aryl" refers to aromatic moieties having a single (e.g., phenyl) or a fused ring system (e.g., naphthalene, anthracene, phenanthrene, etc.). A typical aryl group is a 6- to 10-membered aromatic carbocyclic ring system. Unless stated otherwise, the aryl group may be attached to the chemical entity or moiety by any one of the carbon atoms within the aromatic ring system. The aryl portion (i.e., aromatic moiety) of a group (e.g., arylalkyl) has the same meaning as above.

The term "partially or fully saturated carbocyclic ring" (also referred to as "partially or fully saturated cycloalkyl") refers to nonaromatic rings that are either partially or fully hydrogenated and may exist as a single ring, bicyclic ring or a spiral ring. Unless specified otherwise, the carbocyclic ring is generally a 3- to 8-membered ring (preferably, 3- to 6-membered ring). For example, partially or fully saturated carbocyclic/cycloalkyl rings include groups such as cyclopropyl, cyclopropenyl, cyclobutyl, cyclobutenyl, cyclopentyl, cyclpentenyl, cyclopentadienyl, cyclohexyl, cyclohexenyl, cyclohexadienyl, norbornyl (bicyclo[2.2.1]heptyl), norbornenyl, bicyclo[2.2.2]octyl, and the like. Unless stated otherwise, the carbocyclic group may be attached to the chemical entity or moiety by any one of the carbon atoms within the cycloalkyl ring system. The cycloalkyl portion of a group (e.g., cycloalkylalkyl, cycloalkylamino, etc.) has the same meaning as above.

The term "partially or fully saturated heterocyclic ring" (also referred to as "partially or fully saturated heterocycle" or "partially or fully saturated heterocyclyl") refers to non-aromatic rings that are partially or fully hydrogenated, contain at least one ring heteroatom and may exist as a single ring, bicyclic ring or a spiral ring. Unless specified otherwise, the heterocyclic ring is generally a 4- to 7-membered ring containing 1 to 4 heteroatoms (preferably 1 or 2 heteroatoms) independently selected from sulfur, oxygen or nitrogen. Heterocyclic rings include groups such as epoxy, aziridinyl, pyranyl, tetrahydrofuranyl, pyrrolidinyl, N-methylpyrrolidinyl, imidazolidinyl, piperidinyl, piperazinyl, pyrazolidinyl, morpholino, tetrahydrothienyl, tetrahydrothienyl 1,1-dioxide and the like. Unless stated otherwise, the heterocyclic group may be attached to the chemical entity or moiety by any one of the ring atoms within the heterocyclic ring system. The heterocycle portion of a group (e.g., heterocyclylalkyl) has the same meaning as above.

The term "heteroaryl" refers to aromatic moieties containing at least one heteratom (e.g., oxygen, sulfur, nitrogen or combinations thereof) within a 5- to 10-membered aromatic ring system (e.g., pyridyl, pyrazolyl, indolyl, indazolyl, azaindolyl, thienyl, furanyl, benzofuranyl, oxazolyl, isoxazolyl, imidazolyl, tetrazolyl, pyrimidyl, pyrazinyl, pyridazinyl, thiazolyl, isothiazolyl, quinolinyl, isoquinolinyl, benzothiophenyl, etc.). The heteroaromatic moiety may consist of a single or fused ring system. A typical single heteroaryl ring is a 5- to 6-membered ring containing one to three heteroatoms independently selected from oxygen, sulfur and nitrogen, and a typical fused heteroaryl ring system is a 9- to 10-membered ring system containing one to four heteroatoms independently selected from oxygen, sulfur and nitrogen. Unless stated otherwise, the heteroaryl group may be attached to the chemical entity or moiety by any one of the atoms within the aromatic ring system (e.g., imidazol-1-yl, imidazol-2-yl, imidazol-4-yl, imidazol-5-yl). The heteroaryl portion of a group (e.g., heteroarylalkyl) has the same meaning as above.

The term "solvate" refers to a molecular complex of a compound with one or more solvent molecules. For solvates of the compounds of Formula (I) (including prodrugs and pharmaceutically acceptable salts thereof), the solvent molecules are those commonly used in the pharmaceutical art, which are known to be innocuous to the recipient, e.g., water, ethanol, and the like. The term "hydrate" refers to a solvate in which the solvent molecule is water.

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBz) and 9-fluorenylmethylenoxycarbonyl (Fmoc). Similarly, a "hydroxy-protecting group" refers to a substituent on a hydroxy group that blocks or protects the hydroxy functionality. Suitable hydroxy-protecting groups include acetyl and silyl. A "carboxy-protecting group" refers to a substituent that blocks or protects the carboxy functionality such as an ester group. Common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino) ethyl, nitroethyl and the like. For a general description of protecting groups and their use, see T. W. Greene, Protective Groups in Organic Synthesis, John Wiley & Sons, N.Y., 1991.

The expression "prodrugs" means compounds that are drug precursors, which, following administration, release the drug in vivo via some chemical or physiological process (e.g., a prodrug on being brought to the physiological pH or through enzyme action is converted to the desired drug form).

The phrase "pharmaceutically acceptable" means that the substance or composition is compatible chemically and/or toxicologically with the other ingredients comprising a formulation, and/or the animal being treated therewith.

The phrase "therapeutically effective" is intended to qualify an amount of an agent for use in the therapy of a disease, condition, or disorder which (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The terms "treating", "treat", and "treatment" embrace both preventative, i.e. prophylactic, and palliative treatment.

The term "animal" means humans as well as all other warm-blooded members of the animal kingdom possessed of a homeostatic mechanism, including mammals (e.g., companion animals, zoo animals and food-source animals) and birds. Some examples of companion animals are canines (e.g., dogs), felines (e.g., cats) and horses; some examples of food-source animals are pigs, cows, sheep, poultry and the like. Preferably, the animal is a mammal. Preferably, the mammal is a human, a companion animal or a food-source animal. Most preferably, the animal is a human.

The term "compounds of the present invention", and the like (unless specifically identified otherwise) means the compounds of Formulas (I), as defined above generally and preferably (including all embodiments), prodrugs thereof, pharmaceutically acceptable salts of the compounds and/or prodrugs, and hydrates or solvates of the compounds, salts, and/or prodrugs, as well as all stereoisomers, atropisomers, tautomers and isotopically labeled derivatives of the compounds of Formula (I).

DETAILED DESCRIPTION

In general, the compounds of the present invention can be made by processes described herein or by other processes within the skill of a person having ordinary skill in the medicinal chemistry art, including processes analogous to those described in the art for producing compounds that are similar or analogous to the present compounds or have substituents that are similar to or the same as those of the present compounds. Certain intermediates and processes for the preparation of the present compounds are provided as further features of the present invention and are illustrated by the following reaction schemes. These processes can be carried out in sequential or convergent synthetic routes. Other processes are described in the experimental section. Purification procedures include crystallization and normal phase or reverse phase chromatography.

In the discussion below pertaining to the reaction schemes, certain common abbreviations and acronyms are employed which include: AcOH (acetic acid), DMF (dimethylformamide), DMSO (dimethyl sulfoxide), NH$_4$OAc (ammonium acetate), NMP (N-methylpyrrolidone), OTS (p-toluenesulfonyloxy), Pg (protecting group) and THF (tetrahydrofuran).

Scheme I below illustrates one means of preparing compounds of Formula (I) in which E and G are both —N—. In the structures in Scheme I below, A, B, X, D, R, R$^1$, R$^2$, R$^3$ and R$^4$ are as defined above, generally and preferably.

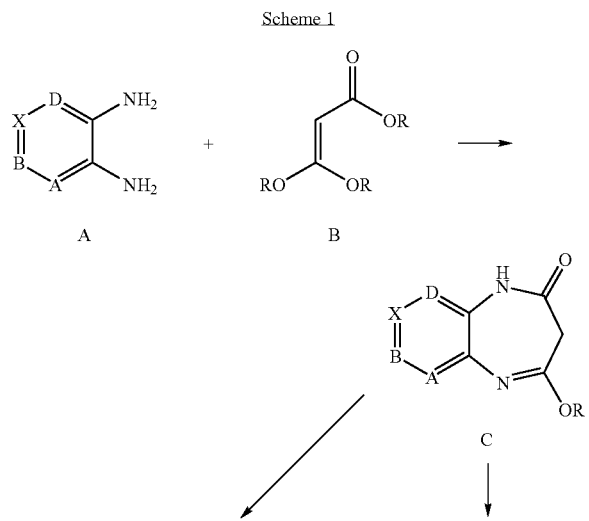

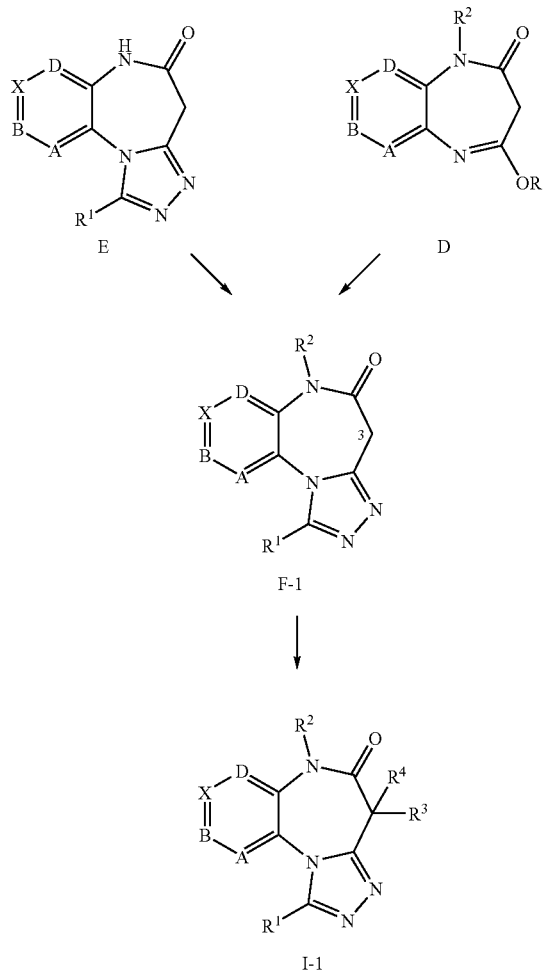

According to Scheme I, the compound of Formula (C) is prepared by coupling a diamine of Formula A with the appropriate bisalkoxy acrylate of Formula (B), such as 3,3-diethoxyacrylic acid ethyl ester, for example by heating the two compounds in a suitable solvent, such as toluene or xylene(s), in the presence of an acid catalyst such as acetic acid. The Formula (A) diamines are commercially available, may be prepared be methods described in the literature, or may be prepared by methods analogous to those described in the literature for analogous compounds or by methods within the skill of a person of ordinary skill in the medicinal chemistry art from readily available starting materials.

The iminoether of Formula (C) is then N-alkylated with an alkylating agent R$^2$L wherein L is a leaving group such as Cl, Br, I or OTs, (e.g., Br as in 2-bromo-N-isopropyl-N-phenyl-acetamide) using an inert solvent such as NMP or DMF and a base such as lithium hexamethyldisilazide or sodium hydride, at a temperature of about −20° C. to about 70° C. for about 2 to about 48 hours, to afford the N-alkylated iminoether of Formula (D).

Alternatively, the compound of Formula (C) is akylated, under the conditions described above, with an alkylating agent L-CH$_2$CO$_2$ Pg (where L is a leaving group and Pg is a protecting group) such a 2-haloacetic acid ester (e.g., benzyl 2-bromoacetate) and the ester protecting group removed to afford the corresponding carboxylic acid, i.e. the compound of Formula (D) wherein R$^2$ is —CH$_2$COOH. The carboxylic acid compound is then coupled with an amine HNR⁶R⁷ using standard amide coupling methods to afford the compound of Formula (D) where R² is —CH₂C(O)N (R⁶)(R⁷). The compound of Formula D where R² is —CH₂C (O)N(R⁶)(R⁷) is then converted to the triazine derivative of Formula (F-1) by condensation of the Formula (D) compound with an acyl hydrazide of the general formula R₁CONHNH₂ in an organic solvent, such as glacial acetic acid or toluene, at a temperature in the range of about 0° C. to reflux.

Alternatively, the compound of Formula (C) is converted to the triazine of Formula (E) under conditions described above for triazine ring formation. The compound of Formula (E) is then N-alkylated to form the compound of Formula (F-1) in the manner described above for the alkylation of the compound of Formula (C).

The compound of Formula (F-1) is alkylated on the C-3 carbon using a suitable electrophile such as (R⁸)(R⁹)(R¹⁰) C-halide or -toslyate (e.g. R³L where R³ is —C(R⁸)(R⁹) (R¹⁰) and L is a leaving group such as Cl, Br, I or OTs), a suitable base such as lithium hexamethyldisilazide or sodium hydride, and an inert solvent, such as DMF, NMP or THF, at a temperature in the range of about −20° C. to about 70° C., to afford the monoalkylated product of Formula (I-1) where R³ is —C(R⁸)(R⁹)(R¹⁰) and R⁴ is H. Repeating this procedure with an appropriate base and an alkylating agent (e.g. R⁴L where R⁴ is alkyl or cycloalkyl and L is a leaving group such as Cl, Br, I or OTs) affords the compound of Formula (I-1) where R³ is —C(R⁸)(R⁹)(R¹⁰) and R⁴ is alkyl or cycloalkyl. Compounds in which one of R³ and R⁴ is halo may be prepared by similarly forming an anion at C-3 with a strong base, such as lithium hexamethyldisilazide or sodium hydride, in an inert solvent, such as DMF, NMP or THF, at a temperature in the range of about −78° C. to room temperature, and subsequently trapping the anion with a suitable halogenating agent (e.g., Br₂, Cl₂, (diethylamino) sulfur trifluoride (DAST) or 1-(chloromethyl)-4-fluoro-1,4-diazoniabicyclo[2,2,2]octane bis(tetrafluoroborate (Selecf-fluor™, available from Air Products and Chemicals, Inc., 7201 Hamilton Boulevard, Allentown, Pa.)) to obtain the C-3 halogenated compound. Similarly, trapping of the C-3 anion with a suitable oxygenating reagent, such as 2-(phenylsulfonyl)-3-phenyloxaziridine or oxodiperoxymolybdenum(pyridine)(hexamethylphosphoric triamide (MoOPh) affords the C-3 hydroxy compound, which can subsequently be converted to the C-3 alkoxy compound by O-alkylation with an alkyl halide and suitable base under standard conditions.

Alternatively, the compound of Formula (F-1) is condensed with an aldehyde R¹¹CHO, such as indole-3-carboxaldehyde, in an organic solvent such as toluene or xylene(s), preferably in the presence of a base such as piperidine, at a temperature in the range of room temperature to reflux temperature, to afford the corresponding alpha-beta unsaturated intermediate (i.e. where R³ and R⁴ are taken together to form =CHR¹¹), which may be reduced under standard conditions (e.g. Zn—AcOH; H₂, Pd—C) to afford the compound of Formula (I-1) where one of R³ and R⁴ is H and the other of R³ and R⁴ is —CH₂R¹⁰ (R¹¹ is the same as R¹⁰). Scheme II below illustrates one means of preparing compounds of Formula (I) in which E is —N— and G is —C(R⁵)—. In the structures in Scheme II below, A, B, X, D, R, R¹, R², R³, R⁴ and R⁵ are as defined above, generally and preferably.

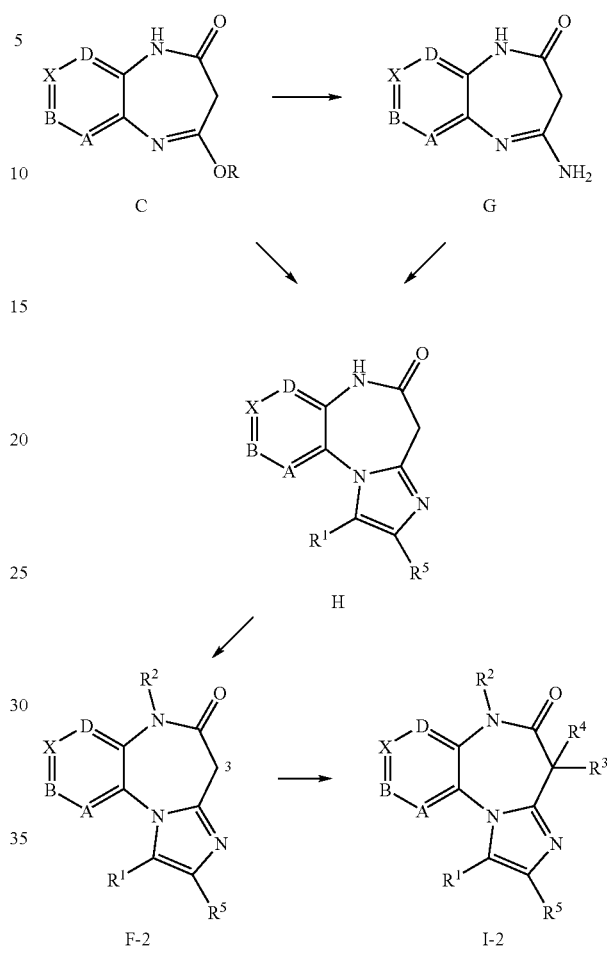

According to Scheme II, the Formula (G) amidine is prepared by treating an iminoether of Formula (C) with NH₃ or an ammonia source (e.g. NH₄OAc). The amidine is then condensed, under standard conditions, with, for example, a bromoketone of the formula R¹CH(Br)C(O)R⁵, to give the imidazole of Formula (H). Alternatively, the iminoether of Formula (C) may be condensed with an alpha-amino ketone of formula H₂NCH(R⁵)C(O)R¹ to afford the imidazole of Formula (H) (see, e.g., M. Langlois et al., J. Heterocycl. Chem. (1982), 19(1), 193-200).

The imidazole of Formula (H) is then subjected to N1-alkylation (i.e. introduction of the R² substituent), using procedures similar to those described above for the N-alkylation of the compound of Formula (C) or (E) in Scheme I, to afford the N-alkylated imidazole of Formula (F-2). This compound is then alkylated at C3, using conditions similar to those outlined for the conversion of the compound of Formula (F-1) to the compound of Formula (I-1) in Scheme I, to provide the compound of Formula (I-2) of Scheme II.

Scheme III below illustrates one means of preparing compounds of Formula (I) in which E is —C(R⁵)— and G is —N—. In the structures in Scheme III below, A, B, X, D, R, R¹, R², R³, R⁴ and R⁵ are as defined above, generally and preferably.

Scheme III

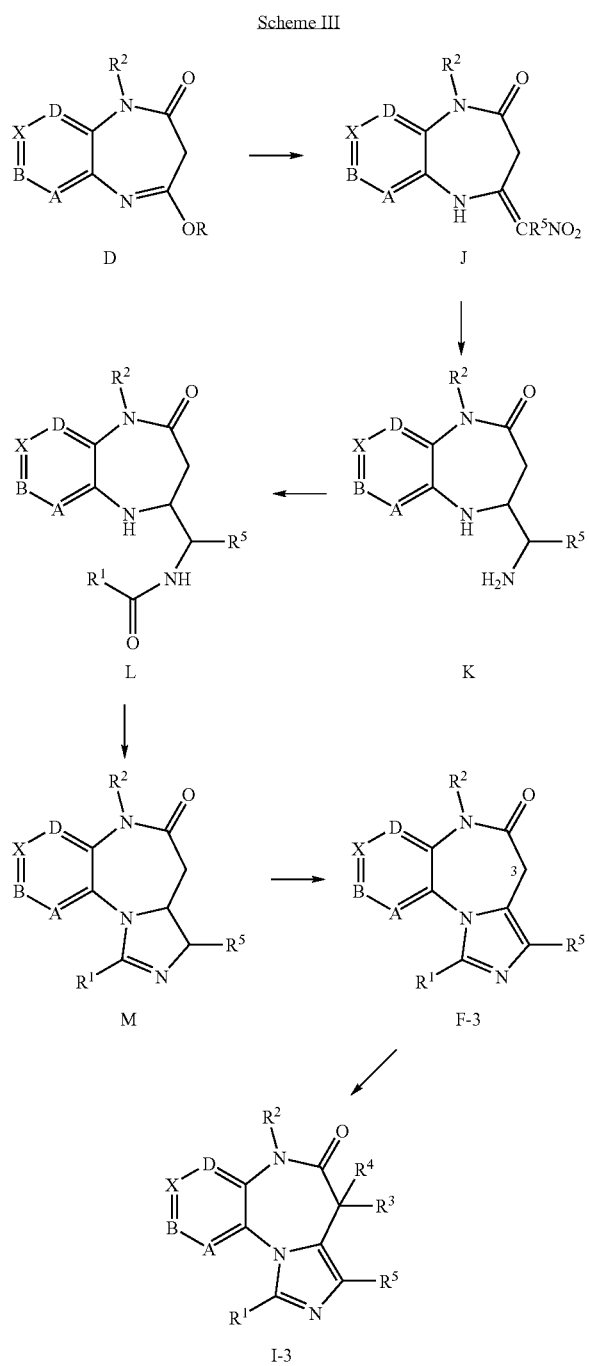

Compounds of Formula (I-3) can be synthesized by methods analogous to those reported in the chemical and patent literature for similar or analogous compounds (see, e.g., "Diazepine derivatives," Neth. Appl., NL 7803585 (1978); Armin Walser, "Imidazodiazepine derivatives," Ger. Offen., DE 2813549 (1978); and Armin Walser and Rodney Ian Fryer, "Imidazo[1,5-a][1,5]benzodiazepines," U.S. Pat. No. 4,080,323 (1978). Thus, the compound of Formula (D) is condensed with an anion of nitroalkane (which can be generated by treating a nitroalkane with a strong base, such as lithium hexamethydisilazide, sodium hydride, potassium-t-butoxide or lithium diisopropylamide, in an aprotic organic solvent, such as THF, DMSO or DMF, for example), at a temperature in the range of about −30° C. to about 100° C. to afford the compound of Formula (J). This compound is subsequently reduced using a metal catalyst, such as palladium, platinum or nickel, in the presence of hydrogen to afford the compound of Formula (K).

The compound of Formula (K) is acylated with a suitable acylating agent for the introduction of $R^1CO-$, e.g., an acyl halide/base or carboxylic acid/coupling agent (e.g. EDCI, N,N-carbonyldiimidazole), to give the compound of Formula (L), which is then subjected to standard dehydrative ring closure conditions to afford the compound of Formula (M). Oxidation of the compound of Formula (M) to give the compound of Formula (F-3) is accomplished using an oxidizer such as manganese dioxide or potassium permanganate. The compound of Formula (F-3) may be converted into the compound of Formula (I-3) in a manner analogous to that described for the conversion of the compound of Formula (F-1) to the compound of Formula (I-1) in Scheme I.

Conventional methods and/or techniques of separation and purification known to one of ordinary skill in the art can be used to isolate the compounds of the present invention, as well as the various intermediates related thereto. Such techniques will be well known to one of ordinary skill in the art and may include, for example, all types of chromatography (high pressure liquid chromatography (HPLC), column chromatography using common adsorbents such as silica gel, and thin-layer chromatography), recrystallization, and differential (i.e., liquid-liquid) extraction techniques.

The compounds of the present invention may be isolated and used per se or in the form of their pharmaceutically acceptable salts, solvates and/or hydrates. The term "salts" includes both inorganic and organic salts. These salts may be prepared in situ during the final isolation and purification of a compound, or by separately reacting the compound with a suitable organic or inorganic acid or base and isolating the salt thus formed. Salts of the intermediates need not be pharmaceutically acceptable.

Representative pharmaceutically acceptable acid addition salts of the present compounds include hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, pamoate, palmitate, malonate, stearate, laurate, malate, borate, hexafluorophosphate, naphthylate, glucoheptonate, lactobionate and laurylsulfonate salts and the like. A preferred salt of the compounds is the hydrochloride salt.

Salts formed with bases include cations based on the alkali and alkaline earth metals, such as sodium, lithium, potassium, calcium, magnesium, and the like, as well as ammonium, quaternary ammonium, and 1°, 2° or 3° amine-derived cations including, but not limited to, ammonium, tetramethylammonium and tetraethylammonium and cations derived from methylamine, ethylamine, dimethylamine, trimethylamine, triethylamine, and the like. See, e.g., Berge, et al., *J. Pharm. Sci.,* 66, 1-19 (1977).

The present invention also includes prodrugs of the compounds of Formula (I). As used herein, the term "prodrug" means a compound that is transformed in vivo to yield a compound of Formula (I) or a pharmaceutically acceptable salt, hydrate or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series; in Bioreversible Carriers in Drug Design, ed. Edward B. Roche, American Pharmaceutical Association and Pergamon Press, 1987; in *Advanced Drug Delivery Reviews*, 1996, 19, 115; and in *J. Med. Chem.* 1996, 39, 10.

For example, if an compound of the present invention contains a carboxylic acid functional group, a prodrug can comprise an ester formed by the replacement of the hydrogen atom of the acid group with a group such as ($C_1$-$C_8$) alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

Similarly, if a compound of the present invention contains an alcohol functional group, a prodrug can be formed by replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N-($C_1$-$C_6$)alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, P(O)(OH)$_2$, P(O)(O($C_1$-$C_6$)alkyl)$_2$ or glycosyl (the radical resulting from the removal of a hydroxyl group of the hemiacetal form of a carbohydrate).

If a compound of the present invention contains an amine functional group, a prodrug can be formed by the replacement of a hydrogen atom in the amine group with a group such as R-carbonyl-; RO-carbonyl-; (R')(R)N-carbonyl-where R and R' are each independently ($C_1$-$C_{10}$)alkyl, ($C_3$-$C_7$)cycloalkyl or benzyl; or R-carbonyl is a natural α-aminoacyl or natural α-aminoacyl-natural α-aminoacyl; —C(OH)C(O)OY' wherein Y' is H, ($C_1$-$C_6$)alkyl or benzyl; —C(OY$^0$)Y$^1$ wherein Y$^0$ is ($C_1$-$C_4$) alkyl and Y$^1$ is ($C_1$-$C_6$) alkyl, carboxy($C_1$-$C_6$)alkyl, amino($C_1$-$C_4$)alkyl or mono-N- or di-N,N-($C_1$-$C_6$)alkylaminoalkyl; or —C(Y$^2$)Y$^3$ wherein Y$^2$ is H or methyl and Y$^3$ is mono-N- or di-N,N-($C_1$-$C_6$) alkylamino, morpholino, piperidin-1-yl or pyrrolidin-1-yl.

Many of the compounds of the present invention and certain intermediates contain one or more asymmetric or chiral centers (e.g., the C-3 carbon atom bearing R$^3$ and R$^4$ in Formula (I)), and such compounds therefore exist in different stereoisomeric forms (e.g., enantiomers and diastereoisomers). Many of the present compounds also exhibit atropism. All stereoisomeric forms of the intermediates and compounds of the present invention as well as mixtures thereof, including racemic and diastereomeric mixtures, which possess properties useful in the treatment of the conditions discussed herein or are intermediates useful in the preparation of compounds having such properties, form a part of the present invention. Generally, one of the enantiomers will be more active biologically than the other enantiomer. However, the less active enantiomer can be converted to a racemic mixture by epimerization at the C-3 stereocenter using a strong base, such as sodium methoxide in methanol for example. The racemic mixture can subsequently be separated into each enantiomer using standard conditions, such as resolution or chiral chromatography In addition, the present invention embraces all geometric isomers and atropisomers. For example, if an intermediate or compound of the present invention contains a double bond or a fused ring, both the cis- and trans-forms, as well as mixtures, are embraced within the scope of the invention.

Diastereomeric mixtures may be separated into their individual diastereoisomers on the basis of their physical chemical differences by methods well known to those skilled in the art, such as by chromatography and/or fractional crystallization. Enantiomers may be separated by use of a chiral HPLC column. They may also be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers.

The compounds of the present invention and intermediates may exist in unsolvated as well as solvated forms with solvents such as water, ethanol, isopropanol and the like, and both solvated and unsolvated forms are included within the scope of the invention. Solvates for use in the methods aspect of the invention should be with pharmaceutically acceptable solvents.

A number of the compounds of the present invention and intermediates therefor exhibit tautomerism and therefore may exist in different tautomeric forms under certain conditions. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is an imidazole moiety where the hydrogen may migrate between the ring nitrogens. Valence tautomers include interconversions by reorganization of some of the bonding electrons. All such tautomeric forms (e.g., all keto-enol and imine-enamine forms) are within the scope of the invention. The depiction of any particular tautomeric form in any of the structural formulas herein is not intended to be limiting with respect to that form, but is meant to be representative of the entire tautomeric set.

The present invention also embraces isotopically labeled compounds which are identical to the compounds of Formula (I) or intermediates therefore but for the fact that one or more atoms are replaced by an atom having an atomic mass or mass number different from the atomic mass or mass number usually found in nature. Examples of isotopes that can be incorporated into the intermediates or compounds of the invention include isotopes of hydrogen, carbon, nitrogen, oxygen, phosphorus, sulfur, fluorine, iodine, and chlorine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{123}$I, $^{125}$I and $^{36}$Cl, respectively. Compounds of the present invention, prodrugs thereof and pharmaceutically acceptable salts, hydrates and solvates of said compounds and of said prodrugs which contain the aforementioned isotopes and/or other isotopes of other atoms are within the scope of the present invention.

Certain isotopically labeled compounds of the present invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability.

Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$., and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein by substituting an isotopically labeled reagent for a non-isotopically labeled reagent.

Compounds of the present invention are useful, for example, for treating diseases, conditions and disorders modulated by cholecystokinin A receptors (e.g., CCK-A receptor agonists). Such diseases, conditions and disorders include obesity and gallstones, as well as non-obese overweight conditions and normal weight conditions where weight control or management is desired in order to prevent an obese or overweight condition from developing, or to just maintain an optimum, healthy weight. Also, the compounds of the present invention are useful in treating or preventing the diseases, conditions and disorders that are clinical sequelae or co-morbidities of obesity such as hypertension, dyslipidemia, type 2 (non-insulin dependent) diabetes, insulin resistance, glucose intolerance, hyperinsulinemia, coronary heart disease, angina pectoris, congestive heart failure, stroke, gallstones, cholescystitis, cholelithiasis, gout, osteoarthritis, obstructive sleep apnea and respiratory problems, gall bladder disease, certain forms of cancer (e.g., endometrial, breast, prostate, and colon) and psychological disorders (such as depression, eating disorders, distorted body image and low self esteem). Additionally, the present compounds are useful in the treatment of any condition in which it is desirable to lose weight or to reduce food intake.

Therefore, the present invention provides methods of treatment or prevention of such diseases, conditions and/or disorders modulated by CCK-A receptor agonists in an animal which comprises administering to the animal in need of such treatment a compound of Formula (I), preferably a therapeutically effective amount thereof.

The present compounds will generally be administered in the form of a pharmaceutical composition. Accordingly, the present invention also provides pharmaceutical compositions comprising a therapeutically effective amount of a compound of Formula (I) in admixture with a pharmaceutically acceptable excipient, diluent or carrier, as well as methods of use of such compositions in the treatment of diseases, conditions and/or disorders that are modulated by CCK-A receptor agonists in an animal, or clinical sequelae or co-morbities thereof, which comprise administering such pharmaceutical composition to an animal in need of such treatment.

The compounds of Formula (I) and compositions containing them are also useful in the manufacture of a medicament for the therapeutic applications mentioned herein.

The compounds of the present invention may be administered to a patient at dosage levels in the range of about 0.1 mg to about 3,000 mg per day. The dosage for a human will generally be in the range of about 1 mg to about 1,000 mg per day; more frequently, from about 1 mg to about 400 mg or 500 mg per day; preferably, from about 1 mg to about 200 mg or 250 mg per day; more preferably, from about 1 mg to about 75 mg or 100 mg per day; typically from about 1 mg to about 50 mg or 60 mg per day. The specific dosage and dosage range that can be used depends on a number of factors, including the age and weight of the patient, the mode of administration, the severity of the disease, condition and/or disorder being treated, and the pharmacological activity of the compound being administered. The determination of dosage ranges and optimal dosages for a particular patient is well within the ordinary skill in the art.

The compounds of this invention may be used in combination with other pharmaceutical agents (sometimes referred to herein as a "combination") for the treatment of the diseases, conditions and/or disorders mentioned herein or co-morbidities thereof. Therefore, methods of treatment that include administering compounds of the present invention in combination with other pharmaceutical agents are also provided by the present invention.

Suitable pharmaceutical agents that may be used in the combination aspect of the present invention include anti-obesity agents such as cannabinoid-1 (CB-1) antagonists (such as rimonabant), 11β-hydroxy steroid dehydrogenase-1 (11β-HSD type 1) inhibitors, peptide YY (PYY) and PYY agonists (such as $PYY_{3-36}$), MCR-4 agonists, monoamine reuptake inhibitors (such as sibutramine), sympathomimetic agents, $β_3$ adrenergic receptor agonists, dopamine receptor agonists (such as bromocriptine), melanocyte-stimulating hormone receptor analogs (such as those discussed in U.S. Pat. No. 6,716,810), 5HT2c receptor agonists, melanin concentrating hormone antagonists, leptin (the OB protein), leptin receptor agonists, galanin antagonists, lipase inhibitors (such as tetrahydrolipstatin, i.e. orlistat), bombesin receptor agonists, neuropeptide-Y (NPY) receptor antagonists (e.g., NPY Y5 receptor antagonists), thyromimetic agents, dehydroepiandrosterone, glucocorticoid receptor agonists or antagonists, orexin receptor antagonists, glucagon-like peptide-1 receptor agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) antagonists, ghrelin receptor antagonists, histamine 3 receptor antagonists or inverse agonists, neuromedin U receptor agonists, MTP/ApoB secretion inhibitors, T-type calcium channel blockers (such as zonisamide), opioid receptor antagonists (such as those discussed in PCT patent application publication Nos. WO 03/101963 and WO 2004/026305) and the like.

Preferred NPY receptor antagonists include NPY Y5 receptor antagonists, such as the spiro compounds described in U.S. Pat. Nos. 6,566,367; 6,649,624; 6,638,942; 6,605,720; 6,495,559; 6,462,053; 6,388,077; 6,335,345 and 6,326,375; U.S. patent application publication Nos. 2002/0151456 and 2003/036652 and PCT patent application publication Nos. WO 03/010175; WO 03/082190 and WO 02/048152. All of the above-recited references are incorporated herein by reference.

Preferred anti-obesity agents include orlistat (U.S. Pat. Nos. 5,274,143; 5,420,305; 5,540,917; and 5,643,874), sibutramine (U.S. Pat. No. 4,929,629), bromocriptine (U.S. Pat. Nos. 3,752,814 and 3,752,888), ephedrine, leptin, pseudoephedrine, zonisamide (U.S. Pat. No. 4,172,896) and peptide $YY_{3-36}$ or an analog or derivative thereof (U.S. patent application publication No. 2002/0141985 and PCT patent application publication No. WO 03/026591. All of the above-recited references are incorporated herein by reference.

The compounds of this invention may also be used in combination with other pharmaceutical agents (e.g., LDL-cholesterol lowering agents, triglyceride lowering agents) for the treatment of the disease/conditions mentioned herein. For example, the present compounds may be used in combination with an HMG-CoA reductase inhibitor (such as atorvastatin, simvastatin, fluvastatin, pravastatin, cerivastatin, rosuvastatin or pitavastatin), an HMG-CoA synthase inhibitor, an HMG-CoA reductase gene expression inhibitor, a squalene synthetase/epoxidase/cyclase inhibitor, a cholesterol synthesis inhibitor, a cholesterol absorption inhibitor (such as ezetimibe), a CETP inhibitor (such as torcetrapib), a PPAR modulator or other cholesterol lowering agent such as a fibrate, niacin, an ion-exchange resin, an antioxidant, an ACAT inhibitor (such as avasimibe, CS-505 (Sankyo) and eflucimibe) or a bile acid sequestrant. Other pharmaceutical agents useful in the practice of the combination aspect of the invention include bile acid reuptake inhibitors, ileal bile acid transporter inhibitors, ACC inhibitors, antihypertensive agents (such as Norvasc®), antibiotics, antidiabetics (such as metformin, pfenformin or buformin), PPARγ activators, insulin secretagogues (such as sulfonylureas and glinides), insulin, aldose reductase inhibitors (ARI) (e.g., zopolrestat), sorbitol dehydrogenase inhibitors (SDI)), and anti-inflammatory agents such as aspirin or, preferably, an anti-inflammatory agent that inhibits cyclooxygenase-2 (Cox-2) to a greater extent than it inhibits cyclooxygenase-1 (Cox-1) such as celecoxib (U.S. Pat. No. 5,466,823), valdecoxib (U.S. Pat. No. 5,633,272, parecoxib (U.S. Pat. No. 5,932,598), deracoxib (CAS RN 169590-41-4), rofecoxib ((CAS RN 162011-90-7), etoricoxib (CAS RN 202409-33-4) or lumiracoxib (CAS RN 220991-20-8).

The compounds of the present invention may also be administered in combination with naturally occurring substances that act to lower plasma cholesterol levels. These naturally occurring materials are commonly called nutraceuticals and include, for example, garlic extract, Hoodia plant extracts and niacin. A slow-release form of niacin is commercially available under the brand name Niaspan. Niacin may also be combined with other therapeutic agents such as lovastatin, which is an HMG-CoA reductase inhibitor. This combination therapy is known as Advicor® (Kos Pharmaceuticals Inc.).

The Formula (I) compounds of the present invention may also be used in combination with antihypertensive agents. Preferred antihypertensive agents include calcium channel blockers such as Cardizem®, Adalat®, Calan®, Cardene®, Covera®, Dilacor®, DynaCirc®, Procardia XL®, Sular®, Tiazac®, Vascor®, Verelan®, Isoptin®, Nimotop®, Norvasc®, and Plendil®; angiotensin converting enzyme (ACE) inhibitors, such as Accupril®, Altace®, Captopril®, Lotensin®, Mavik®, Monopril®, Prinivil®, Univasc®, Vasotec® and Zestril®.

Diabetes (especially Type II), insulin resistance, impaired glucose tolerance, or the like may be treated by the administration of a therapeutically effective amount of a compound of Formula (I), preferably in combination with one or more other agents (e.g., insulin) that are useful in treating diabetes.

Any glycogen phosphorylase inhibitor may be used as the second agent in combination with a Formula (I) compound of the present invention. The term glycogen phosphorylase inhibitor refers to compounds that inhibit the bioconversion of glycogen to glucose-1-phosphate, which is catalyzed by the enzyme glycogen phosphorylase. Such glycogen phosphorylase inhibition activity is readily determined by standard assays well known in the art (e.g., J. Med. Chem. 41 (1998) 2934-2938). Glycogen phosphorylase inhibitors of interest herein include those described in PCT patent application publication Nos. WO 96/39384 and WO 96/39385. The references cited above are incorporated herein by reference.

Aldose reductase inhibitors are also useful in the practice of the combination aspect of the present invention. These compounds inhibit the bioconversion of glucose to sorbitol, which is catalyzed by the enzyme aldose reductase. Aldose reductase inhibition is readily determined by standard assays (e.g., J. Malone, Diabetes, 29:861-864 (1980) "Red Cell Sorbitol, an Indicator of Diabetic Control", incorporated herein by reference). A variety of aldose reductase inhibitors are known to those skilled in the art. The references cited above are incorporated herein by reference.

Any sorbitol dehydrogenase inhibitor may be used in combination with a Formula (I) compound of the present invention. The term sorbitol dehydrogenase inhibitor refers to compounds that inhibit the bioconversion of sorbitol to fructose, which is catalyzed by the enzyme sorbitol dehydrogenase. Such sorbitol dehydrogenase inhibitor activity is readily determined by the use of standard assays well known in the art (e.g., Analyt. Biochem (2000) 280: 329-331). Sorbitol dehydrogenase inhibitors of interest include those disclosed in U.S. Pat. Nos. 5,728,704 and 5,866,578. The references cited above are incorporated herein by reference.

Any glucosidase inhibitor can be used in the combination aspect of the present invention. Such compounds inhibit the enzymatic hydrolysis of complex carbohydrates by glycoside hydrolases such as amylase or maltase into bioavailable simple sugars, for example, glucose. The rapid metabolic action of glucosidases, particularly following the intake of high levels of carbohydrates, results in a state of alimentary hyperglycemia, which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known that chyme remaining in the stomach promotes the production of gastric juice, which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom. Such glucosidase inhibition activity is readily determined by those skilled in the art according to standard assays (e.g., Biochemistry (1969) 8: 4214), incorporated herein by reference.

A generally preferred glucosidase inhibitor includes an amylase inhibitor. An amylase inhibitor is a glucosidase inhibitor that inhibits the enzymatic degradation of starch or glycogen into maltose. Such amylase inhibition activity is readily determined by use of standard assays (e.g., Methods Enzymol. (1955) 1: 149, incorporated herein by reference). The inhibition of such enzymatic degradation is beneficial in reducing amounts of bioavailable sugars, including glucose and maltose, and the concomitant deleterious conditions resulting therefrom.

Preferred glucosidase inhibitors include acarbose, adiposine, voglibose, miglitol, emiglitate, camiglibose, tendamistate, trestatin, pradimicin-Q and salbostatin. The glucosidase inhibitor acarbose and various amino sugar derivatives related thereto are disclosed in U.S. Pat. Nos. 4,062,950 and 4,174,439 respectively. The glucosidase inhibitor adiposine is disclosed in U.S. Pat. No. 4,254,256.

The glucosidase inhibitor voglibose, 3,4-dideoxy-4-[[2-hydroxy-1-(hydroxymethyl)ethyl]amino]-2-C(hydroxymethyl)-D-epi-inositol, and various N-substituted pseudo-aminosugars related thereto are disclosed in U.S. Pat. No. 4,701,559. The glucosidase inhibitor miglitol, (2R,3R,4R,5S)-1-(2-hydroxyethyl)-2-(hydroxymethyl)-3,4,5-piperidinetriol, and various 3,4,5-trihydroxypiperidines related thereto are disclosed in U.S. Pat. No. 4,639,436. The glucosidase inhibitor emiglitate, ethyl p-[2-[(2R,3R,4R,5S)-3,4,5-trihydroxy-2-(hydroxymethyl)piperidino]ethoxy]-benzoate, various derivatives related thereto and pharmaceutically acceptable acid addition salts thereof are disclosed in U.S. Pat. No. 5,192,772. The glucosidase inhibitor MDL-25637, 2,6-dideoxy-7-O-β-D-glucopyrano-syl-2,6-imino-D-glycero-L-gluco-heptitol, various homodisaccharides related thereto and the pharmaceutically acceptable acid addition salts thereof are disclosed in U.S. Pat. No. 4,634,765. The glucosidase inhibitor camiglibose, methyl 6-deoxy-6-[(2R,3R,4R,5S)-3,4,5-trihydroxy-2-(hydroxymethyl)piperidino]-α-D-glucopyranoside sesquihydrate, deoxy-nojirimycin derivatives related thereto, various pharmaceutically acceptable salts thereof and synthetic methods for the preparation thereof are disclosed in U.S. Pat. Nos. 5,157,116 and 5,504,078. The glycosidase inhibitor salbostatin and various pseudosaccharides related thereto are disclosed in U.S. Pat. No. 5,091,524. All of the references cited above are incorporated herein by reference.

Amylase inhibitors of interest herein are disclosed in U.S. Pat. Nos. 4,451,455, 4,623,714 (Al-3688 and the various cyclic polypeptides related thereto) and U.S. Pat. No. 4,273,765 (trestatin, which consists of a mixture of trestatin A, trestatin B and trestatin C, and the various trehalose-containing aminosugars related theret). All of the references cited above are incorporated herein by reference.

The dosage of the additional pharmaceutical agent is generally dependent upon a number of factors including the health of the subject being treated, the extent of treatment desired, the nature and kind of concurrent therapy, if any, and the frequency of treatment and the nature of the effect desired. In general, the dosage range of the additional pharmaceutical agent is in the range of from about 0.001 mg to about 100 mg per kilogram body weight of the individual per day, preferably from about 0.1 mg to about 10 mg per kilogram body weight of the individual per day. However, some variability in the general dosage range may also be required depending upon the age and weight of the subject being treated, the intended route of administration, the particular anti-obesity agent being administered and the like. The determination of dosage ranges and optimal dosages for a particular patient is also well within the ability of one of ordinary skill in the art having the benefit of the instant disclosure.

According to the methods of treatment of the invention, a compound of the present invention or a combination is administered to a subject in need of such treatment, preferably in the form of a pharmaceutical composition. In the combination aspect of the invention, the compound of the present invention and the other pharmaceutical agent(s) may be administered either separately or in a pharmaceutical composition comprising both. It is generally preferred that such administration be oral.

When a combination of a compound of the present invention and at least one other pharmaceutical agent are administered together, such administration may be sequential in time or simultaneous. Simultaneous administration of drug combinations is generally preferred. For sequential administration, a compound of the present invention and the additional pharmaceutical agent may be administered in any order. It is generally preferred that such administration be oral. It is especially preferred that such administration be oral and simultaneous. When a compound of the present invention and the additional pharmaceutical agent are administered sequentially, the administration of each may be by the same or by different methods.

Accordingly, a compound of the present invention or a combination can be administered to a patient separately or together in any conventional oral, rectal, transdermal, parenteral (e.g., intravenous, intramuscular or subcutaneous), intracisternal, intravaginal, intraperitoneal, topical (e.g., powder, ointment, cream, spray or lotion), buccal or nasal dosage form (e.g., spray, drops or inhalant).

The compounds of the invention or combinations will generally be administered in admixture with one or more suitable pharmaceutical excipients, diluents or carriers known in the art and selected with regard to the intended route of administration and standard pharmaceutical practice. The compound of the invention or combination may be formulated to provide immediate-, delayed-, modified-, sustained-, pulsed- or controlled-release dosage forms depending on the desired route of administration and the specificity of release profile, commensurate with therapeutic needs.

The pharmaceutical compositions comprise a compound the invention or a combination in an amount generally in the range of from about 1% to about 75%, 80%, 85%, 90% or even 95% (by weight) of the composition, usually in the range of about 1%, 2% or 3% to about 50%, 60% or 70%, more frequently in the range of about 1%, 2% or 3% to less than 50% such as about 25%, 30% or 35%.

Methods of preparing various pharmaceutical compositions with a specific amount of active compound are known to those skilled in this art. For examples, see Remington: The Practice of Pharmacy, Lippincott Williams and Wilkins, Baltimore Md., 20$^{th}$ ed. 2000.

Compositions suitable for parenteral injection generally include pharmaceutically acceptable sterile aqueous or nonaqueous solutions, dispersions, suspensions, or emulsions, and sterile powders for reconstitution into sterile injectable solutions or dispersions. Examples of suitable aqueous and nonaqueous carriers or diluents (including solvents and vehicles) include water, ethanol, polyols (propylene glycol, polyethylene glycol, glycerol, and the like), suitable mixtures thereof, triglycerides including vegetable oils such as olive oil, and injectable organic esters such as ethyl oleate. A prefrerred carrier is Miglyol® brand caprylic/capric acid ester with glycerine or propylene glycol (e.g., Miglyol® 812, Miglyol® 829, Miglyol® 840) available from Condea Vista Co., Cranford, N.J. Proper fluidity can be maintained, for example, by the use of a coating such as lecithin, by the maintenance of the required particle size in the case of dispersions, and by the use of surfactants.

These compositions for parenteral injection may also contain excipients such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, chews, lozenges, pills, powders, and multiparticulate preparations (granules). In such solid dosage forms, a compound of the present invention or a combination is admixed with at least one inert excipient, diluent or carrier. Suitable excipients, diluents or carriers include materials such as sodium citrate or dicalcium phosphate and/or (a) fillers or extenders (e.g., microcrystalline cellulose (available as Avicel™ from FMC Corp.) starches, lactose, sucrose, mannitol, silicic acid, xylitol, sorbitol, dextrose, calcium hydrogen phosphate, dextrin, alpha-cyclodextrin, beta-cyclodextrin, polyethylene glycol, medium chain fatty acids, titanium oxide, magnesium oxide, aluminum oxide and the like); (b) binders (e.g., carboxymethylcellulose, methylcellulose, hydroxypropylcellulose, hydroxypropylmethylcellulose, gelatin, gum arabic, ethyl cellulose, polyvinyl alcohol, pullulan, pregelatinized starch, agar, tragacanth, alginates, gelatin, polyvinylpyrrolidone, sucrose, acacia and the like); (c) humectants (e.g., glycerol and the like); (d) disintegrating agents (e.g., agar-agar, calcium carbonate, potato or tapioca starch, alginic acid, certain complex silicates, sodium carbonate, sodium lauryl sulphate, sodium starch glycolate (available as Explotab™ from Edward Mendell Co.), cross-linked polyvinyl pyrrolidone, croscarmellose sodium A-type (available as Ac-di-sol™), polyacrilin potassium (an ion exchange resin) and the like); (e) solution retarders (e.g., paraffin and the like); (f) absorption accelerators (e.g., quaternary ammonium compounds and the like); (g) wetting agents (e.g., cetyl alcohol, glycerol monostearate and the like); (h) adsorbents (e.g., kaolin, bentonite and the like); and/or (i) lubricants (e.g., talc, calcium stearate, magnesium stearate, stearic acid, polyoxyl stearate, cetanol, talc, hydrogenated caster oil, sucrose esters of fatty acid, dimethylpolysiloxane, microcrystalline wax, yellow beeswax, white beeswax, solid polyethylene glycols, sodium lauryl sulfate and the like). In the case of capsules and tablets, the dosage forms may also comprise buffering agents.

Solid compositions of a similar type may also be used as fillers in soft or hard filled gelatin capsules using such excipients, diluents or carriers as lactose or milk sugar, as well as high molecular weight polyethylene glycols, and the like.

Solid dosage forms such as tablets, dragees, capsules, and granules may be prepared with coatings and shells, such as enteric coatings and others well known in the art. They may also contain opacifying agents, and can also be of such composition that they release the compound of the present invention and/or the additional pharmaceutical agent in a delayed manner. Examples of embedding compositions that can be used are polymeric substances and waxes. The drug may also be in micro-encapsulated form, if appropriate, with one or more of the above-mentioned excipients, diluents or carriers.

For tablets, the active agent will typically comprise less than 50% (by weight) of the formulation, for example less than about 10% such as 5% or 2.5% by weight. The predominant portion of the formulation comprises excipients, diluents or carriers such as fillers, disintegrants, lubricants and, optionally, flavors. The composition of these excipients is well known in the art. Frequently, the fillers/diluents will comprise mixtures of two or more of the following components: microcrystalline cellulose, mannitol, lactose (any/all types), starch, and di-calcium phosphate. The excipient, diluent or carrier mixtures typically comprise less than about 98% of the formulation and preferably less than about 95%, for example about 93.5%. Preferred disintegrants include Ac-di-sol™, Explotab™, starch and sodium lauryl sulphate. When present a disintegrant will usually comprise less than about 10% of the formulation or less than about 5%, for example about 3%. When present a lubricant will usually comprise less than about 5% of the formulation or less than about 3%, for example about 1%. A preferred lubricant is magnesium stearate.

Tablets may be manufactured by standard tabletting processes, for example, direct compression or a wet, dry or melt granulation, melt congealing process and extrusion. The tablet cores may be mono or multi-layer(s) and can be coated with appropriate overcoats known in the art.

Liquid dosage forms for oral administration include pharmaceutically acceptable emulsions, solutions, suspensions, syrups, and elixirs. In addition to the compound of the present invention or the combination, the liquid dosage form may contain inert excipients, diluents or carriers commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), Miglyol® (available from CONDEA Vista Co., Cranford, N.J.), glycerol, tetrahydrofurfuryl alcohol, polyethylene glycols and fatty acid esters of sorbitan, or mixtures of these substances, and the like.

Besides such inert excipients, diluents or carriers, the composition may also include wetting, emulsifying and/or suspending agents and sweetening, flavoring and/or perfuming agents.

Oral liquid forms of the compounds of the invention or combinations include solutions, wherein the active compound is fully dissolved. Examples of solvents include all pharmaceutically precedented solvents suitable for oral administration, particularly those in which the compounds of the invention show good solubility, e.g., polyethylene glycol, polypropylene glycol, edible oils and glyceryl- and glyceride-based systems. Glyceryl- and glyceride-based systems may include, for example, the following branded products (and corresponding generic products): Captex™ 355 EP (glyceryl tricaprylate/caprate, from Abitec, Columbus Ohio), Crodamol™ GTC/C (medium chain triglyceride, from Croda, Cowick Hall, UK) or Labrafac™ CC (medium chain triglyides, from Gattefosse), Captex™ 500P (glyceryl triacetate i.e. triacetin, from Abitec), Capmul™ MCM (medium chain mono- and diglycerides, from Abitec), Migyol™ 812 (caprylic/capric triglyceride, from Condea, Cranford NJ), Migyol™ 829 (caprylic/capric/succinic triglyceride, from Condea), Migyol™ 840 (propylene glycol dicaprylate/dicaprate, from Condea), Labrafil™ M1944CS (oleoyl macrogol-6 glycerides, from Gattefosse), Peceol™ (glyceryl monooleate, from Gattefosse) and Maisine™ 35-1(glyceryl monooleate, from Gattefosse). Of particular interest are the medium chain (about $C_8$ to $C_{10}$) triglyceride oils. These solvents frequently make up the predominant portion of the composition, i.e., greater than about 50%, usually greater than about 80%, for example about 95%, 97% or 99%. Other excipients, diluents or carriers may also be included with the solvents principally as taste-mask agents, palatability and flavoring agents, antioxidants, stabilizers, texture and viscosity modifiers, solubilizers and the like.

Suspensions, in addition to the compound of the present invention or the combination, may further comprise excipients, diluents or carriers such as suspending agents, e.g., ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing a compound of the present invention or a combination with suitable non-irritating excipients, diluents or carriers, such as cocoa butter, polyethylene glycol or a suppository wax which are solid at ordinary room temperature, but liquid at body temperature, and therefore, melt in the rectum or vaginal cavity thereby releasing the active component(s).

Dosage forms for topical administration of the compounds of the present invention or combinations include ointments, creams, lotions, powders and sprays. The drugs are admixed with a pharmaceutically acceptable excipient, diluent or carrier, and any preservatives, buffers, or propellants that may be required or desired.

For any of the present compounds are poorly soluble in water, e.g., less than about 1 µg/mL, liquid compositions in solubilizing, non-aqueous solvents such as the medium chain triglyceride oils discussed above are a preferred dosage form. Solid amorphous dispersions, including dispersions formed by a spray-drying process, are also a preferred dosage form for poorly soluble compounds of the invention. By "solid amorphous dispersion" is meant a solid material in which at least a portion of the poorly soluble compound is in the amorphous form and dispersed in a water-soluble polymer. By "amorphous" is meant that the poorly soluble compound is not crystalline. By "crystalline" is meant that the compound exhibits long-range order in three dimensions of at least 100 repeat units in each dimension. Thus, the term amorphous is intended to include not only material which has essentially no order, but also material which may have some small degree of order, but the order is in less than three dimensions and/or is only over short distances. Amorphous material may be characterized by techniques known in the art such as powder x-ray diffraction (PXRD) crystallography, solid state NMR, or thermal techniques such as differential scanning calorimetry (DSC).

Preferably, at least a major portion (i.e., at least about 60 wt %) of the poorly soluble compound in the solid amorphous dispersion is amorphous. The compound can exist within the solid amorphous dispersion in relatively pure amorphous domains or regions, as a solid solution of the compound homogeneously distributed throughout the polymer or any combination of these states or those states that lie intermediate between them. Preferably, the solid amorphous dispersion is substantially homogeneous so that the amorphous compound is dispersed as homogeneously as possible throughout the polymer. As used herein, "substantially homogeneous" means that the fraction of the compound that is present in relatively pure amorphous domains or regions within the solid amorphous dispersion is relatively small, on the order of less than about 20 wt %, and preferably less than about 10 wt % of the total amount of drug.

Water-soluble polymers suitable for use in the solid amorphous dispersions should be inert, in the sense that they do not chemically react with the poorly soluble compound in an adverse manner, are pharmaceutically acceptable, and have at least some solubility in aqueous solution at physiologically relevant pHs (e.g. 1-8). The polymer can be neutral or ionizable, and should have an aqueous-solubility of at least 0.1 mg/mL over at least a portion of the pH range of 1-8.

Water-soluble polymers suitable for use with the present invention may be cellulosic or non-cellulosic. The polymers may be neutral or ionizable in aqueous solution. Of these, ionizable and cellulosic polymers are preferred, with ionizable cellulosic polymers being more preferred.

Exemplary water-soluble polymers include hydroxypropyl methyl cellulose acetate succinate (HPMCAS), hydroxypropyl methyl cellulose (HPMC), hydroxypropyl methyl cellulose phthalate (HPMCP), carboxy methyl ethyl cellulose (CMEC), cellulose acetate phthalate (CAP), cellulose acetate trimellitate (CAT), polyvinylpyrrolidone (PVP), hydroxypropyl cellulose (HPC), methyl cellulose (MC), block copolymers of ethylene oxide and propylene oxide (PEO/PPO, also known as poloxamers), and mixtures thereof. Especially preferred polymers include HPMCAS, HPMC, HPMCP, CMEC, CAP, CAT, PVP, poloxamers, and mixtures thereof. Most preferred is HPMCAS. See European Patent Application Publication No. 0 901 786 A2, the disclosure of which is incorporated herein by reference.

The solid amorphous dispersions may be prepared according to any process for forming solid amorphous dispersions that results in at least a major portion (at least 60%) of the poorly soluble compound being in the amorphous state. Such processes include mechanical, thermal and solvent processes. Exemplary mechanical processes include milling and extrusion; melt processes including high temperature fusion, solvent-modified fusion and melt-congeal processes; and solvent processes including non-solvent precipitation, spray coating and spray drying. See, for example, the following U.S. Patents, the pertinent disclosures of which are incorporated herein by reference: U.S. Pat. Nos. 5,456,923 and 5,939,099, which describe forming dispersions by extrusion processes; U.S. Pat. Nos. 5,340,591 and 4,673,564, which describe forming dispersions by milling processes; and U.S. Pat. Nos. 5,707,646 and 4,894,235, which describe forming dispersions by melt congeal processes. In a preferred process, the solid amorphous dispersion is formed by spray drying, as disclosed in European Patent Application Publication No. 0 901 786 A2. In this process, the compound and polymer are dissolved in a solvent, such as acetone or methanol, and the solvent is then rapidly removed from the solution by spray drying to form the solid amorphous dispersion. The solid amorphous dispersions may be prepared to contain up to about 99 wt % of the compound, e.g., 1 wt %, 5 wt %, 10 wt %, 25 wt %, 50 wt %, 75 wt %, 95 wt %, or 98 wt % as desired.

The solid dispersion may be used as the dosage form itself or it may serve as a manufacturing-use-product (MUP) in the preparation of other dosage forms such as capsules, tablets, solutions or suspensions. An example of an aqueous suspension is an aqueous suspension of a 1:1 (w/w) compound/HPMCAS-HF spray-dried dispersion containing 2.5 mg/mL of compound in 2% polysorbate-80. Solid dispersions for use in a tablet or capsule will generally be mixed with other excipients or adjuvants typically found in such dosage forms. For example, an exemplary filler for capsules contains a 2:1 (w/w) compound/HPMCAS-MF spray-dried dispersion (60%), lactose (fast flow) (15%), microcrystalline cellulose (e.g., Avicel®-102) (15.8%), sodium starch (7%), sodium lauryl sulfate (2%) and magnesium stearate (1%).

The HPMCAS polymers are available in low, medium and high grades as Aqoat®-LF, Aqoat®-MF and Aqoat®-HF respectively from Shin-Etsu Chemical Co., LTD, Tokyo, Japan. The higher MF and HF grades are generally preferred.

The pharmaceutical composition for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Use in Veterinary Medicine

The following paragraphs describe exemplary formulations, dosages, etc. useful for non-human animals. The administration of the compounds of the present invention and combinations of the compounds of the present invention with anti-obesity agents can be effected orally or non-orally.

An amount of a compound of the present invention or combination of a compound of the present invention with an anti-obesity agent is administered such that an effective dose is received. Generally, a daily dose that is administered orally to an animal is between about 0.01 and about 1,000 mg/kg of body weight, e.g., between about 0.01 and about 300 mg/kg or between about 0.01 and about 100 mg/kg or between about 0.01 and about 50 mg/kg, or between about 0.01 and about 25 mg/kg, or about 0.01 and about 10 mg/kg or about 0.01 and about 5 mg/kg of body weight.

Conveniently, a compound of the present invention (or combination) can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

Conveniently, a compound of the present invention (or combination) can also be added directly to the feed, as such, or in the form of an animal feed supplement, also referred to as a premix or concentrate. A premix or concentrate of the compound in an excipient, diluent or carrier is more commonly employed for the inclusion of the agent in the feed. Suitable excipients, diluents or carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective excipient, diluent or carrier is the respective animal feed itself; that is, a small portion of such feed. The carrier facilitates uniform distribution of the compound in the finished feed with which the premix is blended. Preferably, the compound is thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of the compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Drinking water and feed effective for increasing lean meat deposition and for improving lean meat to fat ratio are generally prepared by mixing a compound of the present invention with a sufficient amount of animal feed to provide from about $10^{-3}$ to about 500 ppm of the compound in the feed or water.

The preferred medicated swine, cattle, sheep and goat feed generally contain from about 1 to about 400 grams of a compound of the present invention (or combination) per ton of feed, the optimum amount for these animals usually being about 50 to about 300 grams per ton of feed.

The preferred poultry and domestic pet feeds usually contain about 1 to about 400 grams and preferably about 10 to about 400 grams of a compound of the present invention (or combination) per ton of feed.

The compounds of the present invention may be administered top an animal parenterally. Pellets or standard injectable solutions or suspensions are useful for parenteral administration. In general, parenteral administration involves injection of a sufficient amount of a compound of the present invention (or combination) to provide the animal with about 0.01 to about 20 mg/kg/day of body weight of the drug. The preferred dosage for poultry, swine, cattle, sheep, goats and domestic pets is in the range of from about 0.05 to about 10 mg/kg/day of body weight of drug.

The compounds of the present invention (or combination) may be prepared in the form of a pellet and administered as an implant, usually under the skin of the head or ear of the animal in which increase in lean meat deposition and improvement in lean meat to fat ratio is sought.

Pellets containing an effective amount of a compound of the present invention, pharmaceutical composition, or combination may be prepared by admixing a compound of the present invention or combination with a diluent such as carbowax, carnuba wax, and the like, and a lubricant, such as magnesium or calcium stearate, may be added to improve the pelleting process.

It is, of course, recognized that more than one pellet may be administered to an animal to achieve the desired dose level which will provide the increase in lean meat deposition and improvement in lean meat to fat ratio desired. Moreover, implants may also be made periodically during the animal treatment period in order to maintain the proper drug level in the animal's body.

The compounds of the present invention may also be administered orally to non-human animals, for example companion animals such as dogs, cats and horses, and food-source animals, in the same dosage forms as used for humans, for example tablets, capsules, solutions, suspensions, pastes, powders etc.

Paste Formulations may be prepared by dispersing the drug in a pharmaceutically acceptable oil such as peanut oil, sesame oil, corn oil or the like.

The present invention has several advantageous veterinary features. For the pet owner or veterinarian who wishes to increase leanness and/or trim unwanted fat from pet animals, the instant invention provides the means by which this may be accomplished. For poultry, beef and swine breeders, utilization of the method of the present invention yields leaner animals that command higher sale prices from the meat industry.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), and AstraZeneca Pharmaceuticals (London, England) or may be prepared using methods known to those of average skill in the art from readily available materials.

General Experimental Procedures

NMR spectra were recorded on a Varian Unity™ 400 (available from Varian Inc., Palo Alto, Calif.) at room temperature at 400 and 500 MHz $^1$H, respectively. Chemical shifts are expressed in parts per million (δ) relative to residual solvent as an internal reference. The peak shapes are denoted as follows: s, singlet; d, doublet; t, triplet; q, quartet; m, multiplet; br s, broad singlet; v br s, very broad singlet; br m, broad multiplet. In some cases only representative $^1$H NMR peaks are given.

Mass spectra were recorded by direct flow analysis using positive and negative atmospheric pressure chemical ionization (APcI) scan modes. A Waters APcI/MS model ZMD mass spectrometer equipped with Gilson 215 liquid handling system was used to carry out the experiments Mass spectrometry analysis was also obtained by RP-HPLC gradient method for chromatographic separation. Molecular weight identification was recorded by positive and negative electrospray ionization (ESI) scan modes. A Waters/Micromass ESI/MS model ZMD or LCZ mass spectrometer (Waters Corp., Milford, Mass.) equipped with Gilson 215 liquid handling system (Gilson, Inc., Middleton, Wis.) and HP 1100 DAD (Hewlett Packard) was used to carry out the experiments.

Where the intensity of chlorine or bromine-containing ions are described, the expected intensity ratio was observed (approximately 3:1 for $^{35}$Cl/$^{37}$Cl-containing ions and 1:1 for $^{79}$Br/$^{81}$Br-containing ions) and only the lower mass ion is given. Optical rotations were determined on a PerkinElmer™ 241 polarimeter (available from PerkinElmer Inc., Wellesley, Mass.) using the sodium D line (λ=589 nm) at the indicated temperature and are reported as follows [α]$_D^{temp}$, concentration (c=g/100 mL), and solvent.

Column chromatography was performed with either Baker™ silica gel (40 μm, J. T. Baker, Phillipsburg, N.J.) or Silica Gel 50 (EM Sciences™, Gibbstown, N.J.) in glass columns, in Biotage™ columns (Biotage, Inc., Charlottesville, USA) or using an Isco Combiflash Separation System under low nitrogen pressure. Radial chromatography was performed using a Chromatotron™ (Harrison Research).

Selected purifications were performed using Shimadzu Preparation Liquid Chromatography. Chiral separations were made using a Chirlapak AD, (S,S)-Whelk-O 1 or Chiralcel OD column. References to "enantiomer 1" or "enantiomer 2" merely refer to the order in which the compounds elute from the column.

In the discussion which follows, certain common abbreviations and acronyms have been employed which include: AcOH (acetic acid), DMAP (4-dimethylaminopyridine), DMF (dimethylformamide), Et$_2$O (diethyl ether), EtOAc (ethyl acetate), EtOH (ethanol), Et$_3$N (triethylamine), KHMDS (potassium hexamethyldisilazane), MeOH (methanol), NaBH(OAc)$_3$ (sodium triacetoxyborohydride), NaHMDS (sodium hexamethyldisilazane), TFA (trifluoroacetic acid), THF (tetrahydrofuran).

Example 1(A)

Preparation of 2-[4-(6-Fluoro-1H-indol-3-ylmethyl)-5-oxo-1-phenyl-4,5-dihydro-2,3,6,10b-tetraaza-benzo[e]azulen-6-yl]-N-isopropyl-N-(6-methoxy-pyridin-3-yl)-acetamide

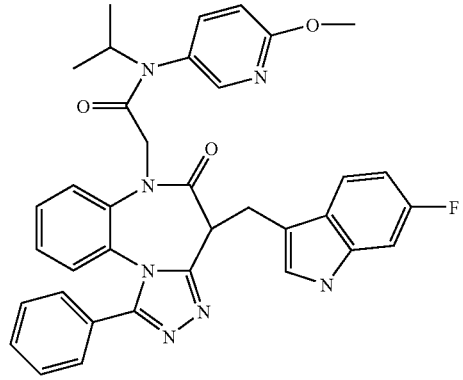

Step A: 2-[4-(6-Fluoro-1H-indol-3-ylmethylene)-5-oxo-1-phenyl-4,5-dihydro-2,3,6,10b-tetraaza-benzo [e]azulen-6-yl]-N-isopropyl-N-(6-methoxy-pyridin-3-yl)-acetamide To a solution of N-isopropyl-N-(6-methoxy-pyridin-3-yl)-2-(5-oxo-1-phenyl-4,5-dihydro-2,3,6,10b-tetraazabenzo[e]azulen-6-yl)-acetamide (Preparation 11) (150 mg, 0.311 mmol) and 6-fluoro-1H-indole-3-carbaldehyde (61 mg, 0.373 mmol) in toluene (20 mL) was added piperidine (100 μL). The reaction vessel was equipped with a Dean-Stark trap that contained toluene and 4A molecular sieves and was heated at reflux for 24 hours. The solution was cooled to room temperature and was diluted with water. The aqueous solution was washed with EtOAc (3×) and the combined organic extracts were dried (MgSO$_4$), filtered and concentrated. The residue was purified by medium pressure chromatography eluting with a solvent gradient (10% EtOAc in hexanes to 100% EtOAc) to yield 158 mg of 2-[4-(6-fluoro-1H-indol-3-ylmethylene)-5-oxo-1-phenyl-4,5-dihydro-2,3,6,10b-tetraaza-benzo[e]azulen-6-yl]-N-isopropyl-N-(6-methoxy-pyridin-3-yl)-acetamide. MS 628.3 (M+1), 626.2 (M−1).

Step B: (2-[4-(6-Fluoro-1H-indol-3-ylmethyl)-5-oxo-1-phenyl-4,5-dihydro-2,3,6,10b-tetraaza-benzo[e]azulen-6-yl]-N-isopropyl-N-(6-methoxy-pyridin-3-yl)-acetamide)

To a solution of 2-[4-(6-fluoro-1H-indol-3-ylmethylene)-5-oxo-1-phenyl-4,5-dihydro-2,3,6,10b-tetraaza-benzo[e]azulen-6-yl]-N-isopropyl-N-(6-methoxy-pyridin-3-yl)-acetamide (158 mg, 0.252 mmol) in MeOH (20 mL) was added ammonium formate (463 mg, 7.34 mmol) and 10% palladium on charcoal (112 mg). The reaction was heated at reflux for 24 hours. The suspension was filtered hot, rinsing with 10% MeOH in $CH_2Cl_2$ (3×) and with $CH_2Cl_2$ (3×). The combined organic filtrates were concentrated and the residue was purified by medium pressure chromatography eluting with a solvent gradient (2% MeOH in $CH_2Cl_2$ to 8% MeOH in $CH_2Cl_2$) to yield 110 mg of 2-[4-(6-fluoro-1H-indol-3-ylmethyl)-5-oxo-1-phenyl-4,5-dihydro-2,3,6,10b-tetraaza-benzo[e]azulen-6-yl]-N-isopropyl-N-(6-methoxy-pyridin-3-yl)-acetamide. $^1$H NMR ($CD_3OD$) δ 8.08 (d, 1H), 7.39-7.62 (m, 9H) 7.15 (m, 2H), 6.93 (m, 3H), 6.68 (m, 1H), 4.80 (m, 1H), 4.55 (m, 1H), 4.20 (m, 1H), 3.95 (s, 3H), 3.88 (t, 1H), 3.77 (m, 1H), 3.67 (m, 1H), 1.01 (m, 6H); MS 630 (M+1), 628.5 (M−1).

Example 1(B)

Preparation of (−) 2-[4-(1H-Indol-3-ylmethyl)-5-oxo-1-phenyl-4,5-dihydro-2,3,6,10b-tetraaza-benzo[e]azulen-6-yl]-N-isopropyl-N-(6-methoxy-pyridin-3-yl)-acetamide

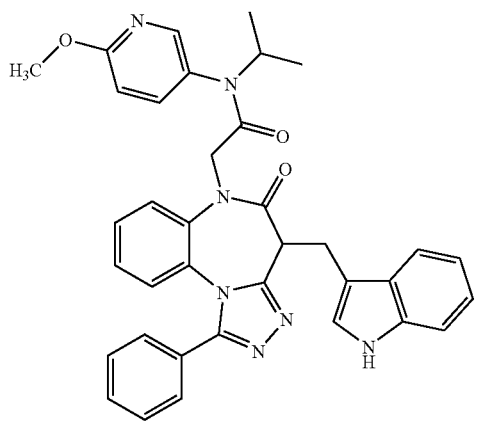

Step A: 2-[4-(1H-Indol-3-ylmethylene)-5-oxo-1-phenyl-4,5-dihydro-2,3,6,10b-tetraaza-benzo[e]azulen-6-yl]-N-isopropyl-N-(6-methoxy-pyridin-3-yl)-acetamide Following the procedure described for Example 1 (A), Step A, N-isopropyl-N-(6-methoxy-pyridin-3-yl)-2-(5-oxo-1-phenyl-4,5-dihydro-2,3,6,10b-tetraaza-benzo[e]azulen-6-yl)-acetamide (Preparation 11) (293 mg, 0.608 mmol) was condensed with 1H-indole-3-carbaldehyde (106 mg, 0.729 mmol). Purification by medium pressure chromatography eluting with a solvent gradient (2% MeOH in $CH_2Cl_2$ to 10% MeOH in $CH_2Cl_2$) yielded 286 mg of 2-[4-(1H-indol-3-ylmethylene)-5-oxo-1-phenyl-4,5-dihydro-2,3,6,10b-tetraaza-benzo[e]azulen-6-yl]-N-isopropyl-N-(6-methoxy-pyridin-3-yl)-acetamide. $^1$H NMR ($CD_3OD$) δ 8.25 (s) and 7.90 (s, total 1H), 8.16 (s, 1H), 7.58-7.67 (m, 4H), 7.37-7.53 (m, 6H), 7.07-7.17 (m, 3H), 6.94 (m, 2H), 4.90 (m, 1H), 4.55 (m, 1H), 4.25 (m, 1H), 3.96 (m, 4H), 1.10 (m, 6H); MS 610.8 (M+1), 608.5 (M−1)

Step B: 2-[4-(1H-Indol-3-ylmethyl)-5-oxo-1-phenyl-4,5-dihydro-2,3,6,10b-tetraaza-benzo[e]azulen-6-yl]-N-isopropyl-N-(6-methoxy-pyridin-3-yl)-acetamide Following the procedure described for Example 1 (A), Step B, 2-[4-(1H-indol-3-ylmethylene)-5-oxo-1-phenyl-4,5-dihydro-2,3,6,10b-tetraaza-benzo[e]azulen-6-yl]-N-isopropyl-N-(6-methoxy-pyridin-3-yl)-acetamide (276 mg, 0.453 mmol) was reduced and purified by medium pressure chromatography eluting with a solvent gradient ($CH_2Cl_2$ to 5% MeOH in $CH_2Cl_2$) to yield 86 mg of 2-[4-(1H-indol-3-ylmethyl)-5-oxo-1-phenyl-4,5-dihydro-2,3,6,10b-tetraaza-benzo[e]azulen-6-yl]-N-isopropyl-N-(6-methoxy-pyridin-3-yl)-acetamide as a racemic mixture. $^1$H NMR ($CD_3OD$) δ 8.08 (d, 1H), 7.61 (m, 3H), 7.39-7.53 (m, 6H), 7.25 (d, 1H), 7.12 (m, 2H), 7.00 (m, 1H), 6.90 (m, 3H), 4.78 (m, 1H), 4.55 (m, 1H), 4.15 (m, 1H), 3.95 (s, 3H), 3.89 (m, 1H), 3.67-3.80 (m, 2H), 1.01 (m, 6H); MS 612.2 (M+1), 610.5 (M−1).

Step C: (−) 2-[4-(1H-indol-3-ylmethyl)-5-oxo-1-phenyl-4,5-dihydro-2,3,6,10b-tetraaza-benzo[e]azulen-6-yl]-N-isopropyl-N-(6-methoxy-pyridin-3-yl)-acetamide, enantiomer 1

The racemic product of Step B, 2-[4-(1H-indol-3-ylmethyl)-5-oxo-1-phenyl-4,5-dihydro-2,3,6,10b-tetraaza-benzo[e]azulen-6-yl]-N-isopropyl-N-(6-methoxy-pyridin-3-yl)-acetamide (217 mg, 0.355 mmol), was separated into its enantiomers by high pressure chromatography using a Chiralpak AD column (5 cm×50 cm), eluting with heptane in EtOH (75:12), using a flow rate of 85 mL/minute to give enantiomer 1 having a retention time of 7.04 minutes. The enantiomer was dissolved in EtOAc and the organic layer was washed with water (1×) and brine (1×). The organic extract was dried ($MgSO_4$), filtered and concentrated to provide 85 mg of 2-[4-(1H-indol-3-ylmethyl)-5-oxo-1-phenyl-4,5-dihydro-2,3,6,10b-tetraaza-benzo[e]azulen-6-yl]-N-isopropyl-N-(6-methoxy-pyridin-3-yl)-acetamide (enantiomer 1). $^1$H NMR ($CD_3OD$) δ 8.08 (d, 1H), 7.61 (m, 3H), 7.39-7.53 (m, 6H), 7.25 (d, 1H), 7.14 (m, 2H), 7.00 (t, 1H), 6.90 (m, 3H), 4.78 (m, 1H), 4.54 (m, 1H), 4.11 (m, 1H), 3.95 (s, 3H), 3.89 (t, 1H), 3.68-3.82 (m, 2H), 1.01 (m, 6H); MS 612.9 (M+1), 610.5 (M−1); $[\alpha]_D^{21}$-79.6 (c 0.325, ethanol).

Example 1(C)

Preparation of 2-[4-(5-Fluoro-1H-indol-3-ylmethyl)-5-oxo-1-phenyl-4,5-dihydro-2,3,6,10b-tetraaza-benzo[e]azulen-6-yl]-N-isopropyl-N-(6-methoxy-pyridin-3-yl)-acetamide

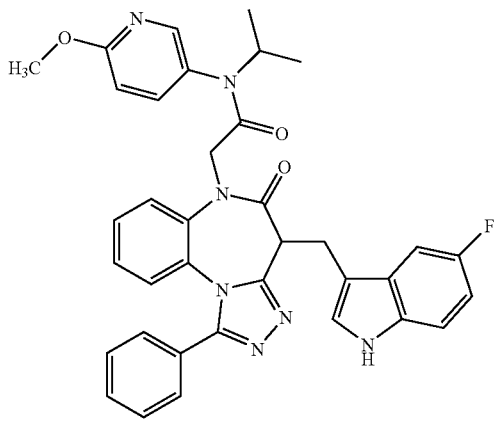

Step A: 2-[4-(5-Fluoro-1H-indol-3-ylmethylene)-5-oxo-1-phenyl-4,5-dihydro-2,3,6,10b-tetraaza-benzo[e]azulen-6-yl]-N-isopropyl-N-(6-methoxy-pyridin-3-yl)-acetamide Following the procedure described for Example 1 (A), Step A, N-isopropyl-N-(6-methoxy-pyridin-3-yl)-2-(5-oxo-1-phenyl-4,5-dihydro-2,3,6,10b-tetraaza-benzo[e]azulen-6-yl)-acetamide (Preparation 11) (120 mg, 0.207 mmol) was condensed with 5-fluoro-1H-indole-3-carbaldehyde (48 mg, 0.248 mmol). Purification by medium pressure chromatography eluting with a solvent gradient (1% MeOH in CH$_2$Cl$_2$ to 7% MeOH in CH$_2$Cl$_2$) yielded 85 mg of 2-[4-(5-fluoro-1H-indol-3-ylmethylene)-5-oxo-1-phenyl-4,5-dihydro-2,3,6,10b-tetraaza-benzo[e]azulen-6-yl]-N-isopropyl-N-(6-methoxy-pyridin-3-yl)-acetamide. MS 628.8 (M+1), 626.4 (M−1).

Step B: 2-[4-(5-Fluoro-1H-indol-3-ylmethyl)-5-oxo-1-phenyl-4,5-dihydro-2,3,6,10b-tetraaza-benzo[e]azulen-6-yl]-N-isopropyl-N-(6-methoxy-pyridin-3-yl)-acetamide Following the procedure described for Example 1 (A), Step B, 2-[4-(5-fluoro-1H-indol-3-ylmethylene)-5-oxo-1-phenyl-4,5-dihydro-2,3,6,10b-tetraaza-benzo[e]azulen-6-yl]-N-isopropyl-N-(6-methoxy-pyridin-3-yl)-acetamide (85 mg, 0.135 mmol) was reduced and purified by medium pressure chromatography eluting with a solvent gradient (2% MeOH in CH$_2$Cl$_2$ to 9% MeOH in CH$_2$Cl$_2$) to yield 42 mg of 2-[4-(5-fluoro-1H-indol-3-ylmethyl)-5-oxo-1-phenyl-4,5-dihydro-2,3,6,10b-tetraaza-benzo[e]azulen-6-yl]-N-isopropyl-N-(6-methoxy-pyridin-3-yl)-acetamide. $^1$H NMR (CD$_3$OD) δ 8.08 (d, 1H), 7.38-7.65 (m, 8H), 7.19 (m, 3H), 7.14 (t, 1H), 6.90 (d, 2H), 6.76 (t, 1H), 4.80 (m, 1H), 4.50 (m, 1H), 4.12 (m, 1H), 3.94 (s, 3H), 3.87 (t, 1H), 3.74 (m, 1H), 3.64 (m, 1H), 1.01 (m, 6H); MS 630.4 (M+1), 628.5 (M−1).

Example 1(D)

Preparation of 2-[1-Cyclohexyl-4-(1H-indol-3-ylmethyl)-5-oxo-4,5-dihydro-2,3,6,10b-tetraaza-benzo[e]azulen-6-yl]-N-isopropyl-N-(6-methoxy-pyridin-3-yl)-acetamide

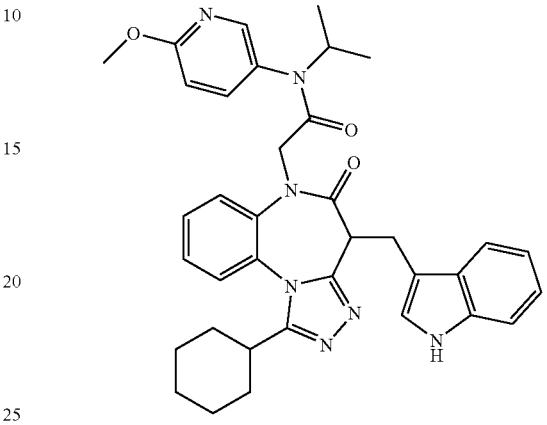

Step A: 2-[1-Cyclohexyl-4-(1H-indol-3-ylmethylene)-5-oxo-4,5-dihydro-2,3,6,10b-tetraaza-benzo[e]azulen-6-yl]-N-isopropyl-N-(6-methoxy-pyridin-3-yl)-acetamide Following the procedure described for Example 1 (A), Step A, 2-(1-cyclohexyl-5-oxo-4,5-dihydro-2,3,6,10b-tetraaza-benzo[e]azulen-6-yl)-N-isopropyl-N-(6-methoxy-pyridin-3-yl)-acetamide (Preparation 8(A)) (90 mg, 0.184 mmol) was condensed with 1H-indole-3-carbaldehyde (32 mg, 0.221 mmol). Purification by medium pressure chromatography eluting with a solvent gradient (10% EtOAc in hexanes to 100% EtOAc) yielded 72.5 mg of 2-[1-cyclohexyl-4-(1H-indol-3-ylmethylene)-5-oxo-4,5-dihydro-2,3,6,10b-tetraaza-benzo[e]azulen-6-yl]-N-isopropyl-N-(6-methoxy-pyridin-3-yl)-acetamide. $^1$H NMR (CDCl$_3$) δ 8.63 (s, 1H), 8.16 (m, 1H), 7.88-7.96 (m, 1H), 7.45-7.76 (m, 2H), 7.12-7.44 (m, 6H), 6.83 (m, 1H), 5.10 (m, 1H), 4.11-4.35 (m, 1H), 3.94 (t, 2H), 3.84 (dd, 1H), 2.94 (m, 1H), 2.25 (m, 1H), 1.99 (m, 2H), 1.70 (m, 6H), 1.35 (m, 3H), 1.15 (m, 6H); MS 616.4 (M+1), 614.3 (M−1).

Step B: 2-[1-Cyclohexyl-4-(1H-indol-3-ylmethyl)-5-oxo-4,5-dihydro-2,3,6,10b-tetraaza-benzo[e]azulen-6-yl]-N-isopropyl-N-(6-methoxy-pyridin-3-yl)-acetamide Following the procedure described for Example 1 (A), Step B, 2-[1-cyclohexyl-4-(1H-indol-3-ylmethylene)-5-oxo-4,5-dihydro-2,3,6,10b-tetraaza-benzo[e]azulen-6-yl]-N-isopropyl-N-(6-methoxy-pyridin-3-yl)-acetamide (72.5 mg, 0.118 mmol) was reduced. Purification by medium pressure chromatography eluting with a solvent gradient (10% EtOAc in hexanes to 100% EtOAc) provided 19.7 mg of 2-[1-cyclohexyl-4-(1H-indol-3-ylmethyl)-5-oxo-4,5-dihydro-2,3,6,10b-tetraaza-benzo[e]azulen-6-yl]-N-isopropyl-N-(6-methoxy-pyridin-3-yl)-acetamide. $^1$H NMR (CDCl$_3$) δ 8.21 (t, 1H), 7.02-8.09 (m, 10H), 6.84 (dd, 1H), 5.02 (m, 1H), 4.18 (t, 1H), 3.56-3.96 (m, 5H), 2.79 (m, 1H), 2.16 (m, 1H), 1.92 (m, 1H), 1.69 (m, 7H), 1.53 (m, 1H), 1.31 (m, 2H), 1.05 (m, 6H); MS 618.7 (M+1).

Example 1(E)

Preparation of 2-[1-(3-Hydroxy-phenyl)-4-(1H-indol-3-ylmethyl)-5-oxo-4,5-dihydro-2,3,6,10b-tetraaza-benzo[e]azulen-6-yl]-N-isopropyl-N-(6-methoxy-pyridin-3-yl)-acetamide

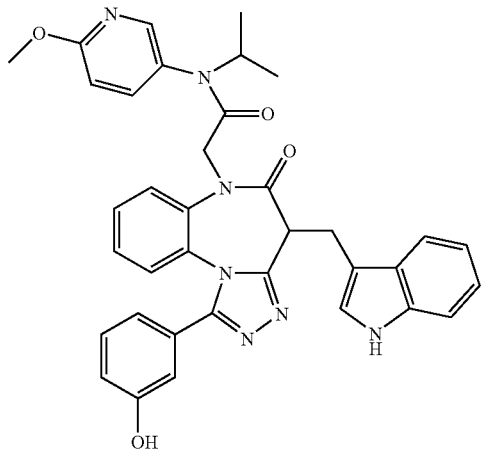

Step A: 2-[1-(3-Benzyloxy-phenyl)-4-(1H-indol-3-ylmethylene)-5-oxo-4,5-dihydro-2,3,6,10b-tetraaza-benzo[e]azulen-6-yl]-N-isopropyl-N-(6-methoxy-pyridin-3-yl)-acetamide Following the procedure described for Example 1 (A), Step A, 2-[1-(3-benzyloxy-phenyl)-5-oxo-4,5-dihydro-2,3,6,10b-tetraaza-benzo[e]azulen-6-yl]-N-isopropyl-N-(6-methoxy-pyridin-3-yl)-acetamide (Preparation 6) (129 mg, 0.219 mmol) was condensed with 1H-indole-3-carbaldehyde (70 mg, 0.48 mmol). Purification by medium pressure chromatography eluting with a solvent gradient (10% EtOAc in hexanes to 100% EtOAc) yielded 60 mg of 2-[1-(3-benzyloxy-phenyl)-4-(1H-indol-3-ylmethylene)-5-oxo-4,5-dihydro-2,3,6,10b-tetraaza-benzo[e]azulen-6-yl]-N-isopropyl-N-(6-methoxy-pyridin-3-yl)-acetamide. $^1$H NMR (CD$_3$OD) δ 8.13 (m, 1H), 7.64 (m, 2H), 7.23-7.48 (m, 13H), 7.13 (m, 3H), 6.93 (m, 2H), 4.94 (m, 2H), 4.85 (m, 1H), 4.63 (m, 1H), 4.20-4.40 (m, 1H), 3.96 (m, 1H), 3.85 (d, 1H), 0.90-1.05 (m, 6H); MS 716.5 (M+1), 714.6 (M−1)

Step B: 2-[1-(3-Hydroxy-phenyl)-4-(1H-indol-3-ylmethyl)-5-oxo-4,5-dihydro-2,3,6,10b-tetraaza-benzo[e]azulen-6-yl]-N-isopropyl-N-(6-methoxy-pyridin-3-yl)-acetamide Following the procedure described for Example 1 (A), Step B, 2-[1-(3-benzyloxy-phenyl)-4-(1H-indol-3-ylmethylene)-5-oxo-4,5-dihydro-2,3,6,10b-tetraaza-benzo[e]azulen-6-yl]-N-isopropyl-N-(6-methoxy-pyridin-3-yl)-acetamide (60 mg, 0.084 mmol) was reduced and deprotected over 48 hours. Purification by medium pressure chromatography eluting with a solvent gradient (10% EtOAc in hexanes to 100% EtOAc) provided 39.5 mg of 2-[1-(3-hydroxy-phenyl)-4-(1H-indol-3-ylmethyl)-5-oxo-4,5-dihydro-2,3,6,10b-tetraaza-benzo[e]azulen-6-yl]-N-isopropyl-N-(6-methoxy-pyridin-3-yl)-acetamide. $^1$H NMR (CD$_3$OD) δ 8.15 (d, 2H), 7.63 (s, 1H), 6.91-7.44 (m, 14H), 4.80-5.05 (m, 2H), 4.10-4.60 (m, 3H), 3.95 (s, 3H), 3.40-3.90 (m, 1H), 1.13 (m, 6H); MS 627 (M+1), 625 (M−1).

Example 1(F)

Preparation of N-Benzyl-2-[8,9-difluoro-4-(5-fluoro-1H-indol-3-ylmethyl)-5-oxo-1-phenyl-4,5-dihydro-2,3,6,10b-tetraaza-benzo[e]azulen-6-yl]-N-isopropyl-acetamide

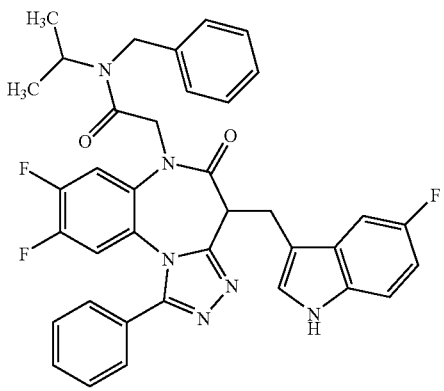

Step A: N-Benzyl-2-[8,9-difluoro-4-(5-fluoro-1H-indol-3-ylmethylene)-5-oxo-1-phenyl-4,5-dihydro-2,3,6,10b-tetraaza-benzo[e]azulen-6-yl]-N-isopropyl-acetamide Following the procedure described for Example 1 (A), Step A, N-benzyl-2-(8,9-difluoro-5-oxo-1-phenyl-4,5-dihydro-2,3,6,10b-tetraaza-benzo[e]azulen-6-yl)-N-isopropyl-acetamide (Preparation 9) (100 mg, 0.198 mmol) was condensed with 5-fluoro-1H-indole-3-carbaldehyde (38.8 mg, 0.238 mmol). Purification by medium pressure chromatography eluting with 50% EtOAc in CH$_2$Cl$_2$ provided 91.5 mg of N-benzyl-2-[8,9-difluoro-4-(5-fluoro-1H-indol-3-ylmethylene)-5-oxo-1-phenyl-4,5-dihydro-2,3,6,10b-tetraaza-benzo[e]azulen-6-yl]-N-isopropyl-acetamide. $^1$H NMR (CDCl$_3$) δ 7.92 (d, 1H), 7.10-7.67 (m, 13H), 6.84 (m, 1H), 6.64 (m, 1H), 4.37-4.97 (m, 5H), 4.20 (m, 1H), 1.20 (m, 6H); MS 647.4 (M+1), 645.3 (M−1).

Step B: N-Benzyl-2-[8,9-difluoro-4-(5-fluoro-1H-indol-3-ylmethyl)-5-oxo-1-phenyl-4,5-dihydro-2,3,6,10b-tetraaza-benzo[e]azulen-6-yl]-N-isopropyl-acetamide Following the procedure described for Example 1 (A), Step B, N-benzyl-2-[8,9-difluoro-4-(5-fluoro-1H-indol-3-ylmethylene)-5-oxo-1-phenyl-4,5-dihydro-2,3,6,10b-tetraaza-benzo[e]azulen-6-yl]-N-isopropyl-acetamide (91.5 mg, 0.140 mmol) was reduced to yield 77.2 mg of N-benzyl-2-[8,9-difluoro-4-(5-fluoro-1H-indol-3-ylmethyl)-5-oxo-1-phenyl-4,5-dihydro-2,3,6,10b-tetraaza-benzo[e]azulen-6-yl]-N-isopropyl-acetamide. $^1$H NMR (CDCl$_3$) δ 8.04 (d, 1H), 7.16-7.60 (m, 13H), 6.85 (m, 1H), 6.66 (m, 1H), 4.34-4.90 (m, 5H), 3.83 (m, 2H), 3.64 (m, 1H), 1.23 (m, 3H), 1.13 (m, 3H); MS 649.5 (M+1), 647.5 (M−1).

Example 1(G)

Preparation of 2-[1-(3-Hydroxy-phenyl)-4-(1H-indol-3-ylmethyl)-5-oxo-4,5-dihydro-2,3,6,10b-tetraaza-benzo[e]azulen-6-yl]-N-isopropyl-N-phenyl-acetamide

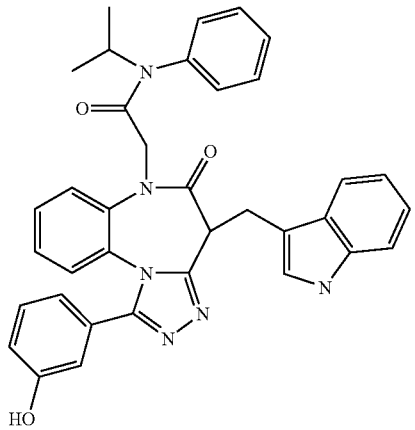

Step A: 2-[1-(3-Hydroxy-phenyl)-4-(1H-indol-3-ylmethylene)-5-oxo-4,5-dihydro-2,3,6,10b-tetraaza-benzo[e]azulen-6-yl]-N-isopropyl-N-phenyl-acetamide Following the procedure described for Example 1 (A), Step A, 2-[1-(3-hydroxy-phenyl)-5-oxo-4,5-dihydro-2,3,6,10b-tetraaza-benzo[e]azulen-6-yl]-N-isopropyl-N-phenyl-acetamide (Preparation 12) (244 mg, 0.522 mmol) was condensed over 48 hours with 1H-indole-3-carbaldehyde (105 mg, 0.723 mmol). Purification by medium pressure chromatography eluting with a solvent gradient (EtOAc to 5% MeOH in EtOAc to 10% MeOH in EtOAc) yielded 177.9 mg of 2-[1-(3-hydroxy-phenyl)-4-(1H-indol-3-ylmethylene)-5-oxo-4,5-dihydro-2,3,6,10b-tetraaza-benzo[e]azulen-6-yl]-N-isopropyl-N-phenyl-acetamide. $^1$H NMR (CD$_3$OD) δ 8.23 (d, 1H), 7.90 (s, 1H), 6.90-7.63 (m, 16H), 4.95 (m, 1H), 3.68-4.50 (m, 3H), 1.11 (m, 6H); MS 595.3 (M+1), 593.3 (M−1).

Step B: 2-[1-(3-Hydroxy-phenyl)-4-(1H-indol-3-ylmethyl)-5-oxo-4,5-dihydro-2,3,6,10b-tetraaza-benzo[e]azulen-6-yl]-N-isopropyl-N-phenyl-acetamide Following the procedure described for Example 1 (A), Step B, 2-[1-(3-hydroxy-phenyl)-4-(1H-indol-3-ylmethylene)-5-oxo-4,5-dihydro-2,3,6,10b-tetraaza-benzo[e]azulen-6-yl]-N-isopropyl-N-phenyl-acetamide (177.9 mg, 0.299 mmol) was reduced over 20 hours and was purified by reverse phase (C-18) high pressure chromatography eluting with a solvent gradient (15% of 0.1% formic acid/CH$_3$CN in 0.1% formic acid/water to 100% of 0.1% formic acid/CH$_3$CN) to yield 77 mg of 2-[1-(3-hydroxy-phenyl)-4-(1H-indol-3-ylmethyl)-5-oxo-4,5-dihydro-2,3,6,10b-tetraaza-benzo[e]azulen-6-yl]-N-isopropyl-N-phenyl-acetamide. $^1$H NMR (CD$_3$OD) δ 7.53 (m, 7H), 7.32 (m, 3H), 7.22 (t, 3H), 6.90-7.03 (m, 5H), 4.82 (m, 2H), 4.45 (d, 1H), 4.12 (d, 1H), 3.93 (d, 1H), 3.76 (d, 1H), 1.04 (m, 6H); MS 597.4 (M+1), 595.5 (M−1).

Example 1(H)

Preparation of N-Benzyl-2-[8,9-difluoro-4-(1H-indol-3-ylmethyl)-5-oxo-1-phenyl-4,5-dihydro-2,3,6,10b-tetraaza-benzo[e]azulen-6-yl]-N-isopropyl-acetamide

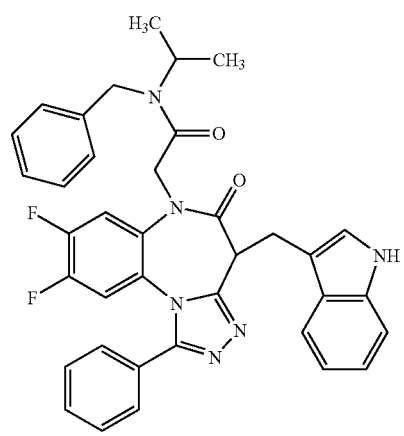

Step A: N-Benzyl-2-[8,9-difluoro-4-(1H-indol-3-ylmethylene)-5-oxo-1-phenyl-4,5-dihydro-2,3,6,10b-tetraaza-benzo[e]azulen-6-yl]-N-isopropyl-acetamide Following the procedure described for Example 1 (A), Step A, N-benzyl-2-(8,9-difluoro-5-oxo-1-phenyl-4,5-dihydro-2,3,6,10b-tetraaza-benzo[e]azulen-6-yl)-N-isopropyl-acetamide (Preparation 9) (200 mg, 0.399 mmol) was condensed over 24 hours with 1H-indole-3-carbaldehyde (70 mg, 0.479 mmol). Purification by medium pressure chromatography eluting with a solvent gradient (CH$_2$Cl$_2$ to 20% acetone in CH$_2$Cl$_2$) provided 190 mg of N-benzyl-2-[8,9-difluoro-4-(1H-indol-3-ylmethylene)-5-oxo-1-phenyl-4,5-dihydro-2,3,6,10b-tetraaza-benzo[e]azulen-6-yl]-N-isopropyl-acetamide. MS 629.3 (M+1), 627.3 (M−1).

Step B: N-Benzyl-2-[8,9-difluoro-4-(1H-indol-3-ylmethyl)-5-oxo-1-phenyl-4,5-dihydro-2,3,6,10b-tetraaza-benzo[e]azulen-6-yl]-N-isopropyl-acetamide Following the procedure described for Example 1 (A), Step B, N-benzyl-2-[8,9-difluoro-4-(1H-indol-3-ylmethylene)-5-oxo-1-phenyl-4,5-dihydro-2,3,6,10b-tetraaza-benzo[e]azulen-6-yl]-N-isopropyl-acetamide (185 mg, 0.294 mmol) was reduced over 24 hours. The reaction was filtered through Celite® and the filtrate was concentrated in vacuo. The residue was dissolved in EtOAc and was washed with aqueous NaHCO$_3$ (1x). The organic solution was dried (Na$_2$SO$_4$), filtered, and concentrated in vacuo. Purification by preparative chromatography eluting with 5% MeOH in CH$_2$Cl$_2$ provided 35 mg of N-benzyl-2-[8,9-difluoro-4-(1H-indol-3-ylmethyl)-5-oxo-1-phenyl-4,5-dihydro-2,3,6,10b-tetraaza-benzo[e]azulen-6-yl]-N-isopropyl-acetamide. $^1$H NMR (CD$_2$Cl$_2$) δ 8.30 (d, 1H), 6.98-7.64 (m, 15H), 6.68 (q, 1H), 4.06-4.90 (m, 5H), 3.73-3.89 (m, 3H), 1.08-1.28 (m, 6H); MS 631.3 (M+1), 629.3 (M−1).

Example 1(I)

Preparation of N-Benzyl-2-[8,9-difluoro-4-(6-fluoro-1H-indol-3-ylmethyl)-5-oxo-1-phenyl-4,5-dihydro-2,3,6,10b-tetraaza-benzo[e]azulen-6-yl]-N-isopropyl-acetamide

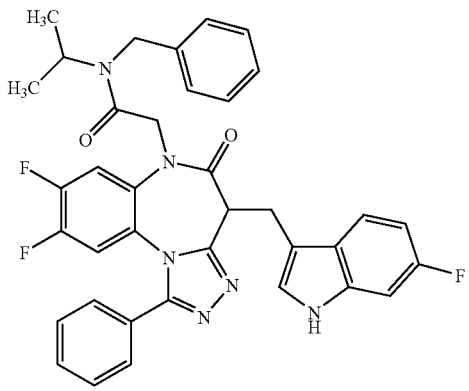

Step A: N-Benzyl-2-[8,9-difluoro-4-(6-fluoro-1H-indol-3-ylmethylene)-5-oxo-1-phenyl-4,5-dihydro-2,3,6,10b-tetraaza-benzo[e]azulen-6-yl]-N-isopropyl-acetamide Following the procedure described for Example 1 (A), Step A, N-benzyl-2-(8,9-difluoro-5-oxo-1-phenyl-4,5-dihydro-2,3,6,10b-tetraaza-benzo[e]azulen-6-yl)-N-isopropyl-acetamide (Preparation 9) (50 mg, 0.099 mmol) was condensed with 6-fluoroindole-3-carboxaldehyde (19.4 mg, 0.119 mmol). Purification by medium pressure chromatography eluting with 50% EtOAc in $CH_2Cl_2$ yielded 23.5 mg of N-benzyl-2-[8,9-difluoro-4-(6-fluoro-1H-indol-3-ylmethylene)-5-oxo-1-phenyl-4,5-dihydro-2,3,6,10b-tetraaza-benzo[e]azulen-6-yl]-N-isopropyl-acetamide. $^1$H NMR ($CDCl_3$) δ 7.94 (d, 1H), 7.61 (m, 3H), 7.27-7.49 (m, 9H), 6.95 (m, 1H), 6.86 (m, 1H), 6.63 (m, 1H), 4.35-5.0 (m, 5H), 4.20 (m, 1H), 1.23 (m, 6H); MS 647.3 (M+1), 645.3 (M−1).

Step B: N-Benzyl-2-[8,9-difluoro-4-(6-fluoro-1H-indol-3-ylmethyl)-5-oxo-1-phenyl-4,5-dihydro-2,3,6,10b-tetraaza-benzo[e]azulen-6-yl]-N-isopropyl-acetamide Following the procedure described for Example 1 (A), Step B, N-benzyl-2-[8,9-difluoro-4-(6-fluoro-1H-indol-3-ylmethylene)-5-oxo-1-phenyl-4,5-dihydro-2,3,6,10b-tetraaza-benzo[e]azulen-6-yl]-N-isopropyl-acetamide (23 mg, 0.035 mmol) was reduced at 80° C. over 24 hours. The reaction was filtered through Celite® and was concentrated in vacuo. The residue was dissolved in EtOAc and the organic solution was washed with aqueous $NaHCO_3$, was dried ($MgSO_4$), filtered and concentrated to provide 22.7 mg of N-benzyl-2-[8,9-difluoro-4-(6-fluoro-1H-indol-3-ylmethyl)-5-oxo-1-phenyl-4,5-dihydro-2,3,6,10b-tetraaza-benzo[e]azulen-6-yl]-N-isopropyl-acetamide. $^1$H NMR ($CDCl_3$) δ 8.40 (s) and 8.28 (s, total 1H), 7.10-7.60 (m, 12H), 6.94 (d, 1H), 6.77 (t, 1H), 6.64 (m, 1H), 4.31-4.95 (m, 5H), 3.61-3.93 (m, 3H), 1.07-1.30 (m, 6H); MS 649.5 (M+1), 647.5 (M−1).

Example 1(J)

Preparation of N-isopropyl-2-[5-oxo-1-phenyl-4-(1H-pyrrolo[2,3-b]pyridin-3-ylmethyl)-4,5-dihydro-2,3,6,10b-tetraaza-benzo[e]azulen-6-yl]-N-phenyl-acetamide

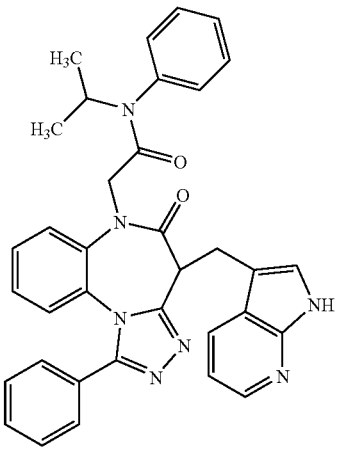

Step A: N-Isopropyl-2-[5-oxo-1-phenyl-4-(1H-pyrrolo[2,3-b]pyridin-3-ylmethylene)-4,5-dihydro-2,3,6,10b-tetraaza-benzo[e]azulen-6-yl]-N-phenyl-acetamide Following the procedure described for Example 1 (A), Step A, N-isopropyl-2-(5-oxo-1-phenyl-4,5-dihydro-2,3,6,10b-tetraaza-benzo[e]azulen-6-yl)-N-phenyl-acetamide (Preparation 7(A)) (500 mg, 1.10 mmol) was condensed with 1H-pyrrolo[2,3-b]pyridine-3-carbaldehyde (160 mg, 1.16 mmol) in pyridine (5 mL). Purification by medium pressure chromatography eluting with a solvent gradient (5% acetone in $CH_2Cl_2$ to 50% acetone in $CH_2Cl_2$ to 10% MeOH in $CH_2Cl_2$) yielded 300 mg of N-isopropyl-2-[5-oxo-1-phenyl-4-(1H-pyrrolo[2,3-b]pyridin-3-ylmethylene)-4,5-dihydro-2,3,6,10b-tetraaza-benzo[e]azulen-6-yl]-N-phenyl-acetamide. $^1$H NMR ($CDCl_3$) δ 8.31 (d, 1H), 8.05 (d) and 7.96 (d, total 1H), 7.71 (m, 1H), 7.59 (m, 2H), 7.33-7.51 (m, 9H), 7.17 (m, 2H), 7.01 (m, 1H), 6.80 (t, 1H), 5.09 (m, 1H), 4.50 (d) and 4.30 (d, total 1H), 4.15 (m, 1H), 3.92 (d, 1H), 1.14 (m, 6H); MS 580.6 (M+1).

Step B: N-Isopropyl-2-[5-oxo-1-phenyl-4-(1H-pyrrolo[2,3-b]pyridin-3-ylmethyl)-4,5-dihydro-2,3,6,10b-tetraaza-benzo[e]azulen-6-yl]-N-phenyl-acetamide Following the procedure described for Example 1 (A), Step B, N-isopropyl-2-[5-oxo-1-phenyl-4-(1H-pyrrolo[2,3-b]pyridin-3-ylmethylene)-4,5-dihydro-2,3,6,10b-tetraaza-benzo[e]azulen-6-yl]-N-phenyl-acetamide (300 mg, 0.518 mmol) was reduced at 60° C. for 6.5 hours. The reaction was filtered through Celite® and was concentrated in vacuo. The residue was dissolved in EtOAc and the organic solution was washed with water (1×). The organic solution was dried ($Na_2SO_4$), filtered, and concentrated in vacuo. Purification using reverse phase (C-18) high pressure chromatography eluting with a solvent gradient over 6 minutes (35% of 0.1% $NH_4OH/CH_3CN$ in 0.1% of $NH_4OH/H_{20}$ to 100% of 0.1%

NH$_4$OH/CH$_3$CN) provided 100 mg of N-isopropyl-2-[5-oxo-1-phenyl-4-(1H-pyrrolo[2,3-b]pyridin-3-ylmethyl)-4,5-dihydro-2,3,6,10b-tetraaza-benzo[e]azulen-6-yl]-N-phenyl-acetamide. $^1$H NMR (CDCl$_3$) δ 8.22 (d, 1H), 8.00 (d, 1H), 7.55 (m, 3H), 7.32-7.48 (m, 9H), 7.18 (m, 1H), 7.05 (m, 2H), 6.85 (d, 1H), 4.97 (m, 1H), 4.27 (d, 1H), 4.06 (m, 1H), 3.87 (d, 2H), 3.70 (t, 1H), 1.09 (m, 6H); MS 582.6 (M+1), 580.5 (M−1).

Example 1(K)

Preparation of (−)—N-Benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide, enantiomer 1

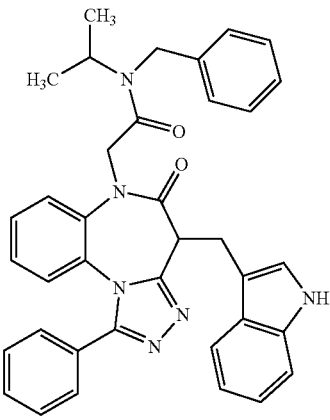

Step A: N-Benzyl-2-[4-(1H-indol-3-ylmethylene)-5-oxo-1-phenyl-4,5-dihydro-2,3,6,10b-tetraaza-benzo[e]azulen-6-yl]-N-isopropyl-acetamide Following the procedure described for Example 1 (A), Step A, N-benzyl-N-isopropyl-2-(5-oxo-1-phenyl-4,5-dihydro-2,3,6,10b-tetraaza-benzo[e]azulen-6-yl)-acetamide (Preparation 10) (13.9 g, 29.8 mmol) was condensed with 1H-indole-3-carbaldehyde (5.2 g, 35.8 mmol) for 48 hours. The volatiles were concentrated in vacuo to provide 18.5 g of N-benzyl-2-[4-(1H-indol-3-ylmethylene)-5-oxo-1-phenyl-4,5-dihydro-2,3,6,10b-tetraaza-benzo[e]azulen-6-yl]-N-isopropyl-acetamide. $^1$H NMR (CDCl$_3$) δ 8.01 (d, 1H), 7.67-7.50 (m, 4H), 7.43-7.11 (m, 12H), 6.99 (m, 1H), 6.99 (m, 1H), 6.80 (m, 1H), 4.96 (m, 1H), 4.71-4.49 (m, 4H), 4.23 (m, 1H), 1.20 (m, 6H); MS 593.3 (M+1).

Step B: N-Benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide Following the procedure described for Example 1 (A), Step B, N-benzyl-2-[4-(1H-indol-3-ylmethylene)-5-oxo-1-phenyl-4,5-dihydro-2,3,6,10b-tetraaza-benzo[e]azulen-6-yl]-N-isopropyl-acetamide (18.5 g, 31.2 mmol) was reduced at 60° C. over 24 hours. The reaction was filtered through Celite® and was concentrated in vacuo. The residue was dissolved in CH$_2$Cl$_2$ and the organic solution was washed with water. The organic layer was dried (Na$_2$SO$_4$), filtered and concentrated in vacuo. The residue was dissolved in toluene and was stirred at 60° C. for 24 h. The solids were filtered to provide 12.4 g of N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide as a racemic mixture. $^1$H NMR (CDCl$_3$) δ 8.02 (d, 1H), 7.57 (d, 3H), 7.46-7.23 (m, 8H), 7.17-7.01 (m, 6H), 6.83 (dd, 1H), 4.96-4.40 (m, 5H), 4.17-3.89 (m, 2H), 3.80 (m) and 3.72 (m, total 1H), 1.20 (dd, 3H), 1.13 (dd, 3H); MS 595.3 (M+1).

Step C: (−)—N-Benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide, enantiomer 1

The racemic product of Step B, N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide (13.56 g, 22.8 mmol), was separated into its enantiomers by high pressure chromatography using a (S,S)-Whelk-O 1 column (5 cm×25 cm), eluting with heptane in EtOH (60:40), using a flow rate of 140 mL/minute to give enantiomer 1 having a retention time of 17 minutes. The active enantiomer (enantiomer 1) was dissolved in CH$_2$Cl$_2$ and the organic solution was washed with aqueous NaHCO$_3$ (1×) and brine (1×). The organic solution was dried (Na$_2$SO$_4$), filtered and concentrated to provide 6.4 g of (−)—N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide (enentiomer 1). A mixture of the solid (6.4 g, 10.77 mmol) in EtOH (250 mL) was heated at 45° C. for 96 hours, slowly cooled to room temperature over 4 hours, filtered and washed with minimal amount of EtOH to provide 5 g of crystalline (−)—N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide (enantiomer 1), mp 244-245° C. $^1$H NMR (DMSO-d$_6$) δ 10.79-10.77 (d, 1H), 7.76-7.74 (d, 1H), 7.56-7.24 (m, 7H), 7.20-7.12 (m, 5H), 7.02-6.91 (m, 2H), 6.91-6.83 (m, 2H), 5.20 (m, 0.5H), 4.95 to 4.83 (m, 1H), 4.60-4.51 (m, 2H), 4.47 (m, 0.5H), 4.25-4.21 (m, 1H), 3.84-3.78 (m, 2H), 3.64-3.58 (m, 2H), 1.12-1.10 (d, 1.7H), 1.00-0.99 (d, 1.7H), 0.94-0.92 (d, 2.6H); [α]$_D^{20}$ −49.3 (c 1, ethanol).

Example 2(A)

Preparation of N-(6-Chloro-pyridin-3-yl)-2-[4-(1H-indol-3-ylmethyl)-5-oxo-1-phenyl-4,5-dihydro-2,3,6,10b-tetraaza-benzo[e]azulen-6-yl]-N-isopropyl-acetamide

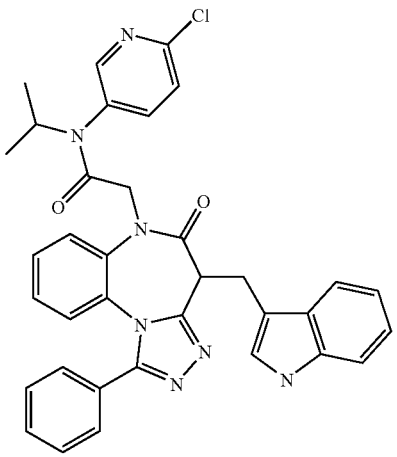

To a solution of [4-(1H-indol-3-ylmethyl)-5-oxo-1-phenyl-4,5-dihydro-2,3,6,10b-tetraaza-benzo[e]azulen-6-yl]-acetic acid (Preparation 15) (30 mg, 0.06 mmol) and (6-chloro-pyridin-3-yl)-isopropyl-amine (Preparation 2(A)) (10.1 mg, 0.06 mmol) in benzene (2 mL) was added $PCl_3$ (2.0 M in $CH_2Cl_2$, 0.1 mL, 0.198 mmol) and the reaction was heated at reflux for 24 hours. The reaction was cooled to room temperature and was diluted with $CH_2Cl_2$. The organic solution was washed consecutively with aqueous $NaHCO_3$ (1×), water (1×), 1N HCl (1×), and water (1×). The organic solution was dried ($MgSO_4$) and the volatiles were concentrated in vacuo. The residue was purified by medium pressure chromatography eluting with 10% EtOH in $CH_2Cl_2$ to yield 5 mg of N-(6-chloro-pyridin-3-yl)-2-[4-(1H-indol-3-ylmethyl)-5-oxo-1-phenyl-4,5-dihydro-2,3,6,10b-tetraaza-benzo[e]azulen-6-yl]-N-isopropyl-acetamide. $^1$H NMR ($CDCl_3$) δ 8.26 (s, 1H), 8.17 (s, 1H), 7.76-7.29 (m, 11H), 7.06 (m, 3H), 6.83 (d, 1H), 5.04-4.87 (m, 1H), 4.45-4.15 (m, 1H), 3.94-3.82 (m, 3H), 3.72 (m, 1H), 0.06 (s, 6H); MS 616.6 (M+1), 614.5 (M−1).

Example 2(B)

Preparation of N-(6-Ethoxy-pyridin-3-yl)-2-[4-(1H-indol-3-ylmethyl)-5-oxo-1-phenyl-4,5-dihydro-2,3,6,10b-tetraaza-benzo[e]azulen-6-yl]-N-isopropyl-acetamide

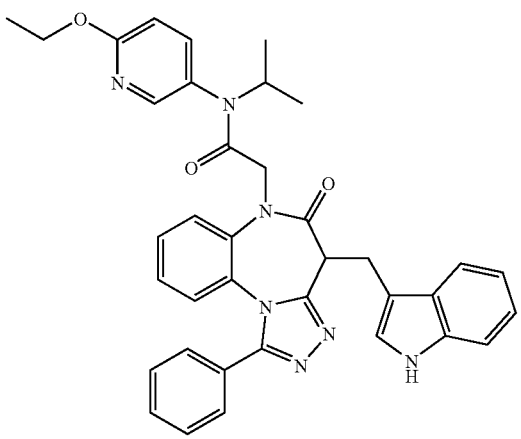

Following the procedure described for Example 2(A), [4-(1H-indol-3-ylmethyl)-5-oxo-1-phenyl-4,5-dihydro-2,3,6,10b-tetraaza-benzo[e]azulen-6-yl]-acetic acid (Preparation 15) (300 mg, 0.65 mmol) was reacted with (6-ethoxy-pyridin-3-yl)-isopropyl-amine (Preparation 2(B)) (117 mg, 0.65 mmol) and $PCl_3$ in dichloroethane at 100° C. Purification by medium pressure chromatography eluting with a solvent gradient (5% of 0.5% $NH_4OH$/MeOH in $CH_2Cl_2$ to 10% of 0.5% $NH_4OH$/MeOH in $CH_2Cl_2$) provided 85.1 mg of N-(6-ethoxy-pyridin-3-yl)-2-[4-(1H-indol-3-ylmethyl)-5-oxo-1-phenyl-4,5-dihydro-2,3,6,10b-tetraaza-benzo[e]azulen-6-yl]-N-isopropyl-acetamide. $^1$H NMR ($CD_3OD$) δ 8.05 (d, 1H), 7.62 (m, 3H), 7.38-7.52 (m, 6H), 7.24 (d, 1H), 7.11 (m, 2H), 6.99 (t, 1H), 6.89 (m, 3H), 4.78 (m, 1H), 4.53 (m, 1H), 4.35 (q, 2H), 4.12 (m, 1H), 3.88 (t, 1H), 3.78 (dd, 1H), 3.69 (dd, 1H), 1.38 (t, 3H), 0.99 (m, 6H); MS 626.7 (M+1), 624.6 (M−1).

Example 3(A)

Preparation of 2-[4-(1H-Indazol-3-ylmethyl)-5-oxo-1-Phenyl-4,5-dihydro-2,3,6,10b-tetraaza-benzo[e]azulen-6-yl]-N-isopropyl-N-(6-methoxy-pyridin-3-yl)-acetamide

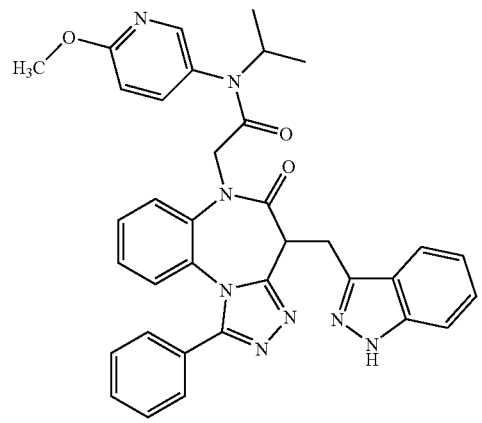

Step A: 3-(6-{[Isopropyl-(6-methoxy-pyridin-3-yl)-carbamoyl]-methyl}-5-oxo-1-phenyl-5,6-dihydro-4H-2,3,6,10b-tetraaza-benzo[e]azulen-4-ylmethyl)-indazole-1-carboxylic acid tert-butyl ester To a solution of N-isopropyl-N-(6-methoxy-pyridin-3-yl)-2-(5-oxo-1-phenyl-4,5-dihydro-2,3,6,10b-tetraaza-benzo[e]azulen-6-yl)-acetamide (Preparation 11) (520 mg, 1.079 mmol) in DMF (10 mL) at 0° C. was added NaH (60% in oil, 50 mg, 1.27 mmol). The reaction was stirred at 0° C. for 45 minutes and 3-bromomethyl-indazole-1-carboxylic acid tert-butyl ester (423 mg, 1.36 mmol) in DMF (5 mL) was added. The reaction was stirred at room temperature for 24 hours and was diluted with brine. The aqueous solution was washed with EtOAc (3×). The combined organic solutions were washed with brine (1×), dried ($MgSO_4$), filtered and concentrated in vacuo to provide 3-(6-{[isopropyl-(6-methoxy-pyridin-3-yl)-carbamoyl]-methyl}-5-oxo-1-phenyl-5,6-dihydro-4H-2,3,6,10b-tetraaza-benzo[e]azulen-4-ylmethyl)-indazole-1-carboxylic acid tert-butyl ester. $^1$H NMR ($CD_3OD$) δ 8.05 (d, 1H), 6.80-7.75 (m, 15H), 4.75 (m) and 4.60 (t, total 3H), 3.85-4.20 (m, 6H), 1.65 (m, 9H), 0.98 (m, 6H); MS 713.6 (M+1), 711.5 (M−1).

Step B: 2-[4-(1H-Indazol-3-ylmethyl)-5-oxo-1-phenyl-4,5-dihydro-2,3,6,10b-tetraaza-benzo[e]azulen-6-yl]-N-isopropyl-N-(6-methoxy-pyridin-3-yl)-acetamide The product of Step A, 3-(6-{[isopropyl-(6-methoxy-pyridin-3-yl)-carbamoyl]-methyl}-5-oxo-1-phenyl-5,6-dihydro-4H-2,3,6,10b-tetraaza-benzo[e]azulen-4-ylmethyl)-indazole-1-carboxylic acid tert-butyl ester, was dissolved in $CH_2Cl_2$ (8 mL) and TFA (2 mL) was added. The reaction was stirred at room temperature for 24 hours and was concentrated in vacuo. Purification by medium pressure chromatography eluting with a solvent gradient (1% MeOH in EtOAc to 5% MeOH in EtOAc) provided 172 mg of 2-[4-(1H-indazol-3-ylmethyl)-5-oxo-1-phenyl-4,5-dihydro-2,3,6,10b-tetraaza-benzo[e]azulen-6-yl]-N-isopropyl-N-(6- methoxy-pyridin-3-yl)-acetamide. ¹H NMR (CD₃OD) δ 8.04 (d, 1H), 7.88 (d, 1H), 7.64 (m, 2H), 7.56 (d, 2H), 7.49 (t, 2H), 7.39 (q, 3H), 7.31 (t, 1H), 7.19 (t, 1H), 7.11 (t, 1H), 6.95 (d, 1H), 6.86 (m, 1H), 4.72 (m, 1H), 4.59 (m, 1H), 4.41 (t, 1H), 3.99-4.12 (m, 2H), 3.90 (m, 4H), 0.95 (m, 6H); MS 613.8 (M+1), 611.5 (m−1).

Example 3(B)

Preparation of 2-[4-(1H-Indazol-3-ylmethyl)-5-oxo-1-phenyl-4,5-dihydro-2,3,6,10b-tetraaza-benzo[e]azulen-6-yl]-N-isopropyl-N-phenyl-acetamide

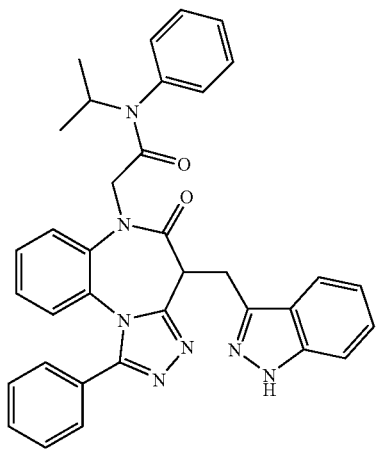

Step A: 3-{6-[(Isopropyl-phenyl-carbamoyl)-methyl]-5-oxo-1-phenyl-5,6-dihydro-4H-2,3,6,10b-tetraaza-benzo[e]azulen-4-ylmethyl}-indazole-1-carboxylic acid tert-butyl ester Following the procedure described for Example 3(A), Step A, N-isopropyl-2-(5-oxo-1-phenyl-4,5-dihydro-2,3,6,10b-tetraaza-benzo[e]azulen-6-yl)-N-phenyl-acetamide (Preparation 7(A)) (411.7 mg, 0.9118 mmol) was alkylated with 3-bromomethyl-indazole-1-carboxylic acid tert-butyl ester (309 mg, 0.993 mmol). Purification by medium pressure chromatography eluting with a solvent gradient (EtOAc to 5% MeOH in EtOAc) provided 391.9 mg of 3-{6-[(isopropyl-phenyl-carbamoyl)-methyl]-5-oxo-1-phenyl-5,6-dihydro-4H-2,3,6,10b-tetraaza-benzo[e]azulen-4-ylmethyl}-indazole-1-carboxylic acid tert-butyl ester. ¹H NMR (CD₃OD) δ 7.99 (m, 2H), 7.22-7.66 (m, 15H), 7.01 (dd, 1H), 4.53-4.81 (m, 3H), 3.88-4.21 (M, 3H), 1.65 (m, 9H), 0.94 (m, 6H).

Step B: 2-[4-(1H-Indazol-3-ylmethyl)-5-oxo-1-phenyl-4,5-dihydro-2,3,6,10b-tetraaza-benzo[e]azulen-6-yl]-N-isopropyl-N-phenyl-acetamide To a solution of 3-{6-[(isopropyl-phenyl-carbamoyl)-methyl]-5-oxo-1-phenyl-5,6-dihydro-4H-2,3,6,10b-tetraaza-benzo[e]azulen-4-ylmethyl}-indazole-1-carboxylic acid tert-butyl ester (391.9 mg, 0.674 mmol) in dioxane (8 mL) was added 4M HCl in dioxane (6 mL). The reaction was stirred at room temperature for 24 hours and was diluted with EtOAc. The organic solution was washed with aqueous NaHCO₃ and brine, was dried (MgSO₄), filtered and concentrated in vacuo. Purification by medium pressure chromatography eluting with a solvent gradient (EtOAc to 10% MeOH in EtOAc) provided 260.9 mg of 2-[4-(1H-indazol-3-ylmethyl)-5-oxo-1-phenyl-4,5-dihydro-2,3,6,10b-tetraaza-benzo[e]azulen-6-yl]-N-isopropyl-N-phenyl-acetamide as a racemic mixture. ¹H NMR (CD₃OD) δ 7.90 (d, 1H), 7.65 (d, 2H), 7.34-7.54 (m, 12H), 7.22 (t, 1H), 7.13 (t, 1H), 6.99 (d, 1H), 4.74 (m, 1H), 465 (d, 1H), 4.42 (t, 1H), 3.92-4.12 (m, 3H), 0.99 (m, 6H); MS 582.7 (M+1), 580.4 (M−1).

Alternative Preparation

Step A: N-Isopropyl-2-(5-oxo-1-phenyl-4,5-dihydro-2,3,6,10b-tetraaza-benzo[e]azulen-6-yl)-N-phenyl-acetamide To a solution of 1-phenyl-4H,6H-2,3,6,10b-tetraaza-benzo[e]azulen-5-one (Preparation 4(A)) (2.5 g, 9.05 mmol) in DMF (40 mL) at 0° C. was added sodium hydride (60% in oil, 0.36 g, 9.0 mmol). The reaction was warmed to room temperature and was stirred for 40 minutes. The reaction was cooled to −6° C. and a solution of 2-bromo-N-isopropyl-N-phenyl-acetamide (Preparation 1(A)) (2.55 g, 9.95 mmol) in DMF (20 mL) was added to the reaction mixture dropwise over 0.5 hour, maintaining the internal reaction temperature below −3° C. The reaction mixture was stirred for 105 minutes below −3° C. and brine (200 mL) was added. The aqueous solution was washed with ethyl acetate (200 mL). The organic layer was washed with brine, dried over sodium sulfate, and concentrated to ⅓ volume. Hexanes were slowly added until a solid crashed out. The white solid was collected by filtration and was rinsed with ether and hexanes to give 2.96 g of N-isopropyl-2-(5-oxo-1-phenyl-4,5-dihydro-2,3,6,10b-tetraaza-benzo[e]azulen-6-yl)-N-phenyl-acetamide. MS 452 (M+1). This intermediate was carried forward according to Example 3(B), Steps A and B above to afford 2-[4-(1H-indazol-3-ylmethyl)-5-oxo-1-phenyl-4,5-dihydro-2,3,6,10b-tetraaza-benzo[e]azulen-6-yl]-N-isopropyl-N-phenyl-acetamide as a racemic mixture.

Example 3(C)

Preparation of (−) 2-[4-(1H-Indazol-3-ylmethyl)-5-oxo-1-phenyl-4,5-dihydro-2,3,6,10b-tetraaza-benzo[e]azulen-6-yl]-N-isopropyl-N-phenyl-acetamide, enantiomer 2

Racemic 2-[4-(1H-indazol-3-ylmethyl)-5-oxo-1-phenyl-4,5-dihydro-2,3,6,10b-tetraaza-benzo[e]azulen-6-yl]-N-isopropyl-N-phenyl-acetamide (Example 3(B)) was separated into its enantiomers using a Chiralcel OD column (10 cm×50 cm), eluting with heptane/ethanol (3:1) containing 0.05% diethylamine, using a flow rate of 250 mL/minute, to provide (−) 2-[4-(1H-indazol-3-ylmethyl)-5-oxo-1-phenyl-4,5-dihydro-2,3,6,10b-tetraaza-benzo[e]azulen-6-yl]-N-isopropyl-N-phenyl-acetamide (enantiomer 2) having a retention time of 9.21 minutes. ¹H NMR (CD₂Cl₂) δ 7.94 (d, 1H), 7.62 (d, 2H), 7.34-7.47 (m, 10H), 7.10-7.22 (m, 4H), 6.89 (d, 1H), 4.84 (m, 1H), 4.41 (br d, 1H), 4.35 (t, 1H), 3.93-4.11 (m, 3H), 1.00 (m, 6H); MS 582.5 (M+1); $[\alpha]_D^{20}$ −109.6 (c 1.1, ethanol).

Example 3(D)

Preparation of N-Benzyl-2-[8,9-difluoro-4-(1H-indazol-3-ylmethyl)-5-oxo-1-phenyl-4,5-dihydro-2,3,6,10b-tetraaza-benzo[e]azulen-6-yl]-N-isopropyl-acetamide

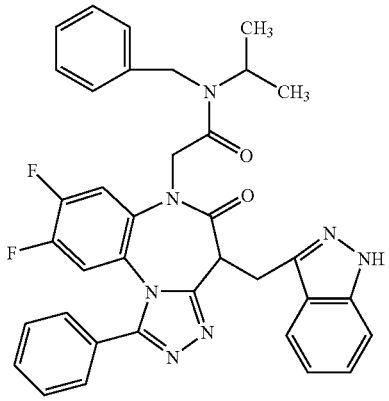

Step A: 3-{6-[(Benzyl-isopropyl-carbamoyl)-methyl]-8,9-difluoro-5-oxo-1-phenyl-5,6-dihydro-4H-2,3,6,10b-tetraaza-benzo[e]azulen-4-ylmethyl}-indazole-1-carboxylic acid tert-butyl ester Following the procedure described in Example 3(A), Step A, N-benzyl-2-(8,9-difluoro-5-oxo-1-phenyl-4,5-dihydro-2,3,6,10b-tetraaza-benzo[e]azulen-6-yl)-N-isopropyl-acetamide (Preparation 9) (200 mg, 0.399 mmol) was alkylated with 3-bromomethyl-indazole-1-carboxylic acid tert-butyl ester (136 mg, 0.439 mmol). The reaction was diluted with a pH 6.8 buffer solution and the aqueous solution was extracted with EtOAc. The organic solution was washed with brine (4×), dried (Na$_2$SO$_4$), filtered and concentrated in vacuo. Purification by medium pressure chromatography eluting with a solvent gradient (CH$_2$Cl$_2$ to 30% MeOH in CH$_2$Cl$_2$) provided 100 mg of 3-{6-[(benzyl-isopropyl-carbamoyl)-methyl]-8,9-difluoro-5-oxo-1-phenyl-5,6-dihydro-4H-2,3,6,10b-tetraaza-benzo[e]azulen-4-ylmethyl}-indazole-1-carboxylic acid tert-butyl ester. MS 732.5 (M+1), 730.4 (M−1).

Step B: N-Benzyl-2-[8,9-difluoro-4-(1H-indazol-3-ylmethyl)-5-oxo-1-phenyl-4,5-dihydro-2,3,6,10b-tetraaza-benzo[e]azulen-6-yl]-N-isopropyl-acetamide To a solution of 3-{6-[(benzyl-isopropyl-carbamoyl)-methyl]-8,9-difluoro-5-oxo-1-phenyl-5,6-dihydro-4H-2,3,6,10b-tetraaza-benzo[e]azulen-4-ylmethyl}-indazole-1-carboxylic acid tert-butyl ester (100 mg, 0.137 mmol) in dioxane (1 mL) was added HCl (4.0M in dioxane, 2 mL). The reaction was stirred at room temperature for 24 hours. The volatiles were concentrated in vacuo and the residue was dissolved in CH$_2$Cl$_2$. The organic solution was washed with aqueous NaHCO$_3$ (1×), dried (Na$_2$SO$_4$), filtered and concentrated in vacuo. Purification by preparative chromatography eluting with 5% MeOH in CH$_2$Cl$_2$ provided 45 mg of N-benzyl-2-[8,9-difluoro-4-(1H-indazol-3-ylmethyl)-5-oxo-1-phenyl-4,5-dihydro-2,3,6,10b-tetraaza-benzo[e]azulen-6-yl]-N-isopropyl-acetamide. $^1$H NMR (CD$_2$Cl$_2$) δ 7.92 (m, 1H), 7.04-7.66 (m, 14H), 6.67 (s, 1H), 4.22-4.96 (m, 6H), 3.91-4.13 (m, 2H), 1.01-1.22 (m, 6H); MS 632.3 (M+1), 630.2 (M−1).

Example 3(E)

Preparation of (−) N-Benzyl-2-[4-(1H-indazol-3-ylmethyl)-5-oxo-1-phenyl-4,5-dihydro-2,3,6,10b-tetraaza-benzo[e]azulen-6-yl]-N-isopropyl-acetamide, enantiomer 2

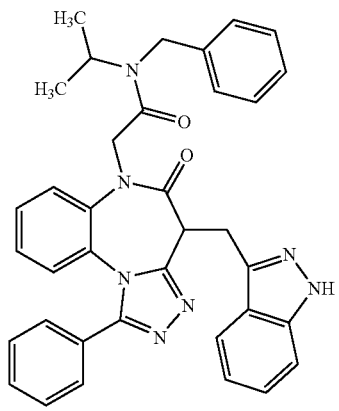

Step A: 3-{6-[(Benzyl-isopropyl-carbamoyl)-methyl]-5-oxo-1-phenyl-5,6-dihydro-4H-2,3,6,10b-tetraaza-benzo[e]azulen-4-ylmethyl}-indazole-1-carboxylic acid tert-butyl ester Following the procedure described in Example 3(A), Step A, N-benzyl-N-isopropyl-2-(5-oxo-1-phenyl-4,5-dihydro-2,3,6,10b-tetraaza-benzo[e]azulen-6-yl)-acetamide (Preparation 10) (210 mg, 0.451 mmol) was alkylated with 3-bromomethyl-indazole-1-carboxylic acid tert-butyl ester (150 mg, 0.473 mmol). The reaction was diluted with a pH 6.8 buffer solution and the aqueous solution was washed with EtOAc. The organic solution was washed with brine (3×), dried (Na$_2$SO$_4$), filtered and concentrated in vacuo. The residue was purified (2×) by preparative chromatography eluting with 5% acetone in CH$_2$Cl$_2$ followed by medium pressure chromatography eluting with a solvent gradient (2% acetone in CH$_2$Cl$_2$ to 14% acetone in CH$_2$Cl$_2$) to provide 19.1 mg of 3-{6-[(benzyl-isopropyl-carbamoyl)-methyl]-5-oxo-1-phenyl-5,6-dihydro-4H-2,3,6,10b-tetraaza-benzo[e]azulen-4-ylmethyl}-indazole-1-carboxylic acid tert-butyl ester. $^1$H NMR (CD$_2$Cl$_2$) δ 8.05 (m, 1H), 7.12-7.71 (m, 15H), 7.03 (m, 1H), 6.92 (d, 1H), 5.21 (d) and 4.90 (d, total 1H), 4.61-4.72 (m, 2H), 4.49 (s, 1H), 4.43 (t, 1H), 4.25-4.32 (m, 1H), 3.96-4.15 (m, 2H), 1.61 (d, 9H), 1.16 (dd, 3H), 1.04 (dd, 3H); MS 696.4 (M+1).

Step B: N-Benzyl-2-[4-(1H-indazol-3-ylmethyl)-5-oxo-1-phenyl-4,5-dihydro-2,3,6,10b-tetraaza-benzo[e]azulen-6-yl]-N-isopropyl-acetamide Following the procedure described in Example 3(B), Step B, 3-{6-[(benzyl-isopropyl-carbamoyl)-methyl]-5-oxo-1-phenyl-5,6-dihydro-4H-2,3,6,10b-tetraaza-benzo[e]azulen-4-ylmethyl}-indazole-1-carboxylic acid tert-butyl ester (19.1 mg, 0.274 mmol) was deprotected with HCl (4.0M in dioxane, 0.8 mL) over 24 hours. The reaction was diluted with EtOAc, and the organic solution was washed with aqueous NaHCO$_3$ (1×), dried (Na$_2$SO$_4$), filtered and concentrated. Purification by preparative chromatography eluting with 5% MeOH in CH$_2$Cl$_2$ provided 8.5 mg of N-benzyl-2-[4-(1H-indazol-3-ylmethyl)-5-oxo-1-phenyl-4,5-dihydro-2,3,6,10b-tetraaza-benzo[e]azulen-6-yl]-N-isopropyl-acetamide as a racemic mixture. $^1$H NMR (CD$_2$Cl$_2$) δ 7.97 (t, 1H), 7.12-7.64 (m, 15H), 7.05 (m, 1H), 6.92 (m, 1H), 5.08 (d) and 4.81 (d, total 1H), 4.60-4.74 (m, 2H), 4.49 (s, 1H), 4.45 (t, 1H), 4.29-4.39 (m, 1H), 3.96-4.13 (m, 2H), 1.16 (dd, 3H), 1.05 (dd, 3H); MS 596.2 (M+1), 594.2 (M−1).

Step C: (−) N-Benzyl-2-[4-(1H-indazol-3-ylmethyl)-5-oxo-1-phenyl-4,5-dihydro-2,3,6,10b-tetraaza-benzo[e]azulen-6-yl]-N-isopropyl-acetamide, enantiomer 2

The racemic product of Step B, N-benzyl-2-[4-(1H-indazol-3-ylmethyl)-5-oxo-1-phenyl-4,5-dihydro-2,3,6,10b-tetraaza-benzo[e]azulen-6-yl]-N-isopropyl-acetamide (1.57 g, 2.64 mmol), was separated into its enantiomers using a Chiralcel OD column (10 cm×25 cm), eluting with 50% EtOH in heptane, using a flow rate of 250 mL/minute. The enantiomer having a retention time of 17.396 minutes (enantiomer 2) was dissolved in CH$_2$Cl$_2$ and the organic solution was washed with aqueous NaHCO$_3$ (1×) and brine (1×). The organic solution was dried (Na$_2$SO$_4$), filtered and concentrated to provide 660 mg of (−) N-benzyl-2-[4-(1H-indazol-3-ylmethyl)-5-oxo-1-phenyl-4,5-dihydro-2,3,6,10b-tetraaza-benzo[e]azulen-6-yl]-N-isopropyl-acetamide (enantiomer 2). $^1$H NMR (CD$_2$Cl$_2$) δ 7.97 (t, 1H), 7.12-7.65 (m, 15H), 7.05 (m, 1H), 6.92 (m, 1H), 5.10 (d) and 4.82 (d, total 1H), 4.60-4.73 (m, 2H), 4.49 (s, 1H), 4.45 (t, 1H), 4.29-4.38 (m, 1H), 3.96-4.13 (m, 2H), 1.16 (dd, 3H), 1.05 (dd, 3H); MS 597.1 (M+1), 594.0 (M−1); [α]$_D^{20}$ −145.3 (c 1.01, ethanol).

Example 4

Preparation of 2-[4-(1H-Indol-3-ylmethyl)-4-methyl-5-oxo-1-phenyl-4,5-dihydro-2,3,6,10b-tetraaza-benzo[e]azulen-6-yl]-N-isopropyl-N-phenyl-acetamide

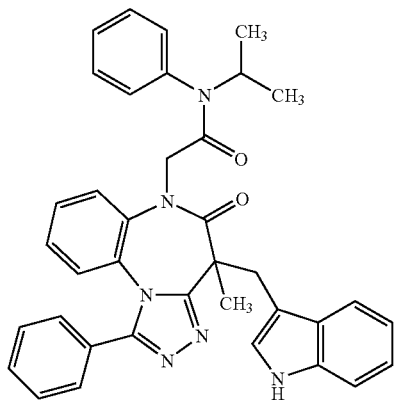

Step A: 3-{6-[(Isopropyl-phenyl-carbamoyl)-methyl]-5-oxo-1-phenyl-5,6-dihydro-4H-2,3,6,10b-tetraaza-benzo[e]azulen-4-ylmethyl}-indole-1-carboxylic acid tert-butyl ester To a solution of 2-[4-(1H-indol-3-ylmethyl)-5-oxo-1-phenyl-4,5-dihydro-2,3,6,10b-tetraaza-benzo[e]azulen-6-yl]-N-isopropyl-N-phenyl-acetamide (Example 6(A)) (250 mg, 0.431 mmol) in CH$_2$Cl$_2$ (6 mL) at 0° C. was added DMAP (5 mg, 0.0431 mmol) and a solution of di-tert-butyl dicarbonate (103 mg, 0.47 mmol) in CH$_2$Cl$_2$ (3 mL). The reaction was stirred at room temperature for 4.5 hours. The reaction was diluted with water and the organic layer was dried (Na$_2$SO$_4$), filtered and concentrated. Purification by medium pressure chromatography eluting with a solvent gradient (10% acetone in CH$_2$Cl$_2$ to 40% acetone in CH$_2$Cl$_2$) provided 290 mg of 3-{6-[(isopropyl-phenyl-carbamoyl)-methyl]-5-oxo-1-phenyl-5,6-dihydro-4H-2,3,6,10b-tetraaza-benzo[e]azulen-4-ylmethyl}-indole-1-carboxylic acid tert-butyl ester. $^1$H NMR (CDCl$_3$) δ 7.33-8.10 (m, 15H), 6.90-7.20 (m, 4H), 4.15-4.90 (m, 2H), 3.65-4.05 (m, 4H), 1.63 (m, 9H), 0.97 (m, 6H); MS 681.2 (M+1).

Step B: 3-{6-[(Isopropyl-phenyl-carbamoyl)-methyl]-4-methyl-5-oxo-1-phenyl-5,6-dihydro-4H-2,3,6,10b-tetraaza-benzo[e]azulen-4-ylmethyl}-indole-1-carboxylic acid tert-butyl ester To a solution of 3-{6-[(isopropyl-phenyl-carbamoyl)-methyl]-5-oxo-1-phenyl-5,6-dihydro-4H-2,3,6,10b-tetraaza-benzo[e]azulen-4-ylmethyl}-indole-1-carboxylic acid tert-butyl ester (100 mg, 0.147 mmol) in DMF (2 mL) at −5° C. was added KHMDS (0.5M in THF, 322 μL, 0.161 mmol). The solution was stirred at −5° C. for 20 minutes and methyl iodide (10 μL, 0.161 mmol) was added. The reaction was stirred at room temperature for 24 hours, was diluted with EtOAc and the organic solution was washed with brine (3×). The organic solution was dried (Na$_2$SO$_4$), filtered and concentrated. The residue was purified by preparative chromatography (2×) eluting with 50% EtOAc in hexanes to provide 34 mg of 3-{6-[(isopropyl-phenyl-carbamoyl)-methyl]-4-methyl-5-oxo-1-phenyl-5,6-dihydro-4H-2,3,6,10b-tetraaza-benzo[e]azulen-4-ylmethyl}-indole-1-carboxylic acid tert-butyl ester. $^1$H NMR (CD$_2$Cl$_2$) δ 8.05 (d, 1H), 7.67 (d, 1H), 7.36-7.54 (m, 10H), 7.08-7.30 (m, 6H), 6.90 (d, 1H), 5.02 (m, 1H), 4.29 (d, 1H), 4.11 (m, 1H), 2.78 (s, 2H), 1.80 (s, 3H), 1.64 (s, 9H), 1.10 (m, 6H); MS 695.3 (M+1).

Step C: 2-[4-(1H-Indol-3-ylmethyl)-4-methyl-5-oxo-1-phenyl-4,5-dihydro-2,3,6,10b-tetraaza-benzo[e]azulen-6-yl]-N-isopropyl-N-phenyl-acetamide To a solution of 3-{6-[(isopropyl-phenyl-carbamoyl)-methyl]-4-methyl-5-oxo-1-phenyl-5,6-dihydro-4H-2,3,6,10b-tetraaza-benzo[e]azulen-4-ylmethyl}-indole-1-carboxylic acid tert-butyl ester in dioxane (1 mL) was added HCl (4.0M in dioxane, 550 μL) and the reaction was stirred at room temperature for 50 hours. The volatiles were concentrated in vacuo and the residue was dissolved in CH$_2$Cl$_2$. The organic solution was washed with aqueous NaHCO$_3$ (1×), dried (Na$_2$SO$_4$), filtered and concentrated. Purification by preparative chromatography eluting with 40% acetone in CH$_2$Cl$_2$ provided 17 mg of 2-[4-(1H-indol-3-ylmethyl)-4-methyl-5-oxo-1-phenyl-4,5-dihydro-2,3,6,10b-tetraaza-benzo[e]azulen-6-yl]-N-isopropyl-N-phenyl-acetamide. $^1$H NMR (CD$_2$Cl$_2$) δ 8.37 (s, 1H), 7.78 (m, 1H), 7.53-7.23 (m, 13H), 7.11 (m, 2H), 7.02 (t, 1H), 6.90 (d, 1H), 5.03 (m, 1H), 4.33 (d, 1H), 3.76-3.58 (m, 1H), 2.83 (m, 2H), 1.75 (s, 3H), 1.11 (m, 6H); MS 595.2 (M+1).

Example 5(A)
Preparation of 2-[1-(2-Fluoro-phenyl)-4-(1H-indazol-3-ylmethyl)-5-oxo-4,5-dihydro-2,3,6,10b-tetraaza-benzo[e]azulen-6-yl]-N-isopropyl-N-phenyl-acetamide

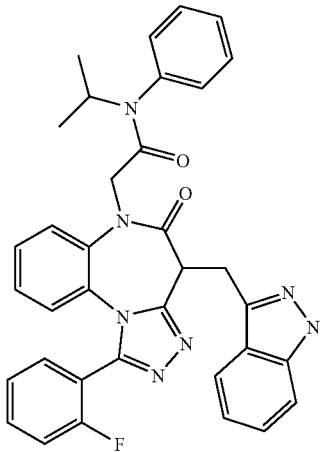

Following the procedure described for Preparation 4(C); 2-fluoro-benzoic acid hydrazide was reacted with 2-(4-ethoxy-2-oxo-2,3-dihydro-benzo[b][1,4]diazepin-1-yl)-N-isopropyl-N-phenyl-acetamide (Preparation 5(B)). This intermediate was carried forward according to Example 3(B) Steps A and B above to afford 2-[1-(2-fluoro-phenyl)-4-(1H-indazol-3-ylmethyl)-5-oxo-4,5-dihydro-2,3,6,10b-tetraaza-benzo[e]azulen-6-yl]-N-isopropyl-N-phenyl-acetamide. $^1$H NMR (CD$_2$Cl$_2$) δ 7.92 (d, 1H), 7.96 (dt, 1H), 7.59 (d, 1H), 7.33-7.50 (m, 7H), 7.15-7.25 (m, 4H), 7.02-7.10 (m, 2H), 6.82 (dd, 1H), 4.90-4.96 (m, 1H), 4.38 (t, 1H), 4.17 (d, 1H), 3.92-4.03 (m, 3H), 1.04 (m, 6H); MS 600 (M+1).

Example 5(B)
Preparation of 2-[1-(3-Fluoro-phenyl)-4-(1H-indazol-3-ylmethyl)-5-oxo-4,5-dihydro-2,3,6,10b-tetraaza-benzo[e]azulen-6-yl]-N-isopropyl-N-phenyl-acetamide

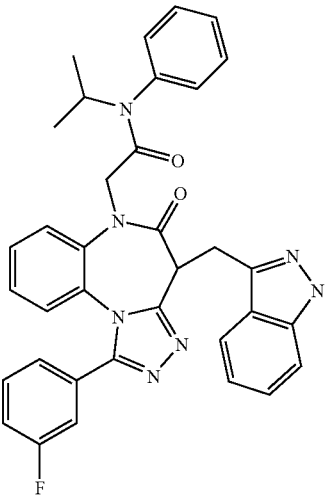

Following the procedure described for Preparation 4(C), Step A; 3-fluoro-benzoic acid hydrazide was reacted with 2-(4-ethoxy-2-oxo-2,3-dihydro-benzo[b][1,4]diazepin-1-yl)-N-isopropyl-N-phenyl-acetamide (Preparation 5(B)). This intermediate was carried forward according to Example 3(B) Steps A and B to afford 2-[1-(3-fluoro-phenyl)-4-(1H-indazol-3-ylmethyl)-5-oxo-4,5-dihydro-2,3,6,10b-tetraaza-benzo[e]azulen-6-yl]-N-isopropyl-N-phenyl-acetamide. $^1$H NMR (CD$_2$Cl$_2$) δ 7.95 (d, 1H), 7.35-7.50 (m, 10H), 7.15-7.21 (m, 5H), 6.91 (d, 1H), 4.76-4.83 (m, 1H), 4.52 (d, 1H), 4.34 (t, 1H), 3.92-4.08 (m, 3H), 0.98 (dd, 6H); MS 600 (M+1).

Example 5(C)
Preparation of 2-[1-Cyclohexyl-4-(1H-indazol-3-ylmethyl)-5-oxo-4,5-dihydro-2,3,6,10b-tetraaza-benzo[e]azulen-6-yl]-N-isopropyl-N-phenyl-acetamide

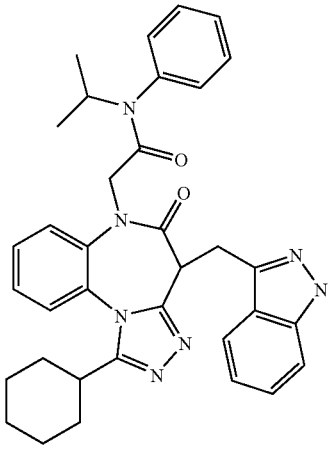

Following the procedure described for Preparation 4(C), Step A; cyclohexanecarboxylic acid hydrazide (Preparation 14) was reacted with 2-(4-ethoxy-2-oxo-2,3-dihydro-benzo[b][1,4]diazepin-1-yl)-N-isopropyl-N-phenyl-acetamide (Preparation 5(B)). This intermediate was carried forward according to Example 3(B) Steps A and B to afford 2-[1-cyclohexyl-4-(1H-indazol-3-ylmethyl)-5-oxo-4,5-dihydro-2,3,6,10b-tetraaza-benzo[e]azulen-6-yl]-N-isopropyl-N-phenyl-acetamide. $^1$H NMR (CD$_2$Cl$_2$) δ 7.92 (d, 1H), 7.51-7.61 (m, 3H), 7.37-7.50 (m, 6H), 7.16-7.20 (m, 3H), 4.85 (m, 1H), 4.24 (m, 1H), 4.00 (d, 1H), 3.93 (d, 1H), 2.77-2.85 (m, 1H), 2.17 (d, 1H), 1.91 (d, 2H), 1.07-1.66 (br.m, 3H), 1.01 (dd, 6H); MS 588 (M+1).

Example 5(D)
Preparation of 2-[1-(4-Fluoro-phenyl)-4-(1H-indazol-3-ylmethyl)-5-oxo-4,5-dihydro-2,3,6,10b-tetraaza-benzo[e]azulen-6-yl]-N-isopropyl-N-phenyl-acetamide

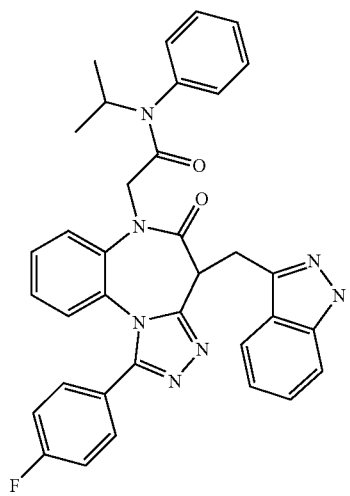

Following the procedure described for Example 4(C), Step A; 4-fluorobenzoic acid hydrazide was reacted with 2-(4-ethoxy-2-oxo-2,3-dihydro-benzo[b][1,4]diazepin-1-yl)-N-isopropyl-N-phenyl-acetamide (Preparation 5(B)). This intermediate was carried forward according to Example 3(B) Steps A and B to afford 2-[1-(4-fluoro-phenyl)-4-(1H-indazol-3-ylmethyl)-5-oxo-4,5-dihydro-2,3,6,10b-tetraaza-benzo[e]azulen-6-yl]-N-isopropyl-N-phenyl-acetamide. $^1$H NMR (CD$_2$Cl$_2$) δ 7.92 (d, 1H), 7.64-7.67 (m, 2H), 7.32-7.44 (m, 7H), 7.07-7.20 (m, 6H), 6.87 (d, 1H), 4.77-4.84 (m, 1H), 4.48 (d, 1H), 4.32-4.36 (m, 1H), 3.91-4.05 (m, 3H), 0.98 (dd, 6H); MS 600 (M+1).

Example 5(E)

Preparation of N-(4-Fluoro-phenyl)-2-[4-(1H-indazol-3-ylmethyl)-5-oxo-1-phenyl-4,5-dihydro-2,3,6,10b-tetraaza-benzo[e]azulen-6-yl]-N-isopropyl-acetamide Following the procedure described for Preparation 4(C), Alternative preparation Step A; 1-phenyl-4H,6H-2,3,6,10b-tetraaza-benzo[e]azulen-5-one (Preparation 4(A)) (1.0 g, 3.62 mmol) was alkylated with 2-bromo-N-(4-fluoro-phenyl)-N-isopropyl-acetamide (Preparation 1 (D)) (1.1 g, 3.98 mmol). This intermediate was carried forward according to Example 3(B) Steps A and B to afford N-(4-fluoro-phenyl)-2-[4-(1H-indazol-3-ylmethyl)-5-oxo-1-phenyl-4,5-dihydro-2,3,6,10b-tetraaza-benzo[e]azulen-6-yl]-N-isopropyl-acetamide. $^1$H NMR (CD$_2$Cl$_2$) δ 7.94 (d, 1H), 7.63 (d, 2H), 7.38-7.59 (br. m, 7H), 7.12-7.29 (br. m, 6H), 6.90 (d, 1H), 4.79-4.86 (m, 1H), 4.36-4.45 (br. m, 2H), 3.95-4.05 (br. m, 3H), 0.98 (dd, 6H); MS 600 (M+1).

Example 6(A)

Preparation of 2-[4-(1H-Indol-3-ylmethyl)-5-oxo-1-phenyl-4,5-dihydro-2,3,6,10b-tetraaza-benzo[e]azulen-6-yl]-N-isopropyl-N-phenyl-acetamide

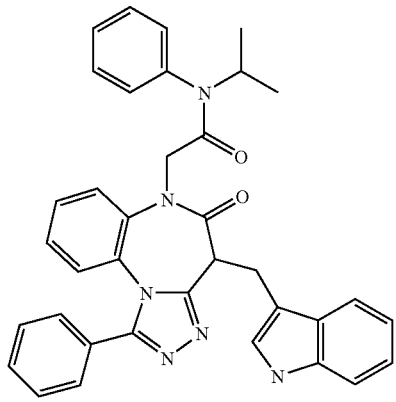

Step A: 2-[4-(1H-Indol-3-ylmethylene)-5-oxo-1-phenyl-4,5-dihydro-2,3,6,10b-tetraaza-benzo[e]azulen-6-yl]-N-isopropyl-N-phenyl-acetamide To a solution of N-isopropyl-2-(5-oxo-1-phenyl-4,5-dihydro-2,3,6,10b-tetraaza-benzo[e]azulen-6-yl)-N-phenyl-acetamide (Preparation 7(A)) (1.2 g, 2.7 mmol) in toluene (15 mL) was added 1H-indole-3-carbaldehyde (0.46 g, 3.2 mmol) and piperidine (0.4 mL). The reaction mixture was heated to reflux for 14 hours. Activated 4 Å molecular sieves (2 g) were added and the reaction mixture was refluxed for 24 hours. The sieves were removed by filtration and the filtrate was concentrated. The residue was triturated with methylene chloride and the solid was collected via filtration and was dried in vacuo to give 1.5 g of 2-[4-(1H-indol-3-ylmethylene)-5-oxo-1-phenyl-4,5-dihydro-2,3,6,10b-tetraaza-benzo[e]azulen-6-yl]-N-isopropyl-N-phenyl-acetamide. The filtrate was concentrated and was purified by chromatography (20% acetone/methylene chloride) to afford an additional 320 mg of 2-[4-(1H-indol-3-ylmethylene)-5-oxo-1-phenyl-4,5-dihydro-2,3,6,10b-tetraaza-benzo[e]azulen-6-yl]-N-isopropyl-N-phenyl-acetamide. MS 579.2 (M+1).

Step B: 2-[4-(1H-Indol-3-ylmethyl)-5-oxo-1-phenyl-4,5-dihydro-2,3,6,10b-tetraaza-benzo[e]azulen-6-yl]-N-isopropyl-N-phenyl-acetamide To 10% Pd/C and EtOH was added 2-[4-(1H-indol-3-ylmethylene)-5-oxo-1-phenyl-4,5-dihydro-2,3,6,10b-tetraaza-benzo[e]azulen-6-yl]-N-isopropyl-N-phenyl-acetamide (0.71 g, 1.2 mmol). An additional 25 mL of EtOH was added followed by ammonium formate (0.77 g, 12.2 mmol). The reaction mixture was heated to 80° C. for 6 hours. The catalyst was removed by filtration through Celite® and the filtrate was concentrated. The residue was dissolved in ethyl acetate and the organic solution was washed with saturated NaHCO$_3$. The organic phase was dried over sodium sulfate and concentrated. The crude product was purified by chromatography (0% to 18% acetone/methylene chloride) to give 128 mg of 2-[4-(1H-indol-3-ylmethyl)-5-oxo-1-phenyl-4,5-dihydro-2,3,6,10b-tetraaza-benzo[e]azulen-6-yl]-N-isopropyl-N-phenyl-acetamide as a racemic mixture. $^1$H NMR (CD$_2$Cl$_2$) δ 8.18 (s, 1H), 7.64 (dd, 2H), 7.55 (dd, 1H), 7.510-7.41 (m, 8H), 7.36 (dd, 1H), 7.25 (m, 3H), 7.09 (m, 2H), 7.027 (m, 1H), 6.85 (dd, 1H), 4.86 (m, 1H), 4.40 (br d, 1H), 4.04 (dd, 1H), 3.79 (m, 3H), 103 (dd, 6H); MS 581.4 (M+1).

Example 6(B)

Preparation of (−) 2-[4-(1H-Indol-3-ylmethyl)-5-oxo-1-phenyl-4,5-dihydro-2,3,6,10b-tetraaza-benzo[e]azulen-6-yl]-N-isopropyl-N-phenyl-acetamide, enantiomer 1

Racemic 2-[4-(1H-indol-3-ylmethyl)-5-oxo-1-phenyl-4,5-dihydro-2,3,6,10b-tetraaza-benzo[e]azulen-6-yl]-N-isopropyl-N-phenyl-acetamide (Example 6(A)) was separated into its enantiomers using a Chiralpak AD column (10 cm×50 cm), eluting with heptane/ethanol (80:20), using a flow rate of 250 mL/minute to provide (−) 2-[4-(1H-indol-3-ylmethyl)-5-oxo-1-phenyl-4,5-dihydro-2,3,6,10b-tetraaza-benzo[e]azulen-6-yl]-N-isopropyl-N-phenyl-acetamide (enantiomer 1) having a retention time of 8.64 minutes. MS 581 (M+1); $[\alpha]_D^{20}$ −91.4 (c 1.04, ethanol).

Example 6(C)

Preparation of 2-[1-Cyclohexyl-4-(1H-indol-3-ylmethyl)-5-oxo-4,5-dihydro-2,3,6,10b-tetraaza-benzo[e]azulen-6-yl]-N-isopropyl-N-phenyl-acetamide

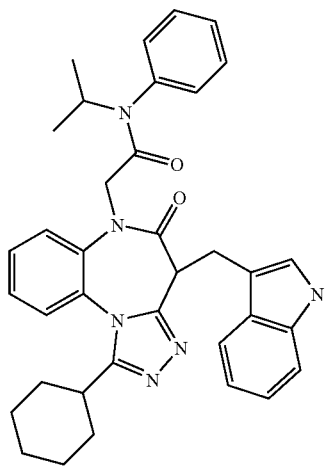

Following the procedure described for Example 6(A), Step A; 2-(1-cyclohexyl-5-oxo-4,5-dihydro-2,3,6,10b-tetraaza-benzo[e]azulen-6-yl)-N-isopropyl-N-phenyl-acetamide (Preparation 8(B)) was condensed with 1H-indole-3-carbaldehyde. This intermediate was carried forward according to Example 6(A) Step B to afford 2-[1-cyclohexyl-4-(1H-indol-3-ylmethyl)-5-oxo-4,5-dihydro-2,3,6,10b-tetraaza-benzo[e]azulen-6-yl]-N-isopropyl-N-phenyl-acetamide. $^1$H NMR (CD$_2$Cl$_2$) δ 8.44 (s, 1H), 7.42-7.48 (m, 4H), 7.28-7.42 (m, 4H), 7.17-7.19 (m, 2H), 7.07-7.10 (m, 1H), 6.98-7.02 (m, 1H), 4.90-4.94 (m, 1H), 4.07-4.15 (m, 1H), 3.91 (d, 1H), 3.67-3.73 (m, 2H), 2.83 (br.m, 1H), 2.19 (br.m, 1H), 1.89-1.92 (m, 2H), 1.68 (br.s, 4H), 1.50-1.59 (m, 1H), 1.32-1.35 (m, 2H), 1.23 (t, 1H), 1.06 (m, 6H); MS 587 (M+1).

Example 6(D)

Preparation of 2-[1-(2-Fluoro-phenyl)-4-(1H-indol-3-ylmethyl)-5-oxo-4,5-dihydro-2,3,6,10b-tetraaza-benzo[e]azulen-6-yl]-N-isopropyl-N-phenyl-acetamide

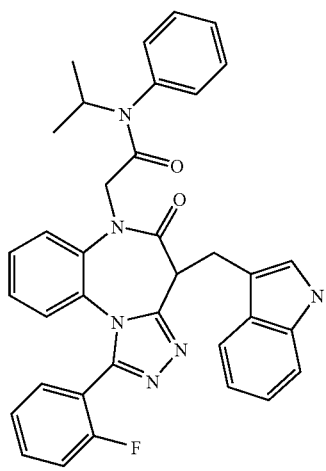

Following the procedure described for Example 6(A), Step A; 2-(1-(2-fluorophenyl)-5-oxo-4,5-dihydro-2,3,6,10b-tetraaza-benzo[e]azulen-6-yl)-N-isopropyl-N-phenyl-acetamide (Preparation 7(B)) was condensed with 1H-indole-3-carbaldehyde. This intermediate was carried forward according to Example 6(A) Step B to afford 2-[1-(2-fluorophenyl)-4-(1H-indol-3-ylmethyl)-5-oxo-4,5-dihydro-2,3,6,10b-tetraaza-benzo[e]azulen-6-yl]-N-isopropyl-N-phenyl-acetamide. $^1$H NMR (CD$_2$Cl$_2$) δ 8.26 (s, 1H), 7.71-7.74 (m, 1H), 7.60-7.67 (m, 2H), 7.40-7.59 (m, 6H), 7.34-7.38 (m, 2H), 7.23-7.32 (br. m, 2H), 7.14-7.20 (m, 1H), 7.05-7.12 (m, 3H), 6.81-6.83 (m, 1H), 4.98-5.03 (m, 1H), 4.28 (d, 1H), 3.93 (d, 1H), 3.83-3.84 (m, 3H), 1.12 (d, 6H); MS 599 (M+1).

Example 7

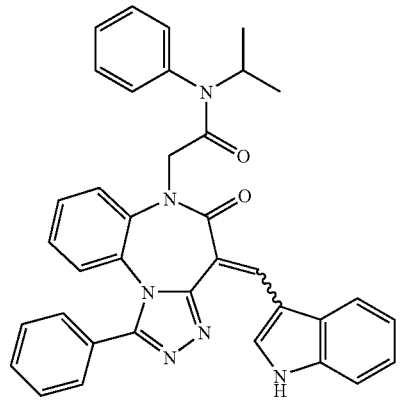

Preparation of 2-[4-(1H-Indol-3-ylmethylene)-5-oxo-1-phenyl-4,5-dihydro-2,3,6,10b-tetraaza-benzo[e]azulen-6-yl]-N-isopropyl-N-phenyl-acetamide To a solution of N-isopropyl-2-(5-oxo-1-phenyl-4,5-dihydro-2,3,6,10b-tetraaza-benzo[e]azulen-6-yl)-N-phenyl-acetamide (Preparation 7(A)) (1.2 g, 2.7 mmol) and piperidine (0.4 mL, 1.33 mmol) in toluene was added 1H-indole-3-carbaldehyde (0.46 g, 3.2 mmol). The reaction mixture was heated at 110° C. for 31 hours. Activated 4 Å molecular sieves (2 g) were added. The reaction mixture was heated for 24 hours at 110° C. The reaction was cooled to room temperature and the molecular sieves were filtered with the aid of toluene. The filtrate was concentrated and the residue was purified by chromatography (12%-20% acetone/methylene chloride) to give 1.5 g of 2-[4-(1H-indol-3-ylmethylene)-5-oxo-1-phenyl-4,5-dihydro-2,3,6,10b-tetraaza-benzo[e]azulen-6-yl]-N-isopropyl-N-phenyl-acetamide as a solid. MS 579.2 (M+1).

Example 8

Each of the compounds in the table below may be prepared by procedures similar to those described in the Examples above.

| Structure | Name |
|---|---|
| A 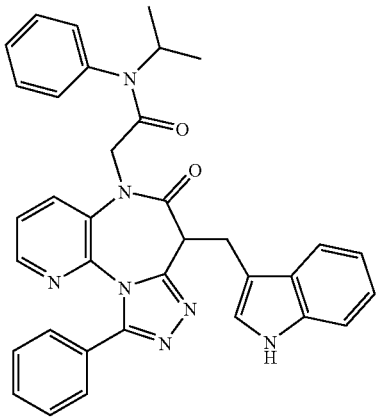 | 2-[4-(1H-Indol-3-ylmethyl)-5-oxo-1-phenyl-4,5-dihydro-2,3,6,10,10b-pentaaza-benzo[e]azulen-6-yl]-N-isopropyl-N-phenyl-acetamide |
| B 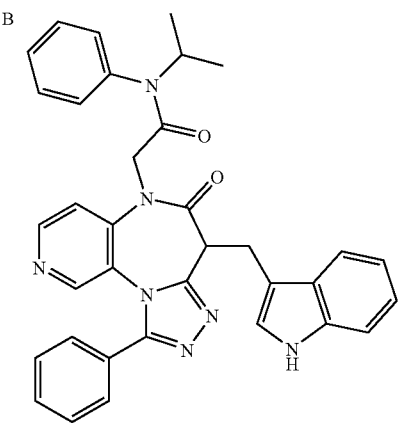 | 2-[4-(1H-Indol-3-ylmethyl)-5-oxo-1-phenyl-4,5-dihydro-2,3,6,9,10b-pentaaza-benzo[e]azulen-6-yl]-N-isopropyl-N-phenyl-acetamide |
| C 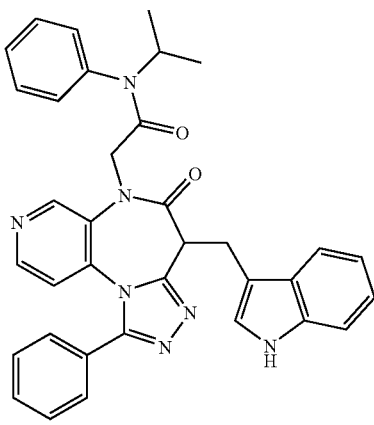 | 2-[4-(1H-Indol-3-ylmethyl)-5-oxo-1-phenyl-4,5-dihydro-2,3,6,8,10b-pentaaza-benzo[e]azulen-6-yl]-N-isopropyl-N-phenyl-acetamide |

-continued

| Structure | Name |
|---|---|
| D | 2-[4-(1H-Indol-3-ylmethyl)-5-oxo-1-phenyl-4,5-dihydro-2,3,6,7,10b-pentaaza-benzo[e]azulen-6-yl]-N-isopropyl-N-phenyl-acetamide |
| E | 2-[4-(1H-Indol-3-ylmethyl)-5-oxo-1-phenyl-4,5-dihydro-2,3,6,7,8,10b-hexaaza-benzo[e]azulen-6-yl]-N-isopropyl-N-phenyl-acetamide |
| F | 2-[4-(1H-Indol-3-ylmethyl)-5-oxo-1-phenyl-4,5-dihydro-2,3,6,7,9,10b-hexaaza-benzo[e]azulen-6-yl]-N-isopropyl-N-phenyl-acetamide |

| Structure | Name |
|---|---|
| G 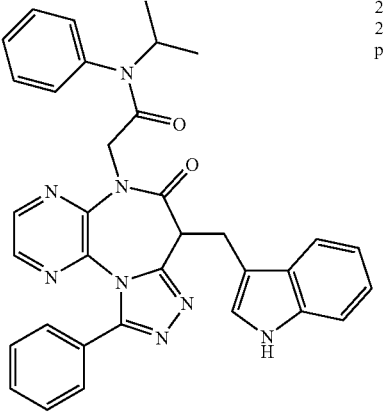 | 2-[4-(1H-Indol-3-ylmethyl)-5-oxo-1-phenyl-4,5-dihydro-2,3,6,7,10,10b-hexaaza-benzo[e]azulen-6-yl]-N-isopropyl-N-phenyl-acetamide |
| H 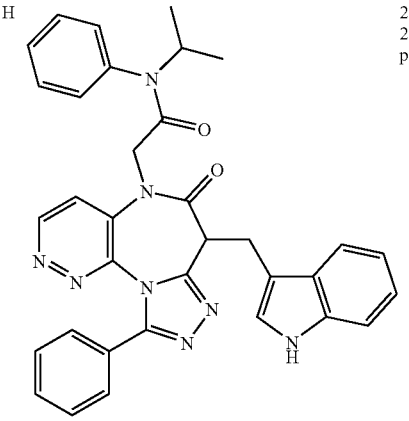 | 2-[4-(1H-Indol-3-ylmethyl)-5-oxo-1-phenyl-4,5-dihydro-2,3,6,9,10,10b-hexaaza-benzo[e]azulen-6-yl]-N-isopropyl-N-phenyl-acetamide |
| I 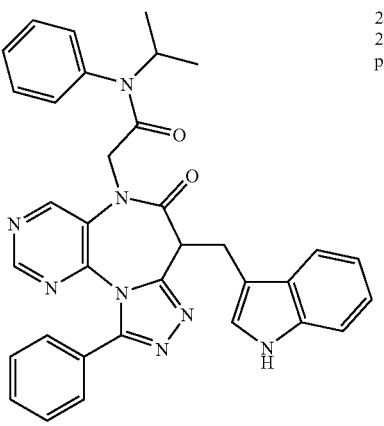 | 2-[4-(1H-Indol-3-ylmethyl)-5-oxo-1-phenyl-4,5-dihydro-2,3,6,8,10,10b-hexaaza-benzo[e]azulen-6-yl]-N-isopropyl-N-phenyl-acetamide |

-continued
| Structure | Name |
|---|---|
| J 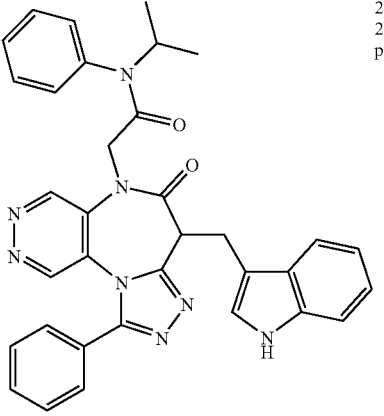 | 2-[4-(1H-Indol-3-ylmethyl)-5-oxo-1-phenyl-4,5-dihydro-2,3,6,8,9,10b-hexaaza-benzo[e]azulen-6-yl]-N-isopropyl-N-phenyl-acetamide |
| K 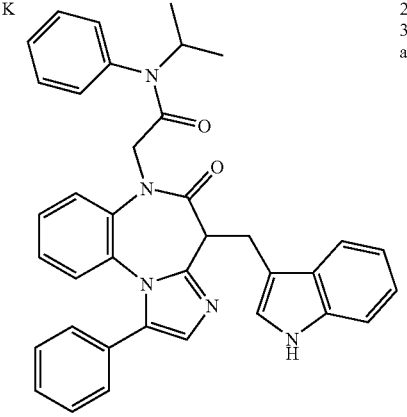 | 2-[4-(1H-Indol-3-ylmethyl)-5-oxo-1-phenyl-4,5-dihydro-3,6,10b-triaza-benzo[e]azulen-6-yl]-N-isopropyl-N-phenyl-acetamide |
| L 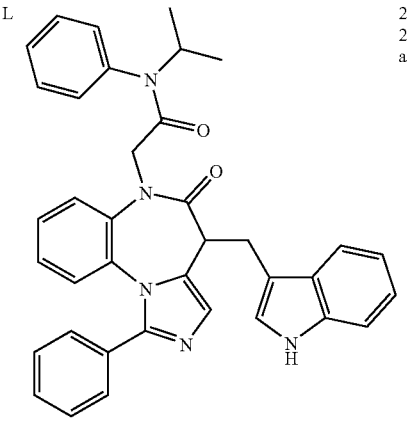 | 2-[4-(1H-Indol-3-ylmethyl)-5-oxo-1-phenyl-4,5-dihydro-2,6,10b-triaza-benzo[e]azulen-6-yl]-N-isopropyl-N-phenyl-acetamide |

Preparation 1(A)

Preparation of 2-Bromo-N-isopropyl-N-phenyl-acetamide

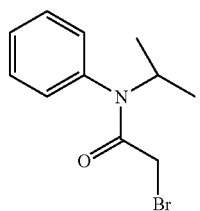

To a solution of N-isopropylaniline (21.58 g, 180 mmol) in CH$_2$Cl$_2$ (350 mL) was added triethylamine (26.7 mL, 190 mmol). The solution was cooled to 0° C. and bromoacetyl bromide (14.0 mL, 160 mmol) was added slowly over 1 hour. The reaction was warmed to room temperature and was stirred for 24 hours. The reaction was diluted with 5% aqueous HCl. The organic solution was washed with 5% aqueous HCl (2×), aqueous NaHCO$_3$ (1×), and brine (1×). The organic solution was filtered through a silica gel pad, eluting with CH$_2$Cl$_2$. Recrystallization from hexanes (60 mL) provided 22.47 g of 2-bromo-N-isopropyl-N-phenyl-acetamide. $^1$H NMR (CD$_2$Cl$_2$) δ 7.45 (m, 3H), 7.21 (m, 2H), 4.89 (m, 1H), 3.52 (s, 2H), 1.05 (d, 6H); MS 256.2 (M+1).

Preparation 1(B)

Preparation of 2-Bromo-N-isopropyl-N-(6-methoxy-pyridin-3-yl)-acetamide

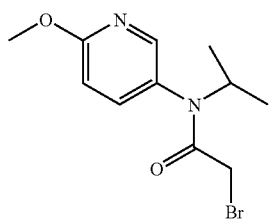

Method 1

Step A: Isopropylidene-(6-methoxy-pyridin-3-yl)-amine

To a solution of 5-amino-2-methoxypyridine (18 g, 161 mmol) in methanol (80 mL) was added acetone (20 mL, 177 mmol). The reaction was heated at reflux for 24 hours and the volatiles were concentrated in vacuo to provide 21.3 g of isopropylidene-(6-methoxy-pyridin-3-yl)-amine. $^1$H NMR (CDCl$_3$) δ 7.59 (d, 1H), 7.31 (m, 1H), 6.70 (d, 1H), 3.91 (s, 3H), 2.20 (s, 3H), 1.85 (s, 3H).

Step B: Isopropyl-(6-methoxy-pyridin-3-yl)-amine

To a solution of isopropylidene-(4-methoxy-phenyl)-amine (21.3 g, 129 mmol) in a mixture of EtOH (100 mL) and MeOH (50 mL) at 0° C. was added NaBH$_4$ (14.7 g, 389 mmol) in 3 portions. The reaction was stirred at room temperature for 3 hours and was diluted with water. The aqueous layer was washed with EtOAc (3×) and the combined organic extracts were dried (MgSO$_4$), filtered and concentrated. The residue was purified by medium pressure chromatography eluting with a solvent gradient (2% MeOH in CH$_2$Cl$_2$ to 12% MeOH in CH$_2$Cl$_2$) to provide 11.26 g of isopropyl-(6-methoxy-pyridin-3-yl)-amine. $^1$H NMR (CDCl$_3$) δ 7.55 (d, 1H), 6.96 (dd, 1H), 6.61 (d, 1H), 3.86 (s, 3H), 3.52 (m, 1H), 1.19 (d, 6H).

Method 2

Step A: Isopropyl-(6-methoxy-pyridin-3-yl)-amine

To a solution of 5-amino-2-methoxypyridine (747 mg, 6.02 mmol) in CH$_2$Cl$_2$ (50 mL) was added acetone (500 µL) and sodium triacetoxyborohydride (1.95 g, 9.20 mmol). The reaction was stirred at room temperature for 20 hours and was diluted with aqueous NaHCO$_3$. The aqueous solution was washed with CH$_2$Cl$_2$ (3×) and the combined organic solutions were washed with brine (1×), dried (MgSO$_4$), filtered and concentrated. The residue was purified by medium pressure chromatography eluting with a solvent gradient (5% EtOAc in hexanes to 50% EtOAc in hexanes) to provide 810 mg of isopropyl-(6-methoxy-pyridin-3-yl)-amine. $^1$H NMR (CDCl$_3$) δ 7.55 (s, 1H), 6.96 (dd, 1H), 6.61 (d, 1H), 3.86 (s, 3H), 3.52 (m, 1H), 1.19 (d, 6H).

Step B: 2-Bromo-N-isopropyl-N-(6-methoxy-pyridin-3-yl)-acetamide

To a solution of isopropyl-(6-methoxy-pyridin-3-yl)-amine (6.73 g, 41.0 mmol) in CH$_2$Cl$_2$ (130 mL) at 0° C. was added diisopropylethylamine (7.15 mL, 41.0 mmol) followed by bromoacetyl bromide (8.28 g, 41.0 mmol) in CH$_2$Cl$_2$ (60 mL) over 0.5 hours. The reaction was stirred at room temperature for 24 hours and was diluted with water. The organic solution was washed with brine (1×), dried (MgSO$_4$), filtered and concentrated. The residue was purified by medium pressure chromatography eluting with a solvent gradient (1% MeOH in CH$_2$Cl$_2$ to 5% MeOH in CH$_2$Cl$_2$) to provide 2.27 g of 2-bromo-N-isopropyl-N-(6-methoxy-pyridin-3-yl)-acetamide. $^1$H NMR (CD$_3$OD) δ 8.08 (d, 1H), 7.62 (dd, 1H), 6.89 (d, 1H), 4.84 (m, 1H), 3.9 (s, 3H), 3.60 (s, 2H), 1.06 (m, 6H).

Preparation 1(C)

Preparation of N-Benzyl-2-bromo-N-isopropyl-acetamide

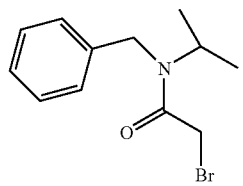

To a solution of N-isopropylbenzylamine (40 mL, 240 mmol) in CHCl$_3$ (300 mL) was added Et$_3$N (36.8 mL). The reaction was cooled to 0° C. and bromoacetyl bromide (21.8 mL, 251 mmol) was added. The mixture was stirred at room temperature for 24 hours and was diluted with CH$_2$Cl$_2$. The organic solution was washed consecutively with 5% aqueous HCl (1×) and aqueous NaHCO₃ (1×). The organic solution was dried (Na₂SO₄), filtered and concentrated. The residue was dissolved in 40% EtOAc in hexanes and was filtered through a silica gel pad to provide 52.2 g of N-benzyl-2-bromo-N-isopropyl-acetamide. ¹H NMR (CD₂Cl₂) δ 7.20-7.40 (m, 5H), 4.53 (d, 2H), 4.22 (m) and 4.74 (m, total 1H), 4.01 (s, 1H), 3.72 (s, 1H), 1.20 (d, 3H), 1.12 (d, 3H).

Preparation 1(D)

Preparation of
2-Bromo-N-(4-fluoro-phenyl)-N-isopropyl-acetamide

Following the procedure described for Preparation 1(A); (4-fluoro-phenyl)-isopropyl-amine (13.70 g, 89.54 mmol) was alkylated with bromoacetyl bromide (7.78 mL, 89.54 mmol) to provide 15.02 g of 2-bromo-N-(4-fluoro-phenyl)-N-isopropyl-acetamide as an oil. ¹H NMR (CD₂Cl₂) δ 7.14-7.23 (m, 4H), 4.90 (m, 1H), 3.53 (s, 2H), 1.05 (d, 6H).

Preparation 2(A)

Preparation of
(6-Chloro-pyridin-3-yl)-isopropyl-amine

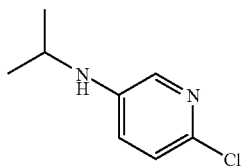

To a solution of 2-chloro-5-aminopyridine (500 mg, 3.88 mmol) and acetone (250 µL, 4.27 mmol) in dichloroethane (13 mL) was added NaBH(OAc)₃ (989 mg, 4.66 mmol) and AcOH (330 µL, 5.82 mmol). The reaction was stirred for 24 hours and was diluted with 1N NaOH. The aqueous solution was washed with CH₂Cl₂ (3×). The combined organic solutions were dried (Na₂SO₄), filtered and concentrated. Purification by medium pressure chromatography eluting with a solvent gradient (2% MeOH in CH₂Cl₂ to 5% MeOH in CH₂Cl₂) provided 505.2 mg of (6-chloro-pyridin-3-yl)-isopropyl-amine. ¹H NMR (CD₃OD) δ 7.64 (d, 1H), 7.10 (d, 1H), 6.99 (dd, 1H), 3.55 (m, 1H), 1.17 (d, 6H).

Preparation 2(B)

Preparation of
(6-Ethoxy-pyridin-3-yl)-isopropyl-amine

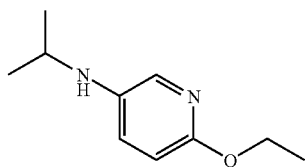

Following the procedure described for Preparation 2(A), 6-ethoxy-pyridin-3-ylamine (10 g, 72.4 mmol) was reacted with acetone (4.8 mL) to provide 11.18 g of (6-ethoxy-pyridin-3-yl)-isopropyl-amine. ¹H NMR (CD₃OD) δ 7.48 (d, 1H), 7.11 (dd, 1H), 6.61 (d, 1H), 4.14 (q, 2H), 3.48 (m, 1H), 1.32 (t, 3H), 1.14 (d, 6H); MS 181.3 (M+1).

Preparation 3(A)

Preparation of
4-Ethoxy-1,3-dihydro-benzo[b][1,4]diazepin-2-one

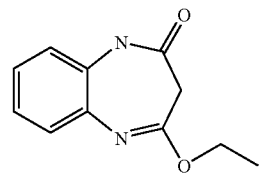

To a solution phenylenediamine (17.2 g, 159.2 mmol) and acetic acid (0.4 mL) in xylenes (225 mL) at 140° C. was added 3,3-diethoxyacrylic acid ethyl ester (30.0 g, 159.2 mmol) in xylenes (80 mL) dropwise over 50 minutes. The reaction was heated at 140° C. for 2 hours, was cooled to room temperature, and was stirred for 24 h. The resulting white precipitate was filtered, was washed with ether (100 mL), and was dried under vacuum to provide 18.37 g of 4-ethoxy-1,3-dihydro-benzo[b][1,4]diazepin-2-one as a white fluffy solid. MS 205 (M+1).

Preparation 3(B)

Preparation of 4-Ethoxy-7,8-difluoro-1,3-dihydro-benzo[b][1,4]diazepin-2-one

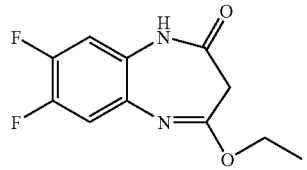

To a solution of 1,2-diamino-4,5-difluorobenzene (4.0 g, 27.75 mmol) in xylenes (50 mL) at 140° C. was added acetic acid (200 µL) followed by a solution of 3,3-diethoxyacrylic acid ethyl ester (5.22 g, 27.75 mmol) in xylenes (25 mL) over 1 hour. The reaction was heated at 140° C. for 2 hours, was cooled to room temperature, and was concentrated. The residue was triturated in hexanes to provide 5.38 g of 4-ethoxy-7,8-difluoro-1,3-dihydro-benzo[b][1,4]diazepin-2-one. ¹H NMR (CDCl₃) δ 7.05 (q, 1H), 6.87 (q, 1H), 4.29 (q, 2H), 3.18 (s, 2H), 1.35 (t, 3H).

Preparation 4(A)

Preparation of 1-Phenyl-4H,6H-2,3,6,10b-tetraaza-benzo[e]azulen-5-one

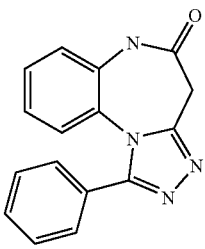

To a solution of 4-ethoxy-1,3-dihydro-benzo[b][1,4]diazepin-2-one (Preparation 3(A) (5 g, 24 mmol) in glacial AcOH (75 mL) was added benzoic acid hydrazide (3.33 g, 24.5 mmol). The reaction mixture was heated to 120° C. for 2 hours and was cooled to room temperature. The solvent was removed in vacuo by azeotropic distillation with heptane (2×). The residue was dissolved in a minimum amount of methylene chloride and 50 mL ethyl acetate and the solution was poured slowly with stirring into a solution of 100 mL saturated NaHCO₃/100 mL water. Ether (150 mL) was added and the mixture was stirred for 5 minutes. The precipitate was collected by filtration, was washed with water and the minimum amount of ether to give 5.89 g of 1-phenyl-4H,6H-2,3,6,10b-tetraaza-benzo[e]azulen-5-one.
$^1$H NMR (CDCl₃) δ 9.02 (br s, 1H), 7.48-7.36 (m, 6H), 7.10 (t, 1H), 6.95 (d, 1H), 4.23 (d, 1H), 3.60 (d, 1H); MS 277 (M+1).

To a solution of 4-ethoxy-7,8-difluoro-1,3-dihydro-benzo[b][1,4]diazepin-2-one (Preparation 3(B) (5.38 g, 22.4 mmol) in acetic acid (100 mL) was added benzoic hydrazide (3.11 g, 22.85 mmol). The reaction was heated to 120° C. for 18 hours and the volatiles were concentrated in vacuo. The residue was dissolved in CH₂Cl₂ and the organic solution was washed with aqueous NaHCO₃ (1×), dried (Na₂SO₄), filtered and concentrated. The solid residue was triturated with a warm mixture of EtOAc and hexanes and was filtered. The solids were triturated in 50% hexanes in Et₂O and filtered to provide 3.97 g of 8,9-difluoro-1-phenyl-4H,6H-2,3,6,10b-tetraaza-benzo[e]azulen-5-one. $^1$H NMR (DMSO-d₆) δ 7.52-7.36 (m, 6H), 7.06 (m, 1H), 3.91 (d, 1H), 3.76 (d, 1H); MS 313.1 (M+1), 311.1 (M−1).

Preparation 4(B)

Preparation of 1-Cyclohexyl-4H,6H-2,3,6,10b-tetraaza-benzo[e]azulen-5-one

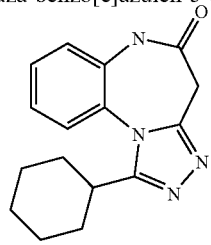

To a solution of 4-ethoxy-1,3-dihydro-benzo[b][1,4]diazepin-2-one (Preparation 3(A) (5 g, 24.5 mmol) in glacial acetic acid (75 mL) was added cyclohexanecarboxylic acid hydrazide (Preparation 14) (3.5 g, 24.5 mmol). The reaction was heated at 120° C. for 2.5 hours, was cooled to room temperature, and EtOAc (50 mL), water (50 mL) and aqueous NaHCO₃ (50 mL) were added. The mixture was stirred for 5 minutes and Et₂O was added (125 mL). The suspension was stirred for 15 minutes and the solids were removed by filtration with the aid of Et₂O to provide 5.92 g of 1-cyclohexyl-4H,6H-2,3,6,10b-tetraaza-benzo[e]azulen-5-one.
$^1$H NMR (CDCl₃) δ 8.36 (s, NH), 7.50 (m, 1H), 7.41 (m, 2H), 7.30 (d, 1H), 4.13 (d, 1H), 3.47 (d, 1H), 2.87 (m, 1H), 2.24 (d, 1H), 2.00 (m, 2H), 1.72-1.51 (m, 4H), 1.33 (m, 2H), 1.16 (m, 1H); MS 283.4 (M+1), 281.3 (M−1).

Preparation 4(C)

Preparation of 8,9-Difluoro-1-phenyl-4H,6H-2,3,6,10b-tetraaza-benzo[e]azulen-5-one

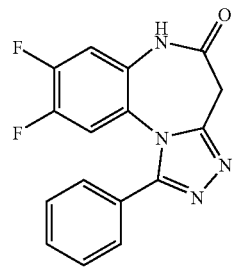

Preparation 5(A)

Preparation of 2-(4-Ethoxy-2-oxo-2,3-dihydro-benzo[b][1.4]diazepin-1-yl)-N-isopropyl-N-(6-methoxy-pyridin-3-yl)-acetamide

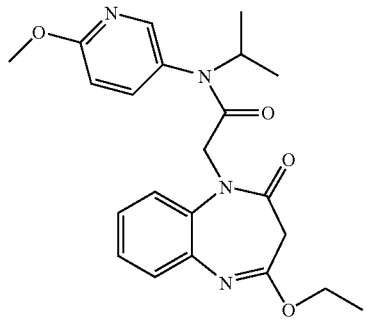

To a solution of 4-ethoxy-1,3-dihydro-benzo[b][1,4]diazepin-2-one (Preparation 3(A) (2 g, 9.79 mmol) in DMF (40 mL) at 0° C. was added NaH (60% in oil, 431 mg, 10.8 mmol). The reaction was stirred at 0° C. for 0.5 hour and a solution of 2-bromo-N-isopropyl-N-(6-methoxy-pyridin-3-yl)-acetamide (Preparation 1 (B) (2.95 g, 10.28 mmol) in DMF (5 mL) was added. The reaction was stirred at room temperature for 2 hours and was diluted with water, brine, and CH₂Cl₂. The aqueous solution was washed with CH₂Cl₂ (3×) and the combined organics were washed with brine, dried (MgSO₄), filtered and concentrated in vacuo. Purification by medium pressure chromatography eluting with a solvent gradient (hexanes to 70% EtOAc in hexanes) provided 2.87 g of 2-(4-ethoxy-2-oxo-2,3-dihydro-benzo[b][1,4]diazepin-1-yl)-N-isopropyl-N-(6-methoxy-pyridin-3-yl)-acetamide. $^1$H NMR (CDCl₃) δ 8.14 (s) and 7.93 (s, total 1H), 7.54 (m, 1H), 7.31 (m, 1H), 7.24-7.08 (m, 3H), 6.80 (m, 1H), 5.05 (m, 1H), 4.29 (m, 2H), 4.09 (m, 1H), 3.95 (m, 3H), 3.67 (d, 1H), 3.31 (d, 1H), 3.08 (d, 1H), 1.32 (m, 3H), 1.09 (m, 6H).

Preparation 5(B)

Preparation of 2-(4-Ethoxy-2-oxo-2,3-dihydro-benzo[b][1,4]diazepin-1-yl)-N-isopropyl-N-phenyl-acetamide

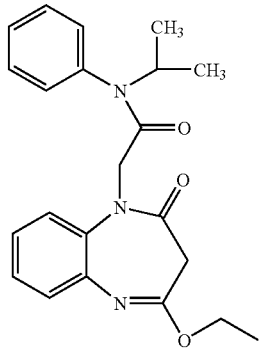

To a solution of 4-ethoxy-1,3-dihydro-benzo[b][1,4]diazepin-2-one (Preparation 3(A) (5.0 g, 24.5 mmol) in DMF (100 mL) was added potassium bistrimethyl silyl amide (49 mL of 0.5 M solution in toluene, 24.5 mmol) at 0° C. The reaction mixture was stirred for 20 minutes and was cooled to −17° C. A solution of 2-bromo-N-isopropyl-N-phenyl-acetamide (Preparation 1 (A) (6.9 g, 27 mmol) in DMF (50 mL) was added dropwise so the internal temperature remained below −15° C. The reaction mixture was stirred at −16° C. for 1 hour, was warmed to room temperature and was diluted with ethyl acetate. The organic phase was washed with brine, dried over sodium sulfate and was concentrated. The resulting pale brown solid was triturated with ether to obtain 3.2 g of 2-(4-ethoxy-2-oxo-2,3-dihydro-benzo[b][1,4]diazepin-1-yl)-N-isopropyl-N-phenyl-acetamide as a white powder. The filtrate was concentrated and the residue was triturated with ether/hexanes. The solid was collected by filtration to give a second crop of 2-(4-ethoxy-2-oxo-2,3-dihydro-benzo[b][1,4]diazepin-1-yl)-N-isopropyl-N-phenyl-acetamide (3.4 g). MS 380.2 (M+1).

Preparation 6

Preparation of 2-[1-(3-Benzyloxy-phenyl)-5-oxo-4,5-dihydro-2,3,6,10b-tetraaza-benzo[e]azulen-6-yl]-N-isopropyl-N-(6-methoxy-pyridin-3-yl)-acetamide

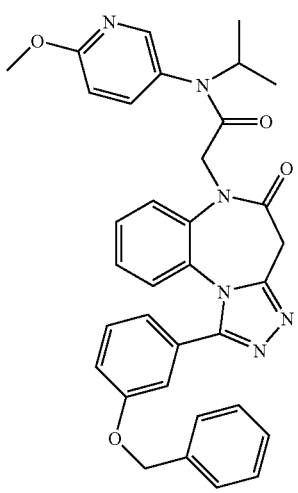

Following the procedure described for Preparation 4(B), 2-(4-ethoxy-2-oxo-2,3-dihydro-benzo[b][1,4]diazepin-1-yl)-N-isopropyl-N-(6-methoxy-pyridin-3-yl)-acetamide (Preparation 5(A) (150 mg, 0.365 mmol) was reacted with 3-benzyloxybenzydrazide (88 mg, 0.365 mmol) to provide 129 mg of 2-[1-(3-benzyloxy-phenyl)-5-oxo-4,5-dihydro-2,3,6,10b-tetraaza-benzo[e]azulen-6-yl]-N-isopropyl-N-(6-methoxy-pyridin-3-yl)-acetamide. $^1$H NMR (CD$_3$OD) δ 8.06 (d, 1H), 7.59 (m, 2H), 7.51 (t, 1H), 7.40-7.28 (m, 8H), 7.19 (t, 1H), 7.13 (d, 1H), 6.97 (d, 1H), 6.91 (d, 1H), 5.01 (d, 1H), 4.91 (d, 1H), 4.76 (m, 1H), 4.60 (m, 1H), 4.12 (m, 1H), 3.95 (s, 4H), 3.75 (d, 1H), 0.91 (m, 6H); MS 589.8 (M+1), 587.5 (M−1).

Preparation 7(A)

Preparation of N-Isopropyl-2-(5-oxo-1-phenyl-4,5-dihydro-2,3,6,10b-tetraaza-benzo[e]azulen-6-yl)-N-phenyl-acetamide

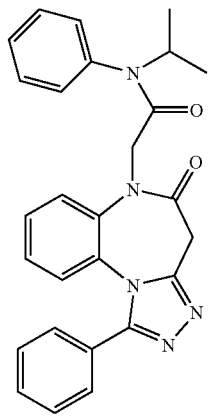

To a solution of 2-(4-ethoxy-2-oxo-2,3-dihydro-benzo[b][1,4]diazepin-1-yl)-N-isopropyl-N-phenyl-acetamide (Preparation 5(B) (71.14 g, 0.187 mol) in 1.04 L of AcOH was added benzoic acid hydrazide (27.28 g, 0.196 mol) in one portion. The reaction was heated to 80° C. and was stirred for 4 hours. The reaction was cooled to room temperature and the AcOH was removed in vacuo to give an off-white solid. The solid was dissolved in 1 L of methylene chloride. The organic solution was washed with 1 L of saturated NaHCO$_3$ solution followed by brine and was dried over Na$_2$SO$_4$. The methylene chloride solution was diluted with an equal volume of methyl tert-butyl ether and the resulting solution was concentrated in vacuo to low volume causing a white solid to precipitate. The precipitate was collected on a sintered glass funnel and was rinsed with methyl tert-butyl ether. The solid was dried in vacuo to give 81.41 g of N-isopropyl-2-(5-oxo-1-phenyl-4,5-dihydro-2,3,6,10b-tetraaza-benzo[e]azulen-6-yl)-N-phenyl-acetamide as a white solid. $^1$H NMR (CD$_2$Cl$_2$) δ 7.57-7.35 (m, 10H), 7.27 (br s, 1H), 7.21 (br s, 1H), 7.10 (t, 1H), 6.87 (d, 1H), 4.89 (m, 1H), 4.19-3.99 (m, 3H), 3.53 (d, 1H), 1.03 (m, 6H); MS 452.3 (M+1), 450.5 (M−1).

Preparation 7(B)

Preparation of 2-(1-(2-fluorophenyl)-5-oxo-4,5-dihydro-2,3,6,10b-tetraaza-benzo[e]azulen-6-yl)-N-isopropyl-N-phenyl-acetamide Following the procedure described for Preparation 7(A), 2-(4-ethoxy-2-oxo-2,3-dihydro-benzo[b][1,4]diazepin-1-yl)-N-isopropyl-N-phenyl-acetamide (Preparation 5(B)) (200 mg, 0.527 mmol) is reacted with 2-fluorobenzhydrazide (81 mg, 0.527 mmol). Purification by medium pressure chromatography eluting with a solvent gradient ($CH_2Cl_2$ to 3% MeOH in $CH_2Cl_2$) provided 180.2 mg of 2-(1-(2-fluorophenyl)-5-oxo-4,5-dihydro-2,3,6,10b-tetraaza-benzo[e]azulen-6-yl)-N-isopropyl-N-phenyl-acetamide. $^1$H NMR ($CD_2Cl_2$) δ 7.73 (m, 1), 7.64 (d, 1), 7.91-7.18 (m, 8), 7.12-7.00 (m, 2), 6.83 (d, 1), 4.96 (m, 1), 4.23 (d, 1), 4.06 (d, 1), 3.80 (d, 1), 3.58 (d, 1), 1.09 (d, 6); MS 470.3 (M+1)

Preparation 8(A)

Preparation of 2-(1-Cyclohexyl-5-oxo-4,5-dihydro-2,3,6,10b-tetraaza-benzo[e]azulen-6-yl)-N-isopropy-N-(6-methoxy-pyridin-3-yl)-acetamide

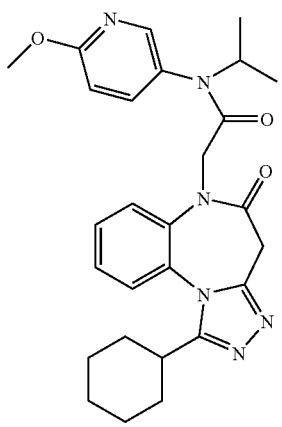

To a solution of 1-cyclohexyl-4H,6H-2,3,6,10b-tetraaza-benzo[e]azulen-5-one (Preparation 4(B) (100 mg, 0.354 mmol) in DMF (10 mL) at 0° C. was added NaH (60% in oil, 15 mg, 0.372 mmol). The reaction was stirred at 0° C. for 30 minutes, was cooled to −10C and 2-bromo-N-isopropyl-N-(6-methoxy-pyridin-3-yl)-acetamide (Preparation 1(B)) (107 mg, 0.372 mmol) in DMF (1 mL) was added. The reaction was stirred at room temperature for 24 h and was diluted with water. The aqueous solution was washed with EtOAc (3×). The combined organic solutions were dried ($MgSO_4$), filtered and concentrated. The residue was purified by medium pressure chromatography eluting with a solvent gradient (1% EtOAc in hexanes to 100% EtOAc) to provide 861.8 mg of 2-(1-cyclohexyl-5-oxo-4,5-dihydro-2,3,6,10b-tetraaza-benzo[e]azulen-6-yl)-N-isopropyl-N-(6-methoxy-pyridin-3-yl)-acetamide. $^1$H NMR ($CDCl_3$) δ 8.11-7.48 (m, total 3H), 7.36 (m, 3H), 6.79 (dd, 1H), 4.99 (m, 1H), 4.12 (m, 2H), 3.92 (d, 1H), 3.65 (d) and 3.82 (d, total 1H), 3.46 (dd, 1H), 2.83 (m, 1H), 2.20 (d, 1H), 2.03-1.86 (m, 3H), 1.68 (m, 2H), 1.54 (m, 2H) 1.31-1.41 (m, 2H), 1.07 (m, 6H); MS 489.4 (M+1), 487.4 (M−1).

Preparation 8(B)

Preparation of 2-(1-cyclohexyl-5-oxo-4,5-dihydro-2,3,6,10b-tetraaza-benzo[e]azulen-6-yl)-N-isopropyl-N-phenyl-acetamide Following the procedure described for Preparation 8(A), 1-cyclohexyl-4H,6H-2,3,6,10b-tetraaza-benzo[e]azulen-5-one (Preparation 4(B) (640 mg, 0.226 mmol) was alkylated with 2-bromo-N-isopropyl-N-phenyl-acetamide (Preparation 1 (A)) (580 mg, 0.226 mmol). Purification by medium pressure chromatography eluting with a solvent gradient ($CH_2Cl_2$ to 4% MeOH in $CH_2Cl_2$) provided 668 mg of 2-(1-cyclohexyl-5-oxo-4,5-dihydro-2,3,6,10b-tetraaza-benzo[e]azulen-6-yl)-N-isopropyl-N-phenyl-acetamide. $^1$H NMR ($CDCl_3$) δ 7.62-7.31 (m, 9), 4.93 (m, 1), 4.10 (d, 1), 3.91 (d, 1), 3.76 (d, 1), 3.45 (d, 1), 2.85 (m, 1), 2.19 (br. d, 1), 1.91 (m, 2), 1.69-1.11 (m, 7), 1.06 (m, 6): MS 458.4 (M+1).

Preparation 9

Preparation of N-Benzyl-2-(8,9-difluoro-5-oxo-1-phenyl-4,5-dihydro-2,3,6,10b-tetraaza-benzo[e]azulen-6-yl)-N-isopropyl-acetamide

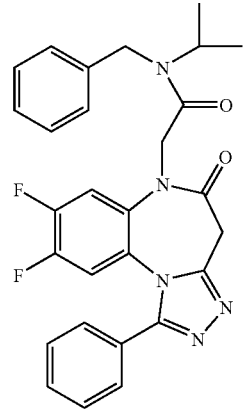

To a solution of KHMDS (0.5 M in THF, 16.6 mL, 8.33 mmol) at 0° C. was added 8,9-difluoro-1-phenyl-4H,6H-2,3,6,10b-tetraaza-benzo[e]azulen-5-one (Preparation 4(C) (2.0 g, 6.4 mmol) in DMF (20 mL). The reaction was stirred at 0° C. for 35 minutes, was cooled to −10° C., and a solution of N-benzyl-2-bromo-N-isopropyl-acetamide (Preparation 1 (C) (1.9 g, 7.0 mmol) in DMF (20 mL) was added. The reaction was stirred at −10C for 2 hours and at room temperature for 24 hours. The reaction was quenched with a pH 6.8 buffer and the aqueous solution was washed with EtOAc (3×). The combined organic solutions were washed with brine (4×), dried ($Na_2SO_4$), filtered and concentrated. Purification by medium pressure chromatography eluting with a solvent gradient ($CH_2Cl_2$ to 3% MeOH in $CH_2Cl_2$) provided 2.01 g of N-benzyl-2-(8,9-difluoro-5-oxo-1-phenyl-4,5-dihydro-2,3,6,10b-tetraaza-benzo[e]azulen-6-yl)-N-isopropyl-acetamide. $^1$H NMR ($CD_2Cl_2$) δ 7.60-7.17 (m, 11H), 6.75 (q, 1H), 4.85-4.38 (m, 4H), 4.10 (q, 1H), 3.60 (q, 1H), 3.41 (s, 1H), 1.21 (q, 3H), 1.13 (q, 3H); MS 502.4 (M+1), 500.3 (M−1).

Preparation 10

Preparation of N-Benzyl-N-isopropyl-2-(5-oxo-1-phenyl-4,5-dihydro-2,3,6,10b-tetraaza-benzo[e]azulen-6-yl)-acetamide

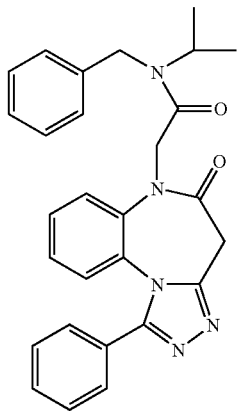

To a solution of 1-phenyl-4H,6H-2,3,6,10b-tetraaza-benzo[e]azulen-5-one (Preparation 4(A) (30.0 g, 108 mmol) in DMF (200 mL) at 0° C. was added NaHMDS (1.0M in THF, 13.6 g, 118 mmol) and N-benzyl-2-bromo-N-isopropyl-acetamide (Preparation 1 (C) (35.2 g, 130 mmol) in DMF (25 mL). The reaction was stirred at room temperature for 24 hours and was diluted with a pH 6.8 phosphate buffer. The aqueous solution was washed with EtOAc (3×). The combined organic solutions were washed with brine (3×), dried ($Na_2SO_4$), filtered and concentrated. Purification by medium pressure chromatography eluting with a solvent gradient ($CH_2Cl_2$ to 12% acetone in $CH_2Cl_2$) provided 13.9 g of N-benzyl-N-isopropyl-2-(5-oxo-1-phenyl-4,5-dihydro-2,3,6,10b-tetraaza-benzo[e]azulen-6-yl)-acetamide. $^1$H NMR ($CDCl_3$) δ 7.64-7.55 (m, 2H), 7.44-7.08 (m, 11H), 6.89 (m, 1H), 4.96-4.08 (m, 6H), 3.57 (m, 1H), 1.17 (m, 6H).

Preparation 11

Preparation of N-Isopropyl-N-(6-methoxy-pyridin-3-yl)-2-(5-oxo-1-phenyl-4,5-dihydro-2,3,6,10b-tetraaza-benzo[e]azulen-6-yl)-acetamide

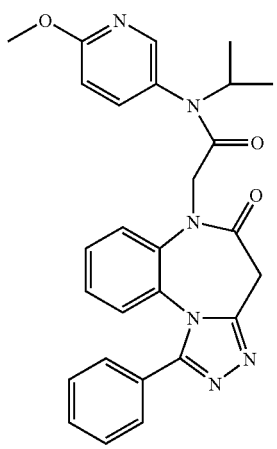

To a solution of 1-phenyl-4H,6H-2,3,6,10b-tetraaza-benzo[e]azulen-5-one (Preparation 4(A) (6.05 g, 21.9 mmol) in DMF (120 mL) at 0° C. was added NaH (60% in oil, 920 mg, 23.0 mmol). The reaction was stirred at 0° C. for 30 minutes and isopropyl-(6-methoxy-pyridin-3-yl)-amine (Preparation 1(B) (6.21 g, 23.0 mmol) was added. The reaction was stirred at room temperature for 24 hours and was diluted with water. The aqueous solution was washed with EtOAc (3×). The combined organic solutions were washed with water, dried ($MgSO_4$), filtered and concentrated. Purification by medium pressure chromatography eluting with a solvent gradient (2% MeOH in $CH_2Cl_2$ to 8% MeOH in $CH_2Cl_2$) provided 8.16 g of N-isopropyl-N-(6-methoxy-pyridin-3-yl)-2-(5-oxo-1-phenyl-4,5-dihydro-2,3,6,10b-tetraaza-benzo[e]azulen-6-yl)-acetamide. $^1$H NMR ($CD_3OD$) δ 8.10 (m, 1H), 7.62 (m, 4H), 7.52 (t, 2H), 7.43 (t, 2H), 7.19 (t, 1H), 6.94 (t, 2H), 4.82 (m, 1H), 4.52 (d, 1H), 4.16 (m, 1H), 3.96 (m, 4H), 3.79 (d, 1H), 1.02 (m, 6H); MS 483.3 (M+1), 481.1 (M−1).

Preparation 12

Preparation of 2-[1-(3-Hydroxy-Phenyl)-5-oxo-4,5-dihydro-2,3,6,10b-tetraaza-benzo[e]azulen-6-yl]-N-isopropyl-N-phenyl-acetamide

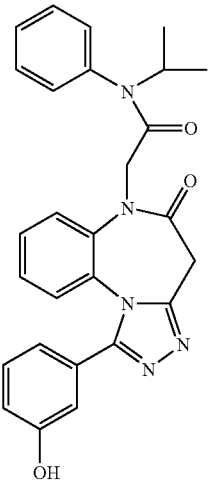

To a solution of 2-(4-ethoxy-2-oxo-2,3-dihydro-benzo[b][1,4]diazepin-1-yl)-N-isopropyl-N-phenyl-acetamide (Preparation 5(B) (177 mg, 0.466 mmol) in glacial acetic acid (4 mL) was added 3-hydroxy benzhydrazide (90 mg, 0.591 mmol). The reaction was heated to 120° C. for 3 hours, was cooled to room temperature, and was concentrated in vacuo. The residue was triturated with 50% $Et_2O$ in hexanes and the solids were filtered. The solids were dissolved in $CH_2Cl_2$ and the organic solution was washed with aqueous $NaHCO_3$, dried ($MgSO_4$) and concentrated to provide 244 mg of 2-[1-(3-hydroxy-phenyl)-5-oxo-4,5-dihydro-2,3,6,10b-tetraaza-benzo[e]azulen-6-yl]-N-isopropyl-N-phenyl-acetamide. $^1$H NMR ($CD_3OD$) δ7.74 (s, 2H), 7.56-7.18 (m, 10H), 6.91 (m, 1H), 4.86 (m, 1H), 4.30-4.10 (m, 2H), 3.98 (d, 1H), 3.71 (d, 1H), 1.06 (m, 6H).

Preparation 13

Preparation of (5-Oxo-1-phenyl-4,5-dihydro-2,3,6,10b-tetraaza-benzo[e]azulen-6-yl)-acetic acid tert-butyl ester Following the procedure described for Preparation 13(A), 1-phenyl-4H,6H-2,3,6,10b-tetraaza-benzo[e]azulen-5-one (Preparation 4(A)) (5.0 g, 18.1 mmol) was alkylated with tert-butyl bromoacetate (2.94 mL, 19.9 mmol). Trituration with Et$_2$O (100 mL), hexanes (30 mL) and EtOAc (10 mL) provided 3.13 g of (5-oxo-1-phenyl-4,5-dihydro-2,3,6,10b-tetraaza-benzo[e]azulen-6-yl)-acetic acid tert-butyl ester. $^1$H NMR (CD$_3$OD) δ 7.68 (d, 1H), 7.60-7.51 (m, 4H), 7.43 (m, 2H), 7.23 (t, 1H), 6.99 (d, 1H), 4.86 (d, 1H), 4.44 (d, 1H), 3.99 (d, 1H), 3.83 (d, 1H), 1.36 (s, 9H); MS 391.4 (M+1), 389.3 (M−1).

Preparation 14

Preparation of Cyclohexanecarboxylic acid hydrazide

To a solution of methyl cyclohexane carboxylate (12 g, 83.9 mmol) in MeOH (50 mL) was added hydrazine (5.3 mL, 1.67 mol). The reaction mixture was heated at 65° C. overnight. The reaction mixture was cooled to room temperature and the resultant solid was collected by filtration and was dried in vacuo to give 4.0 g of cyclohexanecarboxylic acid hydrazide.

Preparation 15

Preparation of [4-(1H-Indol-3-ylmethyl)-5-oxo-1-phenyl-4,5-dihydro-2,3,6,10b-tetraaza-benzo[e]azulen-6-yl]-acetic acid Step A: [4-(1H-Indol-3-ylmethylene)-5-oxo-1-phenyl-4,5-dihydro-2,3,6,10b-tetraaza-benzo[e]azulen-6-yl]-acetic acid tert-butyl ester To a solution of (5-oxo-1-phenyl-4,5-dihydro-2,3,6,10b-tetraaza-benzo[e]azulen-6-yl)-acetic acid tert-butyl ester (Preparation 13(B)) (3.66 g, 9.37 mmol) in toluene (94 mL) was added 1H-indole-3-carbaldehyde (1.63 g, 11.2 mmol) and piperidine (2.78 mL, 28.1 mmol). The reaction was heated to 110° C. in a Soxhlet for 10 hours and was stirred at room temperature for 24 hours. The precipitate was filtered and was washed with toluene to provide 6.47 g of [4-(1H-indol-3-ylmethylene)-5-oxo-1-phenyl-4,5-dihydro-2,3,6,10b-tetraaza-benzo[e]azulen-6-yl]-acetic acid tert-butyl ester. MS 518.5 (M+1).

Step B: [4-(1H-Indol-3-ylmethyl)-5-oxo-1-phenyl-4,5-dihydro-2,3,6,10b-tetraaza-benzo[e]azulen-6-yl]-acetic acid tert-butyl ester Following the procedure described for Example 1(A), Step B, [4-(1H-indol-3-ylmethylene)-5-oxo-1-phenyl-4,5-dihydro-2,3,6,10b-tetraaza-benzo[e]azulen-6-yl]-acetic acid tert-butyl ester (4.84 g, 9.37 mmol) was reduced in EtOH (150 mL) for 3 hours at 80° C. The residue was dissolved in EtOAc and was washed with aqueous NH$_4$Cl (1×) and brine (1×). The organic solution was dried (Na$_2$SO$_4$), filtered and concentrated to provide 4.26 g of [4-(1H-indol-3-ylmethyl)-5-oxo-1-phenyl-4,5-dihydro-2,3,6,10b-tetraaza-benzo[e]azulen-6-yl]-acetic acid tert-butyl ester. $^1$H NMR (DMSO-d$_6$) δ 7.65 (d, 1H), 7.53-7.38 (m, 7H), 7.27 (m, 1H), 7.18 (m, 2H), 6.98 (m, 1H), 6.89 (m, 2H), 4.75 (d, 1H), 4.43 (d, 1H), 3.82 (t, 1H), 3.59 (m, 2H), 1.22 (s, 9H).

Step C: [4-(1H-Indol-3-ylmethyl)-5-oxo-1-phenyl-4,5-dihydro-2,3,6,10b-tetraaza-benzo[e]azulen-6-yl]-acetic acid To a solution of [4-(1H-indol-3-ylmethyl)-5-oxo-1-phenyl-4,5-dihydro-2,3,6,10b-tetraaza-benzo[e]azulen-6-yl]-acetic acid tert-butyl ester (4.26 g, 8.19 mmol) in CH$_2$Cl$_2$ (27 mL) was added TFA (9.5 mL, 0.123 mmol). The reaction was stirred at room temperature for 8 hours and was concentrated in vacuo. The residue was dissolved in CH$_2$Cl$_2$ (50 mL) and Et$_2$O (15 mL) and was stirred for 24 hours. The precipitate was filtered and was washed with Et$_2$O to provide 2.33 g of [4-(1H-indol-3-ylmethyl)-5-oxo-1-phenyl-4,5-dihydro-2,3,6,10b-tetraaza-benzo[e]azulen-6-yl]-acetic acid. $^1$H NMR (DMSO-d$_6$) δ 10.79 (s, 1H), 7.70 (d, 1H), 7.54-7.38 (m, 7H), 7.26 (d, 1H), 7.17 (m, 2H), 6.98 (t, 1H), 6.88 (m, 2H), 4.90 (d, 1H), 4.49 (d, 1H), 3.82 (t, 1H), 3.59 (m, 2H).

Biological Assays

The utility of the compounds of the present invention as pharmaceutically active agents in the treatment of metabolic diseases (such as are mentioned hereinabove) in animals, particularly mammals (e.g. humans), is demonstrated by the activity of the compounds of the present invention in conventional assays and the in vitro and in vivo assays described below. Such assays also provide a means whereby the activities of the compounds of the present invention can be compared with the activities of known compounds. The results of these comparisons are useful for determining dosage levels. The compounds of Examples 1 (A)-7 above were tested in the CCK Receptor Binding Assay described below, and the IC$_{50}$ values for these compounds were found to be in the range of from about 10 nM to about 125 nM under the conditions of that assay. The compounds of Examples 1 (A)-7 above were also tested in the CCK Receptor Functional Assay described below, and the EC$_{50}$ values for functional CCK-A agonism for these compounds were found to be in the range of from about 50 nM to about 1000 nM under the conditions of that assay.

Cholecystokinin (CCK) Receptor Binding Assay

To determine binding affinity, compounds were assayed using membranes prepared from CHO cells that were stably transfected and expressing either human or rat CCK-A receptor. Cell membranes were prepared from one T-75 flask of cells by pelleting cells at 1000×g at 4° C. for 5 minutes and resuspending in 1 ml homogenization buffer (1 mM EDTA, 1 mM EGTA, 1 mM sodium bicarbonate pH 7.4, 100 μg/ml benzamidine, 100 μg 1 ml bacitracin, 5 μg/ml leupeptin, 5 μg/ml aprotinin). After sitting on ice for 10 minutes, the cells were homogenized with a Dounce homogenizer. The nuclei and unlysed cells were removed by centrifugation at 1000×g at 4° C. for 10 minutes. The supernatant was transferred to new tube and then spun at 25,000 g at 4° C. for 20 minutes. The pellet was resuspended in 5 ml binding buffer (20 mM HEPES, pH 7.4, 5 mM MgCl$_2$, 118 mM NaCl, 5 mM KCl, 1 mM EGTA, 100 μg/ml benzamidine, 100 μg/ml bacitracin, 5 μg/ml leupeptin, 5 μg/ml aprotinin). The protein concentration was determined using the BCA Protein Determination Assay kit (Pierce).

The binding assay was performed in a 96 well format using 5 μg (rat CCK-A receptors) or 10 μg (human CCK-A receptors) of membranes in 200 μl of binding buffer (described above) per well. Unlabelled CCK-8 (Sigma) or compounds were diluted in binding buffer and 25 μl of each were added to the assay plate so that their final concentration range was 10 μM to 0.01 nM. [$^{125}$I]-CCK-8 (Amersham) was diluted to 0.75 nM in binding buffer and 25 μl added to each well (final concentration is 75 μM). The assay plates were incubated at at 30° C. for 75 minutes with gentle shaking. Nonspecific counts were removed using a Packard Filtermat Harvester (Packard 96-well Unifilter plate with GF/C membrane presoaked in 0.3% PEI) and washed with cold wash buffer (20 mM HEPES, 5 mM MgCl$_2$, 118 mM NaCl, 5 mM KCl, 1 mM EGTA, pH 7.4). After drying, the plates were counted by the Trilux 1450 Microbeta from Wallac. Data were analyzed using GraphPad Prism software to determine IC$_{50}$ values.

CCK Receptor Functional Assay

To determine functional agonist activity of compounds, calcium mobilization was measured by the FLIPR (fluorometric imaging plate reader, Molecular Devices Corporation, Sunnyvale, Calif.) in CHO cells that stably expressed either human or rat CCK-A receptors. In a 384-well black/clear-bottom poly-D-Lysine culture plate, 15,000 cells in 50 μl medium were plated per well and grown at 37° C., 5% CO$_2$ for 24 hours. After removing media, the cells were loaded with 30 μl per well of Fluo-4 cell loading dye (Molecular Probes, Eugene Oreg.) in filter-sterilized FLIPR Buffer (50% cell culture medium, 50% Hank's Balanced Salt Solution, 20 mM Hepes, pH 7.4, 1 mM CaCl$_2$) with 0.74 mg/ml probenecid (Sigma), according to the manufacturer's instructions. The cells were incubated for one hour at 37° C., 5% CO$_2$. Drug plates were assembled that contained 50 μl of CCK-8 (Sigma) or compounds diluted in FLIPR buffer. Then 15 μl of each compound was added to assay plates so that the final concentration range was 10 μM to 0.01 nM prior to FLIPR analysis. EC$_{50}$ values were determined using GraphPad Prism software.

Food Intake

Male Sprague-Dawley rats (274-325 gms) were acclimated to an automated food intake and locomotor activity assessment system overnight. Food weight and locomotor activity data were collected by computer acquisition in 10-minute intervals. Immediately prior to the start of the dark cycle on the second day, rats (n=5-7/group) were given a PO or IP dose of Vehicle (propylene glycol, 1 ml/kg+ saline, 8 ml/kg) or test compound (1-12 mg/kg in 1 ml/kg propylene glycol +8 ml/kg saline). Food intake was monitored until the following day. Data for each treatment group was compared by paired t-test to determine statistical significance between groups.

Mouse Gallbladder Emptying Assay

Male C57Bl/6J mice, approximately 8 weeks old, were fasted for 18 hours and then orally administered vehicle (0.5% methylcellulose/0.1% Tween 80) or compound. A vehicle of ethanol/propylene glycol/H$_2$O in a ratio of 2:3:5 was used for intraperitoneal (i.p.) administration of compound. A dose volume of 5 ul/gm body weight was used in oral administration and 1 ml/kg in i.p administration. After 30 minutes, the mice (n=5/treatment) were sacrificed by cervical dislocation and gallbladders were removed and weighed. ED$_{50}$ values for gallbladder emptying were determined by Graphpad Prism. All treatment groups were randomized using the program www.randomization.com

What is claimed is:
1. A compound of Formula (I)

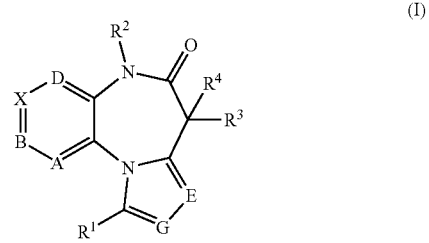

wherein A, B, X, D, E and G are independently —C(R$^5$)— or —N—,
with the proviso that no more than two of A, B, X and D are N at the same time and at least one of E and G is N;

R$^1$ is selected from the group consisting of (C$_2$-C$_6$)alkyl, halo-substituted(C$_1$-C$_6$)alkyl-, (C$_1$-C$_6$)alkylamino-, di(C$_1$-C$_6$alkyl)amino-, (C$_1$-C$_6$)alkylamino(C$_1$-C$_6$) alkyl-, di(C$_1$-C$_6$)alkylamino(C$_1$-C$_6$)alkyl-, aryl, aryl (C$_1$-C$_6$)alkyl-, heteroaryl-A, heteroaryl-A(C$_1$-C$_6$) alkyl-, a 4- to 7-membered partially or fully saturated heterocycle-A, a 4- to 7-membered partially or fully saturated heterocyclyl-A(C$_1$-C$_6$)alkyl- and a partially or fully saturated (C$_3$-C$_7$)cycloalkyl(C$_1$-C$_6$)alkyl- and, when neither of R$^6$ and R$^7$ is phenylmethyl-, R$^1$ is selected from said group and a partially or fully saturated (C$_3$-C$_7$)cycloalkyl;

where heteroaryl-A is selected from the group consisting of thienyl, thiazolyl, isothiazolyl, indolyl, 2-pyridyl, pyridazinyl, pyrimidyl, oxazolyl, furanyl, imidazolyl, isoxazolyl, quinolinyl, isoquinolinyl, benzothiophenyl, benzofuranyl, pyrazinyl and pyrazolyl, and the partially or fully saturated heterocycle-A is selected from the group consisting of pyranyl, morpholinyl and tetrahydrofuranyl, and where the aryl, heteroaryl-A, partially or fully saturated heterocycle-A or partially or fully saturated cycloalkyl group or portion of a group is optionally substituted with 1 to 3 substituents independently selected from the group consisting of halo, (C$_1$-C$_3$) alkoxy-, halo-substituted(C$_1$-C$_3$)alkoxy-, —OH, (C$_1$-C$_3$)alkyl, —CN and halo-substituted(C$_1$-C$_3$)alkyl-;

R$^2$ is —CH$_2$C(O)N(R$^6$)(R$^7$);

one of R$^3$ and R$^4$ is H, halo, (C$_1$-C$_6$)alkyl, (C$_1$-C$_6$)alkoxy- or a partially or fully saturated (C$_3$-C$_7$)cycloalkyl and the other of R$^3$ and R$^4$ is —C(R$^8$)(R$^9$)(R$^{10}$); or R$^3$ and R$^4$ are taken together to form =CHR$^{11}$;

each R$^5$ is independently selected from the group consisting of H, (C$_1$-C$_6$)alkoxy-, —OH, halo, —CN, —NH$_2$ and —NO$_2$;

one of R$^6$ and R$^7$ is (C$_3$-C$_6$)alkyl or a partially or fully saturated (C$_3$-C$_7$)cycloalkyl and the other of R$^6$ and R$^7$ is phenyl optionally substituted with 1 to 3 substituents independently selected from the group consisting of —OH, —CN, halo, halo-substituted(C$_1$-C$_6$)alkyl-, halo-substituted($C_1$-$C_3$)alkoxy-, ($C_1$-$C_6$)alkyl and ($C_1$-$C_3$)alkoxy-; phenylmethyl- in which the phenyl moiety is optionally substituted with 1 to 3 substituents independently selected from the group consisting of —OH, —CN, halo-substituted($C_1$-$C_6$)alkyl-, halo-substituted ($C_1$-$C_3$)alkoxy- and ($C_1$-$C_3$)alkoxy-; or heteroaryl-B optionally substituted with 1 to 3 substituents independently selected from the group consisting of —OH, —CN, halo, halo-substituted($C_1$-$C_6$)alkyl-, halo-substituted($C_1$-$C_3$)alkoxy-, ($C_1$-$C_6$)alkyl and ($C_1$-$C_3$)alkoxy-; and wherein said heteroaryl-B is selected from the group consisting of thienyl, thiazolyl, isothiazolyl, isoquinolinyl, quinolinyl, 3- or 4-pyridyl, pyrimidyl, oxazolyl, furanyl, imidazolyl, isoxazolyl, pyrazinyl, pyridazinyl and pyrazolyl;

two of $R^8$, $R^9$ and $R^{10}$ are independently H or ($C_1$-$C_6$) alkyl and the other of $R^8$, $R^9$ and $R^{10}$ is phenyl, a partially or fully saturated ($C_3$-$C_7$)cycloalkyl, heteroaryl-C or a 4- to 7-membered partially or fully saturated heterocycle-B, where heteroaryl C is selected from the group consisting of indol-2-yl, indol-3-yl, indazol-3-yl, 7-azaindol-2-yl and 7-azaindol-3-yl; said phenyl, partially or fully saturated cycloalkyl, heteroaryl-C or partially or fully saturated heterocycle-B is optionally substituted on carbon atom(s) with 1 to 3 substituents independently selected from the group consisting of ($C_1$-$C_6$)alkoxy-, F, Cl, —CN, —OH, —$CO_2H$, tetrazole and halo-substituted($C_1$-$C_6$) alkoxy-; and $R^{11}$ is phenyl, a partially or fully saturated ($C_3$-$C_7$)cycloalkyl, heteroaryl-C or a 4- to 7-membered partially or fully saturated heterocycle-B, where heteroaryl C is selected from the group consisting of indol-2-yl, indol-3-yl, indazol-3-yl, 7-azaindol-2-yl and 7-azaindol-3-yl; said phenyl, partially or fully saturated cycloalkyl, heteroaryl-C or partially or fully saturated heterocycle-B is optionally substituted on carbon atom(s) with 1 to 3 substituents independently selected from the group consisting of ($C_1$-$C_6$)alkoxy-, F, Cl, —CN, —OH, —$CO_2H$, tetrazole and halo-substituted($C_1$-$C_6$) alkoxy-; a pharmaceutically acceptable salt thereof or a solvate or hydrate of said compound, or said salt.

2. The compound of claim 1 of Formula (II)

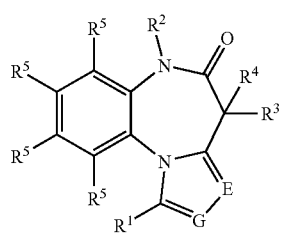

in which $R^1$, $R^2$, $R^3$, $R^4$, $R^5$, E and G are as defined in claim 1; or a pharmaceutically acceptable salt thereof.

3. The compound of claim 2 of Formula (III)

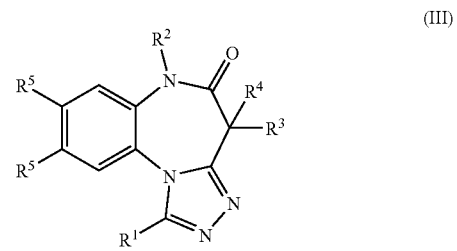

in which $R^1$, $R^2$, $R^3$, $R^4$ and $R^5$ are as defined in claim 2; or a pharmaceutically acceptable salt thereof.

4. The compound of claim 3 in which
one of $R^3$ and $R^4$ is H, ($C_1$-$C_3$)alkyl or ($C_1$-$C_3$)alkoxy-, and the other of $R^3$ and $R^4$ is —C($R^8$)($R^9$)($R^{10}$); or
$R^3$ and $R^4$ are taken together to form =CH$R^{11}$; or a pharmaceutically acceptable salt thereof.

5. The compound of claim 4 in which
$R^1$ is selected from the group consisting of ($C_2$-$C_6$)alkyl, —$CF_3$, phenyl, phenyl($C_1$-$C_3$)alkyl-, heteroaryl-A, heteroaryl-A($C_1$-$C_3$)alkyl-, a 4- to 7-membered partially or fully saturated heterocycle-A, a 4- to 7-membered partially or fully saturated heterocyclyl-A($C_1$-$C_3$)alkyl- and a partially or fully saturated ($C_3$-$C_7$)cycloalkyl($C_1$-$C_3$)alkyl- and, when neither of $R^6$ and $R^7$ is phenylmethyl-, $R^1$ is selected from said group and a partially or fully saturated ($C_3$-$C_7$)cycloalkyl,
where heteroaryl-A is selected from the group consisting of thienyl, 2-pyridyl, pyrimidyl, pyrazinyl and pyrazolyl; and
where the phenyl, heteroaryl-A, partially or fully saturated heterocycle-A or partially or fully saturated cycloalkyl group or portion of a group is optionally substituted with 1 to 3 substituents independently selected from the group consisting of F, Cl, ($C_1$-$C_3$) alkoxy-, —OH, ($C_1$-$C_3$)alkyl, —CN and —$CF_3$; or a pharmaceutically acceptable salt thereof.

6. The compound of claim 5 in which
each $R^5$ is H; or a pharmaceutically acceptable salt thereof.

7. The compound of claim 6 in which
one of $R^6$ and $R^7$ is a branched-chain ($C_3$-$C_6$)alkyl and the other of $R^6$ and $R^7$ is phenyl optionally substituted with 1 to 3 substituents independently selected from the group consisting of —OH, —CN, F, Cl, F- or Cl-substituted($C_1$-$C_3$)alkyl-, F- or Cl-substituted($C_1$-$C_3$) alkoxy-, ($C_1$-$C_4$)alkyl and ($C_1$-$C_3$)alkoxy-; phenylmethyl- in which the phenyl moiety is optionally substituted with 1 to 3 substituents independently selected from the group consisting of —OH, —CN, and ($C_1$-$C_3$)alkoxy-; or heteroaryl-B optionally substituted with 1 to 3 substituents independently selected from the group consisting of —OH, —CN, F, Cl, F- or Cl-substituted($C_1$-$C_3$)alkyl-, F- or Cl-substituted($C_1$-$C_3$) alkoxy-, ($C_1$-$C_4$)alkyl and ($C_1$-$C_3$)alkoxy-; and wherein said heteroaryl-B is selected from the group consisting of thienyl, 3- or 4-pyridyl, pyrimidyl and pyrazinyl; or a pharmaceutically acceptable salt thereof.

8. The compound of claim 7 in which
two of $R^8$, $R^9$ and $R^{10}$ are H and the other of $R^8$, $R^9$ and $R^{10}$ is heteroaryl-C selected from the group consisting of indol-3-yl, indazol-3-yl and 7-azaindol-3-yl, said heteroaryl-C being optionally substituted on carbon atom(s) with 1 to 3 substituents independently selected from the group consisting of $(C_1-C_3)$alkoxy-, F, Cl, —CN, —OH, —$CO_2H$, tetrazole and F-substituted($C_1$-$C_3$)alkoxy-; and $R^{11}$ is a heteroaryl-C selected from the group consisting of indol-3-yl, indazol-3-yl and 7-azaindol-3-yl, said heteroaryl-C being optionally substituted on carbon atom(s) with 1 to 3 substituents independently selected from the group consisting of $(C_1-C_3)$alkoxy-, F, Cl, —CN, —OH, —$CO_2H$, tetrazole and F-substituted($C_1$-$C_3$)alkoxy-; or a pharmaceutically acceptable salt thereof.

9. The compound of claim 8 of Formula (IV)

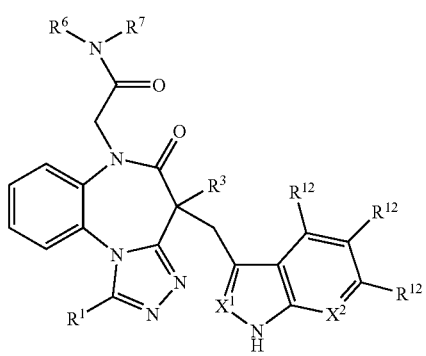

(IV)

in which $X^1$ is —CH— and $X^2$ is —N— or —$C(R^{12})$—, or $X^1$ is —N— and $X^2$ is —$C(R^{12})$—;

each $R^{12}$ is independently selected from the group consisting of H, F and Cl; provided, however, that no more than three of $R^{12}$ are other than H; or a pharmaceutically acceptable salt thereof.

10. The compound of claim 9 in which $R^3$ is H or $(C_1-C_3)$alkyl; or a pharmaceutically acceptable salt thereof.

11. The compound of claim 10 in which $R^1$ is phenyl or 2-pyridyl or, when neither of $R^6$ and $R^7$ is phenylmethyl-, $R^1$ may also be a partially or fully saturated $(C_5-C_7)$cycloalkyl, where the phenyl, 2-pyridyl or partially or fully saturated $(C_5-C_7)$cycloalkyl is optionally substituted with 1 to 3 substituents independently selected from the group consisting of F, Cl, $(C_1-C_3)$alkoxy-, —OH, $(C_1-C_3)$alkyl, and —$CF_3$; or a pharmaceutically acceptable salt thereof.

12. The compound of claim 11 in which one of $R^6$ and $R^7$ is a branched-chain $(C_3-C_5)$alkyl and the other of $R^6$ and $R^7$ is phenyl optionally substituted with 1 to 3 substituents independently selected from the group consisting of —OH, —CN, F, Cl, F-substituted $(C_1-C_3)$alkyl-, F-substituted$(C_1-C_3)$alkoxy-, $(C_1-C_4)$alkyl and $(C_1-C_3)$alkoxy-; phenylmethyl- optionally substituted with 1 or 2 substituents independently selected from the group consisting of —OH and —$OCH_3$; or 3- or 4-pyridyl optionally substituted with 1 to 3 substituents independently selected from the group consisting of —OH, —CN, F, Cl, F-substituted $(C_1-C_3)$alkyl-, F-substituted$(C_1-C_3)$alkoxy-, $(C_1-C_4)$alkyl and $(C_1-C_3)$alkoxy-; or a pharmaceutically acceptable salt thereof.

13. The compound of claim 12 in which $R^3$ is H; or a pharmaceutically acceptable salt thereof.

14. The compound of claim 13 in which $R^1$ is phenyl, or cyclohexyl when neither of $R^6$ and $R^7$ is phenylmethyl-, where the phenyl or cyclohexyl is optionally substituted with 1 to 3 substituents independently selected from the group consisting of F, Cl, $(C_1-C_3)$alkoxy-, —OH and —$(C_1-C_3)$alkyl; or a pharmaceutically acceptable salt thereof.

15. The compound of claim 14 in which one of $R^6$ and $R^7$ is a branched-chain ($C_3$ or $C_4$)alkyl and the other of $R^6$ and $R^7$ is phenyl optionally substituted with 1 to 3 substituents independently selected from the group consisting of —OH, F, Cl, —$CF_3$, —$OCF_3$, $(C_1-C_4)$alkyl and $(C_1-C_3)$alkoxy-; phenylmethyl-; or 3- or 4-pyridyl optionally substituted with 1 to 3 substituents independently selected from the group consisting of —OH, F, Cl, —$CF_3$, —$OCF_3$, $(C_1-C_4)$alkyl and $(C_1-C_3)$alkoxy-; or a pharmaceutically acceptable salt thereof.

16. The compound of claim 15 in which $R^1$ is phenyl, or cyclohexyl when neither of $R^6$ and $R^7$ is phenylmethyl-, where the phenyl is optionally substituted with 1 to 3 F atoms or an —OH group; or a pharmaceutically acceptable salt thereof.

17. A compound of Formula (V)

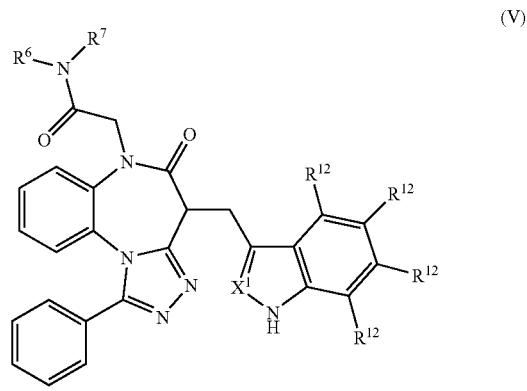

(V)

in which $X^1$ is —CH— or —N—; and one of $R^6$ and $R^7$ is isopropyl and the other of $R^6$ and $R^7$ is phenyl optionally substituted with 1 or 2 substituents independently selected from the group consisting of F, Cl, —$CF_3$, —$OCF_3$, —$CH_3$ and $(C_1-C_3)$alkoxy-; phenylmethyl-; or 3- or 4-pyridyl optionally substituted with 1 or 2 substituents independently selected from the group consisting of F, Cl, —$CF_3$, —$OCF_3$, —$CH_3$ and $(C_1-C_3)$alkoxy-; and each $R^{12}$ is independently H or F; provided, however, that no more than three of $R^{12}$ are F; or a pharmaceutically acceptable salt thereof.

18. The compound of claim 17 in which one of $R^6$ and $R^7$ is isopropyl and the other of $R^6$ and $R^7$ is phenyl optionally substituted with 1 or 2 F atoms;

phenylmethyl-; or 3- or 4-pyridyl optionally substituted with 1 or 2 substituents independently selected from the group consisting of F, Cl, —OCH$_3$ and —OCH$_2$CH$_3$; or a pharmaceutically acceptable salt thereof.

19. The compound of claim 18 in which X$^1$ is —CH—; or a pharmaceutically acceptable salt thereof.

20. The compound of claim 19 in which one of R$^6$ and R$^7$ is isopropyl and the other of R$^6$ and R$^7$ is phenyl, 4-F-phenyl- or phenylmethyl-; or a pharmaceutically acceptable salt thereof.

21. The compound of claim 20 in which one of R$^6$ and R$^7$ is isopropyl and the other of R$^6$ and R$^7$ is phenyl or phenylmethyl-; or a pharmaceutically acceptable salt thereof.

22. The compound of claim 21 in which each R$^{12}$ is H; or a pharmaceutically acceptable salt thereof.

23. The compound of claim 19 in which one of R$^6$ and R$^7$ is isopropyl and the other of R$^6$ and R$^7$ is 3-pyridyl optionally substituted with 1 to 3 substituents independently selected from the group consisting of F, Cl and (C$_1$-C$_3$) alkoxy-, and each R$^{12}$ is H; or a pharmaceutically acceptable salt thereof.

24. The compound of claim 18 in which X$^1$ is —N—; or a pharmaceutically acceptable salt thereof.

25. The compound of claim 24 in which one of R$^6$ and R$^7$ is isopropyl and the other of R$^6$ and R$^7$ is phenyl or phenylmethyl-, and each R$^{12}$ is H; or a pharmaceutically acceptable salt thereof.

26. The compound of claim 24 in which one of R$^6$ and R$^7$ is isopropyl and the other of R$^6$ and R$^7$ is 3-pyridyl optionally substituted with 1 or 2 substituents independently selected from the group consisting of Cl, —OCH$_3$ and —OCH$_2$CH$_3$; or a pharmaceutically acceptable salt thereof.

27. The compound of the formula

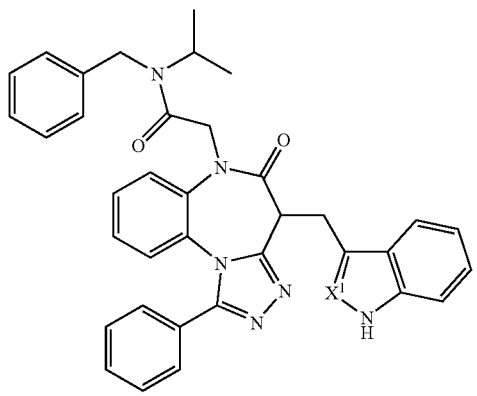

in which X$^1$ is —CH— or —N—; or a pharmaceutically acceptable salt thereof.

28. The compound N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide; or a pharmaceutically acceptable salt thereof.

29. The compound of claim 28 (—) N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide; or a pharmaceutically acceptable salt thereof.

30. The compound (—) N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide.

31. The compound N-benzyl-2-[4-(1H-indazol-3-ylmethyl)-5-oxo-1-phenyl-4,5-dihydro-2,3,6,10b-tetraaza-benzo[e]azulen-6-yl]-N-isopropyl-acetamide; or a pharmaceutically acceptable salt thereof.

32. The compound of claim 31 (—) N-benzyl-2-[4-(1H-indazol-3-ylmethyl)-5-oxo-1-phenyl-4,5-dihydro-2,3,6,10b-tetraaza-benzo[e]azulen-6-yl]-N-isopropyl-acetamide; or a pharmaceutically acceptable salt thereof.

33. The compound (—) N-benzyl-2-[4-(1H-indazol-3-ylmethyl)-5-oxo-1-phenyl-4,5-dihydro-2,3,6,10b-tetraaza-benzo[e]azulen-6-yl]-N-isopropyl-acetamide.

34. A pharmaceutical composition comprising a compound of claim 1 or a pharmaceutically acceptable salt thereof and a pharmaceutically acceptable excipient, diluent or carrier.

35. The composition of claim 34 comprising a therapeutically effective amount of the compound of claim 1 or pharmaceutically acceptable salt thereof.

36. A method for treating obesity in animals which comprises administering to an animal in need of such treatment a therapeutically effective amount of a compound of claim 1 or a pharmaceutically acceptable salt thereof.

37. The method of claim 36 in which the animal is a human.

* * * * *